(12) United States Patent
Tonkin et al.

(10) Patent No.: US 11,779,639 B2
(45) Date of Patent: Oct. 10, 2023

(54) PARASITE VACCINE

(71) Applicants: THE WALTER AND ELIZA HALL INSTITUTE OF MEDICAL RESEARCH, Melbourne (AU); THE UNIVERSITY OF MELBOURNE, Melbourne (AU)

(72) Inventors: Chris Tonkin, Melbourne (AU); Alessandro Uboldi, Melbourne (AU); Malcolm McConville, Melbourne (AU); Martin Blume, Melbourne (AU)

(73) Assignees: The Walter and Eliza Hall Institute of Medical Research, Melbourne (AU); The University of Melbourne, Melbourne (AU)

( * ) Notice: Subject to any disclaimer, the term of this patent is extended or adjusted under 35 U.S.C. 154(b) by 250 days.

(21) Appl. No.: 17/054,872

(22) PCT Filed: May 10, 2019

(86) PCT No.: PCT/AU2019/050433
§ 371 (c)(1),
(2) Date: Nov. 12, 2020

(87) PCT Pub. No.: WO2019/217996
PCT Pub. Date: Nov. 21, 2019

(65) Prior Publication Data
US 2021/0213113 A1 Jul. 15, 2021

(30) Foreign Application Priority Data

May 15, 2018 (AU) ............................... 2018901691
Dec. 5, 2018 (AU) ............................... 2018904620

(51) Int. Cl.
| | |
|---|---|
| *A61K 39/002* | (2006.01) |
| *A61P 33/02* | (2006.01) |
| *C12N 1/10* | (2006.01) |
| *C12N 1/36* | (2006.01) |
| *C12N 9/10* | (2006.01) |
| *C12N 9/12* | (2006.01) |
| *C12N 9/16* | (2006.01) |
| *A61K 39/00* | (2006.01) |

(52) U.S. Cl.
CPC ............ *A61K 39/002* (2013.01); *A61P 33/02* (2018.01); *C12N 1/10* (2013.01); *C12N 1/36* (2013.01); *C12N 9/1051* (2013.01); *C12N 9/1205* (2013.01); *C12N 9/16* (2013.01); *C12Y 204/01015* (2013.01); *C12Y 207/01001* (2013.01); *C12Y 301/03012* (2013.01); *A61K 2039/522* (2013.01); *A61K 2039/523* (2013.01); *A61K 2039/552* (2013.01)

(58) Field of Classification Search
None
See application file for complete search history.

(56) References Cited

PUBLICATIONS

Yu, Y. et al., "Plant-type trehalose synthetic pathway in Cryptosporidium and some other Apicomplexans", PLoS ONE. 2010, 5(9): e12593.
Mahmud, O. et al., "Evolution of the Apicomplexan sugar transporter gene family repertoire", International Journal of Genomics. 2017, 2017:1707231. doi: 10 1155/2017/1707231 Epab May 7, 2017.
Blume, M. et al., "Host-derived glucose and its transporter in the obligate intercellular pathogen Toxoplasma gondii are dispensible by glutaminolysis", Proceedings of the National Academy of Sciences, USA. 2009, vol. 106, pp. 12998-13003.
Uboldi, A.D. et al., "Regulation of starch stores by a Ca2+ -dependent protein kinase is essential for viable cyst development of Toxoplasma gondii", Cell Host & Microbe. 2015, vol. 18, pp. 670-681.
Sugi, T. et al., "Toxoplasma gondii requires glycogen phosphorylase for balancing amylopectin storage and for efficient and for efficient production of brain cysts", mBio 2017, 8:e01289-17 (13 pages).

*Primary Examiner* — Jennifer E Graser
(74) *Attorney, Agent, or Firm* — Hoffmann & Baron, LLP

(57) ABSTRACT

The present disclosure provides mutant parasites, in particular protozoan parasites comprising a mutation of the trehalose-6-phosphate synthase/6-phosphate phosphatase (TPS/TPP)-like gene of *Toxoplasma gondii* (herein referred to as '*Toxoplasma*') or a homologue thereof as well as vaccines comprising same.

22 Claims, 19 Drawing Sheets
Specification includes a Sequence Listing.

Genomic Sequence of TPS/TPP-like gene of *T. gondii* (Introns highlighted) (SEQ ID NO:1)

12471 bp

ATGCTGTACACCAGGGTTTTCTTCCGTGCAGTGGTTCGGACAGACTTCGGTGAACGAGTCGCCGTCGTCGGGTCTTCCCCC
GTCTCTGGGGAATTGGCAGgtgaggctgcgtcgccgtcgcctgcgccgcttcgtgacacggcgaacggtcgaaatgacaa
gggaaaaccgttcgttaggaaaaaccgttcgttctgaggccacagctcttctcgcaactcgcgcgctgcatgtgcctgtc
tcgtagagtctgcatcaccttctggaggtcgggcgtttgcgggggaacgcgacgtcgactgtgcgggacaaaggagaga
ggggctctcgcgtcgcgcggctcagaagtcaaacagttgcatttcgagttttgcgaaacggagaacgaaacatgcatgcg
ccttttgaagaccgtctgtgctgaacacaactccacgaatcggacgagctcaaaccgtgtgtatgtgtgtgtgacggac
tcgaactggcgcgacgtccaaacacaccgtcttcactttgactaaaaaggagctgtttctcgaggacgcttgcaggaag
ttcacccttccttcttctttttcgcattcgaaagaacgaaggaaaaatccatagagacccgcagcggccggtccccgggtc
cgcttccaagtggggtgtgtgtagaccccacggcgggaactcggaggtcgagctgtgcgtctgaagaagcgaccgcccgt
attgtttttcttccccgacgagtttgccgagtttgtctcgcgcgcgaatctgaggaaacgcgcctctgtgtgccgacgg
agttatgtgtctgtcacaatccatgaagctctccttgcggccatcagagctacggactggtcgtggaggccagccgcgcc
gcgagacgctttgatgagcaacttgtttttcgtgggcaaagcggagacaaaaaacggggaagcagtctgagagagacgaag
ctgctcacccgttgccctggacggcgcacaccactgtggttttgcatgtccatctccgtgtcgggcaaatatcgttgcat
gcgccagtttagctttgcgcttctgtgggagacacagtctgtttgccgtgtctcgttcgacgttctctggagttcttta
cacggacgtgcagttcaactcaaggcaccacggaagccgcctgcatgtcgcggttgggcgcgcgcgcaaaaaacgttctc
ttgtttgcggtccgtttccctttcagGCTGAACACGGCCATGAGCTGACCACAAACGAGGATGTCTTCCCTTCGTGGTT
CTCCAAGGAGCCTGTCTACTTGCCGCTAAAGAAACCCATATCTTACAAATATGTTGTTCTCGACGAACGCGGCGACATCG
TGAGgtaggcgacagaggacatagacagaaacatctatttactgtccatgtgtatcaatagttacatctatctacaggg
atctatctacttgaatatatctacagggatctatctacttgaatatatctacagggatctatctacttgaatatatctac
agggatctatctacgtttatgtgtcctatcttctatctaattattcatatacgcgtctacatctgtacatgtgtataaaag
gatatgcagtgtctgtatgcgaaggcggagcggagtgggttgtgtacgaggtccaaggggggcgttgcatgcgaagagca
tttttctcggtttttggacagGTGGGAAGAATGCGAGGGAAATCGCGAGTTGGTGCCCACGGGCTTGGAGATGACGGTGG
AGGATGACGATGGCCTTTTTAGGGAGCAGATGACGAATCGCGGCGACCACGGAGTCGAAGGCGATGACGACgtaagttcc
cttctctgagtttggagtttctctccctctatgcttcttaggaggctcttcttctcttcgttcttgtgaggttctcttct
tctcttcgttcttgtgaggttctcttcttctcttcgttcttgtgaggttctcttcttctcttcgttcttgtgaggttctc
ttcttctcttcgttcttgtgaggttctcttcttctcttcgttcttgtgaggttctcttcttctcttcgttctttgaggt
tctcttcttctcttcgttctttgaggttctcttcttctcttcgttctttgaggttctcttcttctcttcgttctttg
aggttctcttcttctcttcgttctttgaggttctcttcttctcttcgttctttgaggttctcttcttctcttcgttct
tgtgaggttctcttcttctcttcgttcttgtgaggttctcttcttcgcttcgttcttgtgaggttctctcgcgttgcatg
cctctctcgtagcttgctccgccggcgcgttctgatcccgacgccggcctcgttcccgttccccaggggtcttggccctc
ggcggttgtcgccacgtttcttccgctgtgctgcggaactcgaacgcgttgtcgcgtctgggcgcttctctgcggttt
ttcggctcagGTGTCTGTGGCGGCTCTGGACAAGGAGGAGGTGGACGCGCGCAACCGGATGCTGGCGATTCAAGAAGAAG
AGCCTGAGTTCGACGAGAACGACAGCGTAATTGTGTGTGCTCTTGACTTGCCTCTGCGCGTGGTGCGTGTCTCGCCGTCT
CGTGAGGCTTCTCCGCTGCCCTCCTCTCTGCCCGCGTCGTCGACCGACTCTTCCGGCCAAACAGAAAAGCGCGCGGTTTC
ATTCCCGGAAGACGCGGGCGCGAGTGCCCGGCGCTCGAGTTCGACCGTCGCGGCGACTCGGGAGGAGGAAACGACTCGCA
CTGCGAGTTCCTTTCCAAAAGTCGAGGAGACGGCGGAGAGAGGACGCGACAGCTCTCTCGCTCTTTGGCCTGGCGCAGCG
CGCGACGCTGCCGGCGACTTCGGGGAGGCGCTTCAGCCGCGCGCGACGCGCAGCCGACGAGGCACCTTTGAAGTGAGGCC
GAGCAAGAGCGCGTTGTTGCCTTCGCTGTTTCACCTGAGGAAGAAGACGCGGCTGCCTGTGCGTTTCGTCGGGTGGCCGG
GCATCCACGTCGAGAACGAAGAGGAGCAGGCGGAGATTGCGGAGCTGCTGCGAGCCTACGACTGTTCGCCGATCTTCCCA
GACAAAGACGAGTTCGACTGCCATCTCACCTTCTGCCATCAGGTCCTGTGGCCGCTGTTTCACAACGTCGTCGTCCTTGA
CTCCAATACCCAGGTCCCGTTCGACTCCGACCTCTGGGCCAAGTACCAGGCTGTGAACAAACTGTGGGCGGACGCGGTGC
TCCGCCAGGCGCACGAAACCGACATGGTCTGGGTCCACGACTACCACCTGCTCCTCGCGCCCATGCACATTACGCGGAAA
GTCCGACGCGCCAACGTCGGCTTCTTTCTTCACATCCCCTTCCCCTCTTCCGAAATCTTCAGGTGTCTCCCTTGCCGAGA
AGACgtgagtcgaaaagaaaaaacgcgacgcgcgtcaacacctgcggctgtggcggagcggtctctgctcggggggtgta
tgtacacccgagggggcttccggaggtgtgagcaggccaggccgcgagggcggcctctcctccgacgggcgttgccatttt
tttgcatgcaagcttcaggaaacacgctttcttgccgcggctctcggtgcgtctgtctcgttcgttctttgcgttccccg
tatcgatccaaccaacatggacagacgccggttgtgggtctgtgtctgtgtgcatgtatgcgcatctagggacatgcgta
tgagacgcaaatgtcttcaacttgtattctgagtgcgtcctgacgccgatgtgtatactgggcgttgcttcgctgttgcg
ctgtgcaagtccctttgaccggttcggcggctttcctccttctcttgttcagATTTTGCGAGGGATGCTGTGCGCGGACT
TGATTGGGTTTCACCTCTTCGAGTACGCGCGCCACTTTCTGGTCGCATGCAAGCGGCTGCTCGGCCTCGAGCACCATTTT
TGTCGAGGGGGCATTCTGAACATCGAGTACGGCGGCCGCAACGTCTCGGTCCGCATCGGCCATGTCCACATTCAGTACGC
CGACATTCGCTCGAAAATCGAGGCAAACCCGGTGGTTCTGCAGATGGCGCGAGACATCAGgtaaaacacacggacatcca
gagacaggaaagaaagggggaaatggggaaatatgaaagacagggctaccccgctggacggggctcgatttcgagaagct
ccaggtgtctagacaccgcgctttaccgcaagtagttgtgggtgcagagaccaagttgtgtttcctcttcccctttggtg
gaaagtgttcgatccctttccagattccatgcacttctgtatggccgttctgtcgttttccaacgacgcctcggcttctct
gcggtgtccgtacggcacctgtttcccgagtgctgcgacgcgttttctctgaacattccggattttctggatctccgttt
cgcaaaaggaatgtggaatttttagcctccggtgtccgtcgtctctctgcatgcctgttcagACAAAAACACGTCGGAAA
ATTCATCTTCGTCTCCGTGGACCGCTGCGAGAAATTGGCCGGTCTCCTCCTCAAAGTTCGCGCCTTCCAGGCGTTTCTCG

FIGURE 1-1

```
TGACCTACTCTTATGCCAGGgtatgttccttcaaaagcgttgtgcgcgcattgtcctctgttgttctcaaccttcttcct
ccgtcgcgcctgaacggaggctctccottcgcttcccttttctctctctgttcttacttccgtcgacgcttgtgtgg
gtgcttggctgtggttttagacgcgtcgcgcgtgtgaatggagccgcagagtgtatccgcgagaaacgcgcatcaatgc
gtagcgcgaactcgactteottcgaggtccagcttgagtagcctcccagcaaaaggggagtttatgtggacctagacata
cottgaacattgcggtcgacactttcctctcgactccgctgcgttttcagGGAAATGTCGTCCTCATTCAGTACGCGTAT
CCTACCATCAAATACGCAGAAGACACAGAAACCATGGCGACGGAACTCAAAGAGCTCGTGGAGAAAGTCAATGCCCAGTT
CGCCTTGCCAGATCGCCCAGgtgaggagaaatcgcaggttctttttcagtctgccgaggtctctgcagcgtgttctttct
ttgggagcaagggcgtcttttttcgcaaaaccttctaccgcagtcttgggtcactgtgcatcttgccgctgtcgctc
tgcacttgccgctgtcgctctgcacttgccgctgtcgctctgcacttgccgttgtcgctctgcacttgccgctgtcgctc
tgcacttgtcgttgtcgctctgcacttgccgttgtcgagctctccgagttccgccgaatttccttctctctcgcggtc
ggctttcctcttcgcgacagcaaagacaacggcgctgctctgctgcctgggtcgctgtctgtcgaggcgccatgtgaaaa
actcgtcaagaatcattcagtcgtgtctgtgtgtctctctggggaggggagagggggtctcctcatcggctggccttg
tcttctctgcttgcgcggtcaaagaatcgtttctctggggtcgccagtgcactttgcgggtctcttcgtctctctggaac
ggctctcttttcagATTTCCAACATATCGAACTCCACATCCAGCCGGTCGGCTGGGAGGAGAAGTGGGCGTTGTTTACC
GCGGGCGACTGCTTCCTTGACACATCGATCCGAGATGGCCTGAATCTCAATCCGTTCGAATTTATCTGTTGCCACAAAGA
CAACGTCACCGGTGTGATTTTATCAGAGTTCACGGGGTGCAGCAGAGCCCTCGCCTCGGCCATTCGCGTCAATCCTTGGA
AGgtcagttgaaaaagcaagtcagttgaaaaaacaagacacacgcgaagcgcgctgagagacaaagggagttcttctctc
tcgtgcgtctcctctctttcgtctcgctcttcgtctttctcctccctttcttctctggctcgtcttccgctgtagccg
ccactctgcgttcgtccgctgcgcctctgcagGTGGAGGCCGGTGGCAGATGCGATGGACAGAATCATCAACATGCCTGTG
GAGGAGCAGCGCGACCGGTTCACCCGCGACCGCGACTACTTGAGTCACAACAGTACGCAGAAGTGGGCAGACGAAAACAT
TCTGGATCTGCGACGAGCCCGGAAACCAGACGACTTCGTCTACGTCTCTTGGGGTCTCGGCAACACCTTCCGCGTCCTAG
GCATGGACTCCAACTTCCGgtaagaagagttgttaggaccgggcgaacggtcgacggccaaggcaggtccacgcgacagt
gcaacagagagcgggggaagctgtcaaggggcgaaacgcgtcagctctgctcagccaaagacgcgtcggcggccttcggc
ggaagagaaacgcacatgtggttattccagctctcttcaaagccggctgaacaaggtgctctgatgtgccaagaacttcgct
gtcggcgcgcggatctgcgtagcgtcttctgccctagatcgcagcagcaggagtgtcagagccgccgctgcagagaacat
cgcggcgaagaagggcgcctgaagtcgagtccaagaaggagaagccgcgcgcagatccggaggaacgacgaagagca
ggaaggttgccggcgcagagagggaagaacgagaagggcgcgccgagcgcgggacagtgtggaaaaggacagcgaggaatgcgacga
agcagtggagaacggagaagaccaggggatggacaagtcgagaaggaagtcggaggaaatgcgaggaatgcgacga
agaagagagtgggaaggaaccaatgcagcgctttcaaggttacggcaacgaccagttctgcgggagcgctgcgatc
gaccttcgaactcgagttctccagaagcgttttcggacttgttgctgctcctgttttccagGTTTCTGGACACAAATC
AAGTGGTGCGAGGCTACCGAACTTCTCGACATCGCGTCTTCTTCTTCGACTGCGAAGGCACACTCGCGCCGGACAGACGC
CGAATCACTTTTGTACCTGGCGGCGAAAATCTTTTTGCGCAAGGTCGCCCGCCTTCGCCGCAAGTCAAGGACTGTCTCCA
GGCGCTTGTCGACGACCAAAGAAACACTGTTGTCATTCTCTCGGGACGCGACAGACACCTCCTAGAGGAATGGTTCTCTT
CCATCAGAGGCATTGGACTTTGTGCCGAACACGgtaaggcgacagtgtaggtgcttcgacaaatctcgacgtcttcccgc
ccgcctttcgcccgcccccccacacacacacacacacatctacagatacatatgtatatgtatacatatat
atacagttgtgtgcattatacgtacgcatatatatatacgtatgtatgcatatgcatatatataaagcgtacactgatgtgcc
gtatgcagaaacatagacgtagggatgcattctgtggttcacggacatgtgagttggagacagcggaggaatggttt
cgttgagggttcctggaatcgtcgagagtgagagttgcgaagagatgggtggctggatctgaaaataaagttttttcga
gttctgcggaaggaagagcgctagggtgtcggaaacaggagagattctgcagggagaagacacgagatgcgaggttt
ccgaggacacacacctggtccttcactcacatgcagcatctgctagcccacaatccatggtcaatgagactccgttg
ataaaagatccctttccttctaccacttccacgttaatatatatatatttatatatatatatataggtctatgtgta
gatccgtagaaaggcgtatatgcatgtatctgcactttgtgtcggcgtgtatgtaaatgtatttacacatacagatcca
tgaatctccatccatacgttttgtatttatgtagacatatatatatatatatatatgtgtatgtataggggggagat
tgtgtgttttttgtcgtttgcttgagaggtttgtttcagtgcgttgtggtgataagagcttttggagtgacctgcggt
tggttttcagGTTTTTACTACCGGGTTCCGGGCATCACGGGGGACCAGTGGCACTGCATGTCTCGTCAAACAGACTTCAC
ATGGAAGCAAGTGGCGATCGAGCTGATGCTGCAGTATGTGAAGCGAACTCAGGGCTCATTCATCGAAAACAAAgtaggtg
aacggtggtttttcttttctggaacgtctcccttgcgtggacctcacgctctctcctcgaaacgtcgccgcccgccac
acagagctgccgcgcgccttctctctcctcgactagcgaaactcgcaggtcgcggtcgagcggagtcgaagacgagtctc
tttttgcttcagttgcgaagcgcgtcgttctgacttgggcgtccacgaagaactgcaaaaaactgtcgtggaacgt
tctcaagagtgcaaaacgacagttgtgacgctggaccccaagctgacttccaagtgcgacgcgaagtcgctgcgt
ttgaacacttgccagttgcgagaggatctctgtagtccttgcagacatttcatgtcgcgcgattccttctctgagcttg
tgcgcagtcttcttgtcggcagttccttgcggctggcggtagaacgtaccaaacacactggcgtttacacagagcccg
ctcgtctgattcacctgtgaaggaggagtgcgagggtggctgttctggacagcttttgttcaccgtgacgtcgcct
caaaactccggaatgcacatcgcagagtcggattcctgcgtctacagacgctggcttttctcttgtcatgtgcctccag
tcctgctcggactcgaagctgaatgtgacaacagttgaattcttctctcgttctgctgcaGGAAGTGCTCTCGTCTTCCA
GTACCGCGACGCAGATCCGGATTTCGGCAGCATGCAAGCCAAGGATCTCTCGAACTACCTCGGgtgagaaactcgcattc
tgcgcgaacaccctcagcgcttctcaggcttttgttcgccgcattcttcagacaaggaaaatgggtcgtgaaggcact
ggtcaggcgccttcgcctctcgccttcgggtgcgcaagtgtatcgaaaaggaatctgattttcttttcagGGAACTGCT
CTTCGGCTATCCTGTCTCGGTCATGAGCGGGAAAGGCTACGTGGAAGTGAAACTGCGAGGTGTCAACAAAGGGCATGCAG
TCGAGAAAGTTCTGCGGAAACTCAGCAACCTCCACGGAGACGTCGACTTCGTTCTCTGCGTCGGAGATGACAGgtaaaca
gaccaatgaaagctgacgaacgagacgcaagaaaactcgcacgtgagccatctactccactcacgtgaatacacataca
tgcacatgcacacatactacctacatatgcatatatatatatatatatatatatgtgcatatatatat
atatatatgtatatgcgtagagaagtacttgtgcagttctgtgtttgtgagtggatattcctgtgcacagagcgtagcg
```

FIGURE 1-2

```
ttttcatgtgagttttagaagtgaatgtatgctgtttagtctggagaaggcgtcggctcttttcagggggcatactttt
gaggaaaggtgagtttcgcagttgagggaacggyaagcgagggtgttggcaggacgcgattgagaagactgcattccaga
ggccttctttcttctgaattttcttcagAAGCGACGAAGACATGTTCGCGGTCATCAACGCCATGACGGAAGACGGGGA
CCAGCTGTGCCTGCCAGAGGGCAGCGGCGCCGGGAGCAGCGGCCTCTATCGCCACACACAGTCGAAGGATCGAATTCCTA
GACGCAACTCTGTCTCTgtacgcggcggtcgatgacgaaacgcgtcaaaattggggaagcgagctgtcctcagagatct
gggtacttcttccacacttacagacgtatacatggctttctgcgcagttgctgctgtatctgtaaatgtttatgccgtc
tttgtccaacatacatatacatatacatatatatatatttatttatttaatatatttaatatattgatattatataagt
gtatatatgtacagaaacgttgcagaagtgcgtaggttgatacatgtgtgccgtgagaggaagaagccctgacgtaccg
tgagatgtgtgtcgcgagagtttgaaaagacatacacatatacatatatacatatatatacatatatatatgtatata
tatgtatatatatgtatctcgaactgttgagatacacgtctgcataggtgtaagtaactagatgccaatacacagacaac
agactttatttgaatgtgcgtacatcttttctctcgctttcagTCGGATGAGAACCGAGCAGAAGCTGTCGTTGGAAACG
TGGAGGGACTCATGAAGCGTGACGGGTCGATGCAGCATGCGGGGGCGCTCGGCAGCGGCTTGACCTCTGCGTCTTCCAGC
ACAAGTCTCAGTGGGCACACAAAGgtaaaggaaacaactgcggggtgaaggcgtagaaagcgagcaggaaggcgaggagg
aagagaagacaaagcgaggagcgaggagagaccgaacgcagaaacaaggaggtgacgcaaagyagyagagcggagyag
gaaggagggacgaacacaggcaaaagaagagcagcagaagggaggagacgaacagcgaggagagaagagagcagaca
aggagacgatacaacagagyaaagaaagcaggyyaagacgcgcggggcgtaccagagaagaagaaaggagacaggtacg
aagcgaacggtaggycggaggyagggagcgagagaagagaaacggagaggagagactcaaccttgcgttcgaacaaggat
gcagagcacggagaagaatcgaaagggctcgcgtagccgacgatacaagyagyagaaaacagaaacaaaagacagagaa
aaagaaacaagacacaggagcgcagacacagcatgaggaaacgaggacgyaagtgatgcaagtgtgtatctcttgttgt
gtcggaatgtgcagAAAACGAGTCCTCACTTTTTCACATGCACAGTCGGCAAGAAGCCGTCCAACGCTCGgtatgttttt
tttaaaaaacaaagtttcttagagcacttttccccgcgttttcgtctcgtgccgtctcatctgcgtctttccttctcagc
gcattacttcacttttcttttttcttttgttgttctaatccagtcttcttgcgtgtgtgaatgcgtctcgtccttc
gtctctctccatgcgtatttctgttcctctcttggccgcagtcgctccgtcaaggggaacgcaaacgacgcgcgac
gtggaacgcgaaatgtgcagaaggtgctccacggtctccagagttttctgaagtgtgtcttcaagttcgccgaacaacg
attcgtgtcgactgttcggataacttcaaaagacgacgcgccatcctggttttcctcctctcgttctcggctttggcttt
ttcgaaatgcggagttcctctgtttcattcgtctttttggcccgttctcgatctcttcacagGTATTACCTCAACGACAC
TGAGGATGTCTCCGATCTCCTCGACTCTCTGCAGCAGTGCACTGAGAAGgtaaacttcttgccccagacacactctgtt
cgcaggtggaggcgtccgccgtgtttttcagtttaatccggttcttgccttgggcctctccccccttgttctacgcc
atcggctctcttcatgcgcgtcccgtcatgtgccgtcgcgttctctttgcggtgtccctccttctcttttcctgcttcgt
gtgtgtttctcgtcgttttctgtggcgtcaaccccatcactggctccctcctccatcctgtctctcttctgctgtcgcgt
tctctctctttttctgtgtttgttcaatccgctgagctttcatctgctgcagctgtgctcggctgtgtggttctcc
aggGACGGGAAGGAGCAGTGGAGTTCGTCGAAGGACGCGAGTTGCCTCTCGGCGCCAGTCGTGGCGGCCGCGGCGGCTGCG
GGCTCGCTCGCGGGGAACGCGGCGGTGCAGCTGAGGAAAGGCGACAGCGCAGCTTCGAACTTTGCGAGTCTGTGGAGATC
GCCTCTGGGATCAGGAGCAGGTCGCACGAGAGAACGAACGCTCGCGCAGTGGGCGGGGCAGGCACCGAGCGCCATCTTCA
GTCGCCCCGTCGGTGCCGTTGAAGTTCGCGCCAACGCAGCTGGCAGCACAGATCGCCCAACAGACGAGTAG
```

The proto-spacer sequence is indicated by underlining followed by the PAM sequence AGG.

FIGURE 1-3

**N-terminal sequence of the TPS/TPP-like gene of *T. gondii* (first 200 nucleotides) (SEQ ID NO:2)**

ATGCTGTACACCAGGGTTTTCTTCCGTGCAGTGGTTCGGACAGACT
TCGGTGAACGAGTCGCCGTCGTCGGGTCTTCCCCGTCTCTGGGGA
ATTGGCAGgtgaggctgcgtcgccgtcgcctgcgccgcttcgtgacacggcgaacggtcgaa
atgacaagggaaaaccgttcgttaggaaaaaccgttcgttctgaggc Exon sequence is indicated in upper case. Intron sequence is indicated in lower case.
The proto-spacer sequence indicated by bold and underlined text. The PAM sequence is highlighted.

FIGURE 2

**Genetic ablation of TPS/TPP in *Toxoplasma***

A. CCCGTCTCTGGGGAATTGGCAGGTGAGGCTGCGTCGCCGTCGCC WT (SEQ ID NO:4)

B. CCCGTCTCTGGGGAATTCGGCAGGTGAGGCTGCGTCGCCGTCGC RH:Δ*hxgprt*:Δ*tps/tpp* cl-1 (SEQ ID NO:5)

C. CCCGTCTCTGGGGAAA(+182)GGCAGGCAGGTGAGGCTGCGTCGCCG RH:Δ*hxgprt*:Δ*tps/tpp* cl-2 (SEQ ID NO:6)

D. CCCGTCTCTGGGGAAT-GGCAGGTGAGGCTGCGTCGCCGTCGCC RH:Δ*hxgprt*:Δ*tps/tpp* cl-23 (SEQ ID NO:7)

E. CCCGTCTCTGGGGAATTTGA(<1000)TTAGGCAGGTGAGGCTG Pru:tdTomato:Δ*tps/tpp* cl-2 (SEQ ID NO:8)

F. GACAGACTTCGGTGAACGA(-58)GTCGCCTGCGCCGCTTCGTG RH:Δ*hxgprt*:Δ*tps/tpp*:HxK-HA cl-1 (SEQ ID NO:9)

FIGURE 3

**Genomic Sequence of *T. gondii* hexokinase (HxK) (Introns highlighted) (SEQ ID NO:23)**

3277 bp

```
ATGCAGCCTCGTCAACCAGGCGACGAAGCGAAGCAGCTCGCGGAGCTGGAGgtgtggacatcacagctgggtcgacgggg
acoataaaatctgtgtaattcgtccgtgtgcagtgtgggtgtgtacgtaggttatgcacacatttgagttgatgctgat
ttgcacgaatagcgctgcattttggcgccttgtgtaaatgcgccgggaaaaatacgtcaaaatgtcctattttcgtccc
tggtgctgccacctcgggaatgttcctggcattcgaagatgcacggtggaaaatggtcgtacctacttcccccgatc
aagtgcaagtctgttggagcctgtatttgtgtgtgcagggttgtgtgacaagcagctgcccaaaagctgccttgatt
tcagcacgaacaactggqtctctgtgcgacgcagtagcgagaaacctgagtttaccgggqagcgqqqagtgac
aaatgtgagattctgagcacatgcggqccggqaaagagctttttttagcatgcaacgattctgtgtgacaggccaaa
gaacaacagtcctatctttccaattccatgtccgctcagGTCGTTCGCCAAATGATGACCCCGACACGCGAGGTTCTGC
TGGAGCTGCACGAAAGCTTTTTGAAGGAGCTACAACGCgtgagtactgtggctctgtttgacaaattgctattcgttt
caaggagtaactttcagtggtqggaaggccgtgcactaccatgctctgcctctctagcaacccqgtttacactttgt
ctctgtgaaatgatcgaagcgagagagaattttcgttttcaagcgtcacggtactgacagtctttcagaacggagtggga
tgactgtaccgtctggttgcatgacactcgtgcaagaaggccgttgctgttcttgtgcgttcgctctggtgcttctcg
gttgtgcatatttgctgttttgttcgaagctctctccgctcttcgctgcctcgctttcgggcgcacgagacagcttcga
ttcatctccattcgtcgtctgaaactggatttttgcgctcagGCTTGGAAATGCACAAGAGACACGGCATCACATGGG
TGCCTGAGGAATGCTCGATGAAAATGCTGGACAGCTGCGTGTCGAATCTGCCGACTGGTGCCGAAGTTGGCGAGGCATAT
GCCATCGACTTCGGAGGCTCGACATGCCGGGCTGTTCGTTGTTCTCTTCTTGGCAAGGGCAAAATGGAAATTATTCAAGA
CAAAATCTGgtaagcagcacttaacgaatggqcgttggqacgtcgtgctagcqgccqgtgtttgttgagagcgaacgagaagc
tggcgagcctgtcatcgtggtgctcaatgtgtgcttgcttgcgtgtttacgtacagCCTGAGAAGCGCGGAACATCGA
TGCGCCAAGGGATTCATGGACAAGAAGGCAGGAGGCAAAGAACTGTTCGACCAATTCGCCATGTGCATCCGCGGCCTGAT
GGATAGGTCCGGAGACCTGAAGAAGGCGGAAGAGACCAACACACCTGTCCCAGTTGGATTCACTTTCTCTTTTCCTTGCG
CCCAAGCGgtgagtctttggaatcgtaaacagagcactattgggtcctcgatgtcggtaactttcccgagaggaagagt
gagggaacgacactttgctgacatttcttcaggaactggcaaggccacaaatgcggcgaaaggtggaagccgggttcctg
atgtcgtgactcatacacttcgagaaagccatcgattttgtgttcagGCGTTGAACTCTAGCTTTCTCATTGAGTGGAC
AAAGGGCTTCGAAACTGGCCGCGAGAACCCGGATCGTGTAGAAGGCAAAGATGTGGCAGTGTTGCTTGCCGATGCACTGC
AACGTCATAACGTTCCTGCTGTCTGCAAGGCTATCGTGAACGACACGgtaagcacattttacgtggaagcgtgagagacc
atggttgtgtccgaaggcataactagccgtgcagccgatgccctccttgatgtgcgcatccacgcgggagtattcttttt
tctgctgactatagtctgttgagtgggaaagccgtgagccgctcactgtgaaccgtcttttggacttcgcttgcctctg
tcagGTTGGCACATTGGTGTCTTGCGCATATCAAAGAGTGCCAAGCCACTCCGGAGTGCCGTGTTGGACTCATCATCGGCA
CCGGGTTCAACGCGTGCTACGTGGAACCTGAAGCTAGCAACTATGGCTACACGGGTACCGTCGTGAATATGGAGGCAGGC
AACTTCCACAAGGATCTTCCGCGCAACGAAATCGACGTCGAGgtggtctgtggtgatgcaggatctggaagattaacta
tccttgcgcacatgcaagagttggtgttcttttgaggacggtatatgaggtgcagttatggqcgctcaattaggctatc
ctgttacatttgttctctgcgttcagGTCGATGAAGACACACAACAGAGGCAAACAGCAATTCGAGAAACTCGTGTCG
GGCTACTACATCGGCGAAATCGTCCGGGTCGCTGCAGTCAGAGTATTTGGCGCCCGTGCCCCCGAGAAAGCAAGgtaaac
aatcttctgtgtgatgttgaaggctgctgggcgaatccttggttcttagacaccgcgacacggattccccgaataaca
caacttccggttactgctgtgtatgtgttttctcagTGTCAGACACTCGATTCATGGTGAAACGGCCTCGACGATCCGTGA
TGACCATAGCCAGGACAAAGCCGCCAGCATTCAGGCTATCAAGGAGTGCTGGGGTGTGACGATGGACTTGGACGACATCA
AGTGCATCTGGGAGATTTGCCGACTCGTCTTCGACCGCTCAGCCGCGTTCGCTGCAACGCTGGCGGTCGCTCTGTGCTAC
CGAACAGGCgtaagtccgtagtaactaaaattttttccaaactataccggcgcattcagttctgattttttccgttca
ggcgcgattcctaaacgaggtggacgctgtgattctgcttgtgctgttgtgcagCGACTTGACACCGGATCCACCGTAGG
AATTGATGGTGCTTTGTATGTGAAGAACCAGTGGTACCGGGAGGCTGTTGAGTACTACACAAAATTGGTCGCCGGCGACG
CGGCGAAAAACATTCACTACTGCATTGCGGATGACGGCTCTGGCAAGGGTGCTGCTCTGATCGCAGATGTGAACTGA
```

FIGURE 4

A
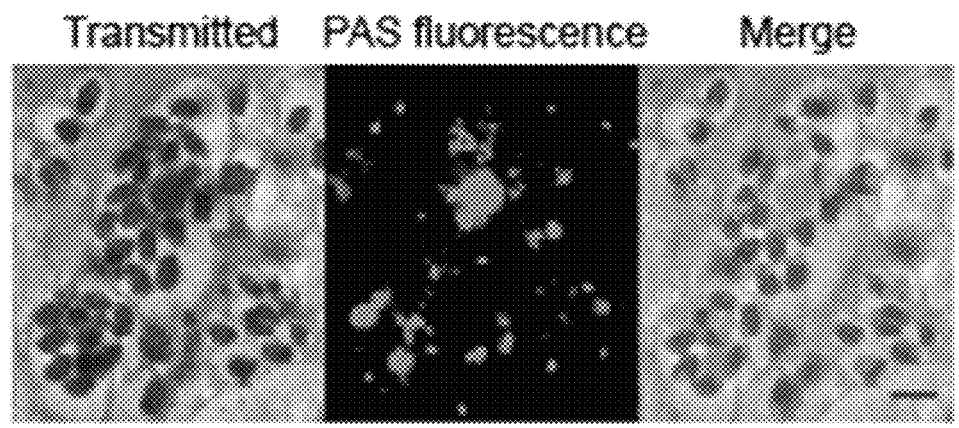
B
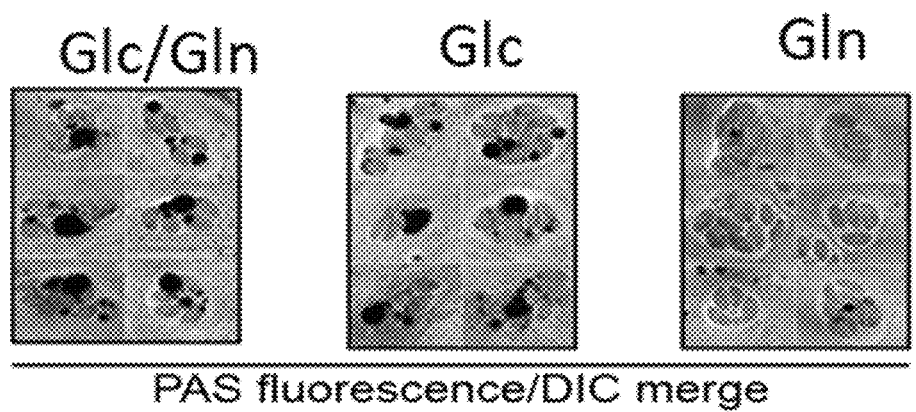
FIGURE 6

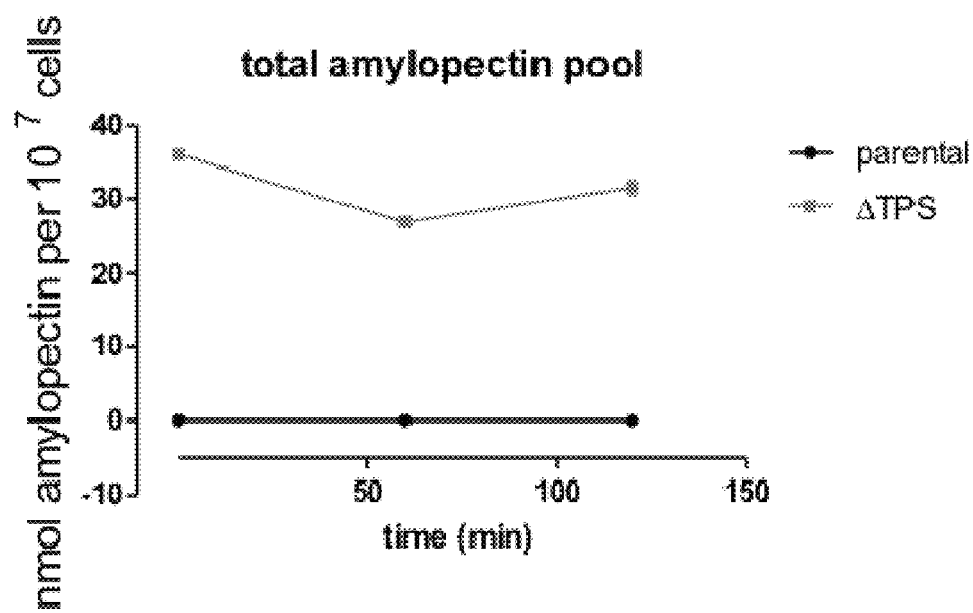
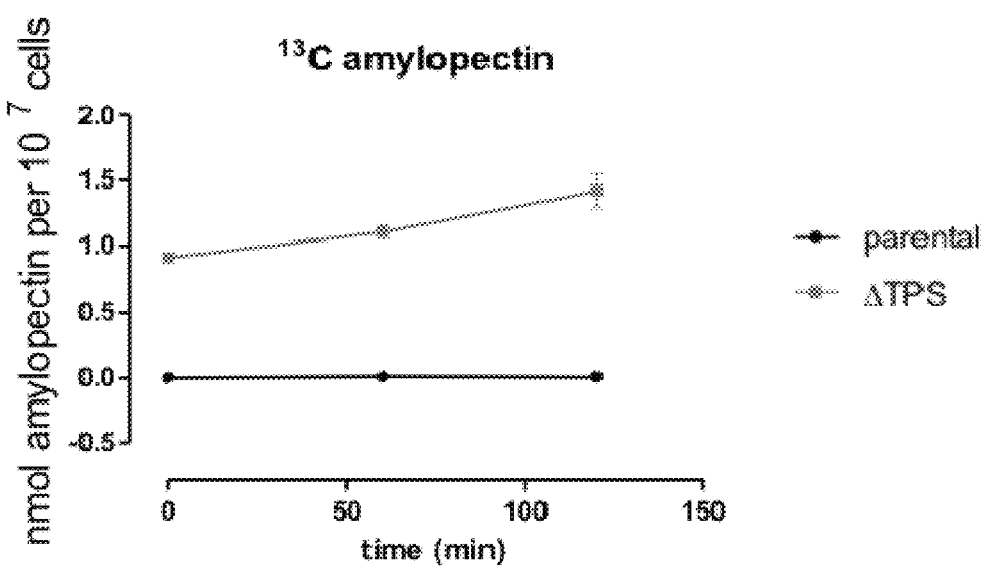
FIGURE 7

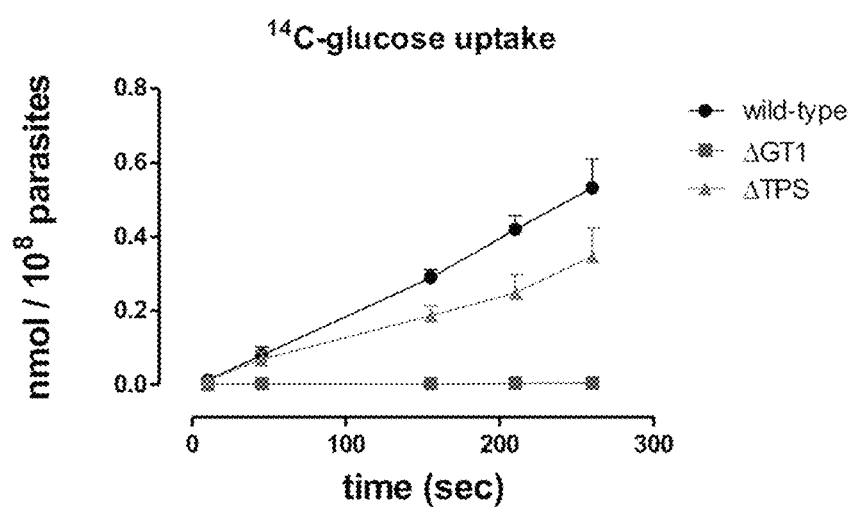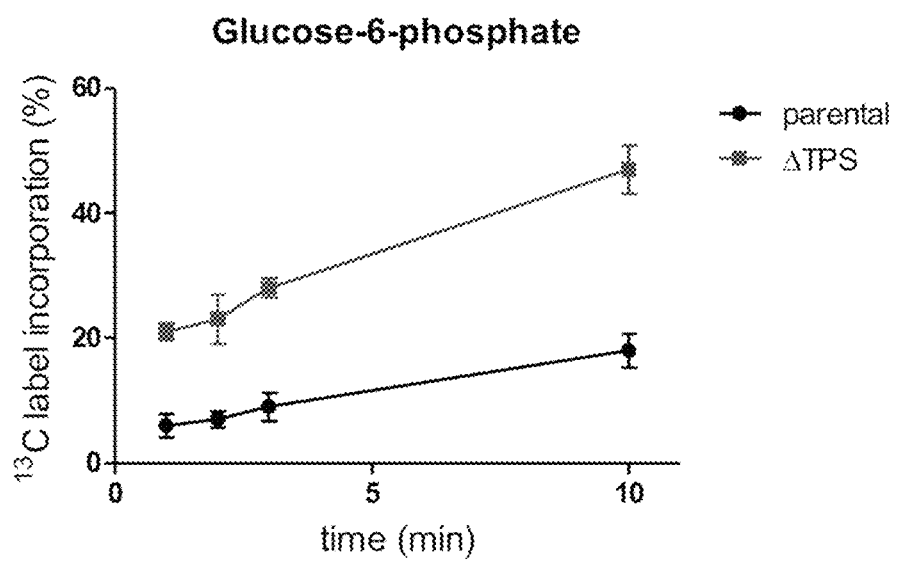
FIGURE 9

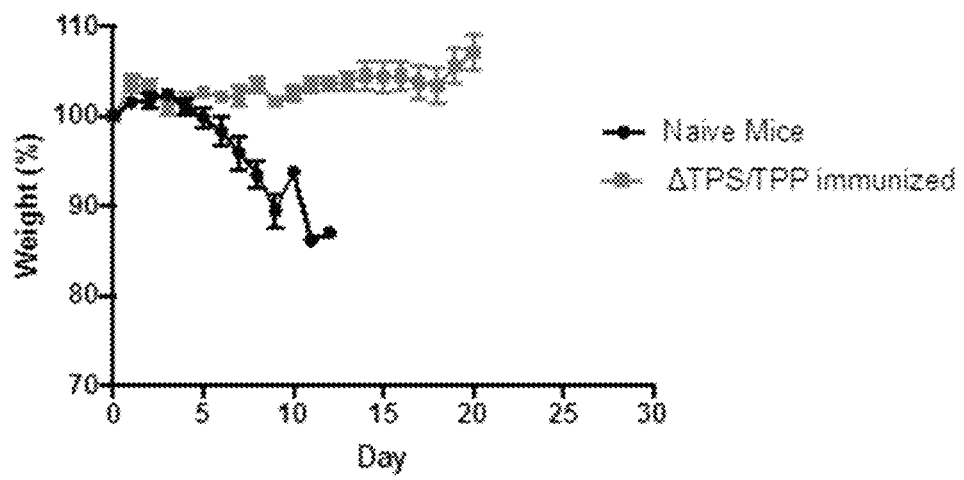
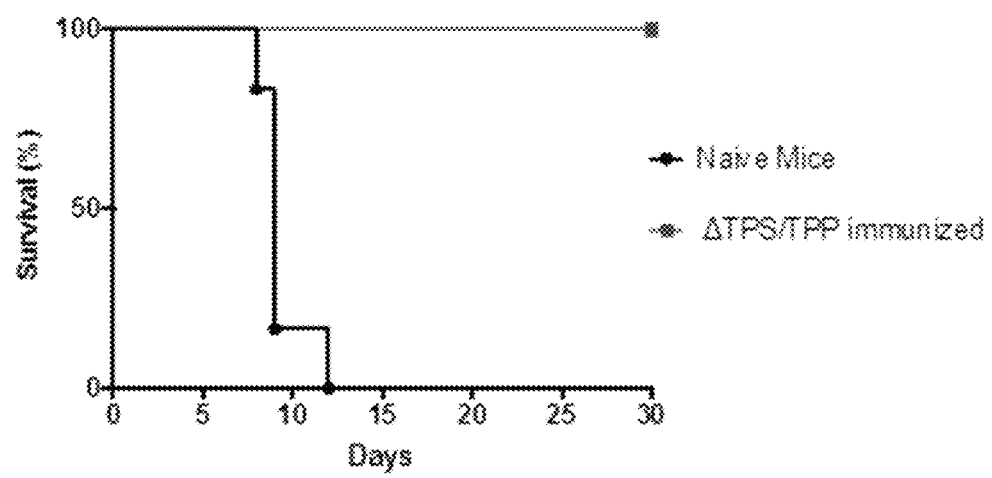
FIGURE 17

SEQUENCE LISTING

```
<160> NUMBER OF SEQ ID NOS: 63

<210> SEQ ID NO 1
<211> LENGTH: 12471
<212> TYPE: DNA
<213> ORGANISM: Toxoplasma gondii

<400> SEQUENCE: 1
atgctgtaca ccagggtttt cttccgtgca gtggttcgga cagacttcgg tgaacgagtc      60
gccgtcgtcg ggtcttcccc gtctctgggg aattggcagg tgaggctgcg tcgccgtcgc     120
ctgcgccgct tcgtgacacg gcgaacggtc gaaatgacaa gggaaaaccg ttcgttagga     180
aaaaccgttc gttctgaggc cacagctctt ctcgcaactc gcgcgctgca tgtgcctgtc     240
tcgtagagtc tgcatcacct tctggaggtc gggcgtttgc gggggaacgc gacgtcgact     300
gtgcgggaca aagggagaga ggggctctcg cgtcgcgcgg ctcagaagtc aaacagttgc     360
atttcgagtt ttgcgaaacg gagaacgaaa catgcatgcg ccttttttgaa gaccgtctgt     420 gctgaacaca actccacgaa tcggacgagc tcaaaccgtg tgtatgtgtg tgtgacggac     480
tcgaactggc gcgacgtcca aacacaccgt cttcactttg actaaaaaag gagctgtttc     540
tcgaggacgc ttgcaggaag ttcaccccttc cttcttcttt ttcgcattcg aaagaacgaa     600
ggaaaaatcc atagagaccg cagcggccgg tccccgggtc cgcttccaag tggggtgtgt     660
gtagacccca cggcgggaac tcggaggtcg agctgtgcgt ctgaagaagc gaccgcccgt     720 attgttttt cttccccgac gagtttgccg agtttgtctc gcgcgcgaat ctgaggaaac     780
gcgcctctgt gtgccgacgg agttatgtgt ctgtcacaat ccatgaagct ctccttgcgg     840
ccatcagagc tacggactgg tcgtggaggc cagccgcgcc gcgagacgct ttgatgagca     900
acttgttttt cgtgggcaaa gcggagacaa aaacggggaa gcagtctgag agagacgaag     960
```

```
ctgctcaccc gttgccctgg acggcgcaca ccactgtggt tttgcatgtc catctccgtg    1020
tcgggcaaat atcgttgcat gcgccagttt agcttttgcg cttctgtggg agacacagtc    1080
tgtttgccgt gtctcgttcg acgttctctg gagttcttta cacggacgtg cagttcaact    1140
caaggcacca cggaagccgc ctgcatgtcg cggttgggcg cgcgcgcaaa aaacgttctc    1200
ttgtttgcgg tccgtttccc ttttcaggct gaacacggcc atgagctgac cacaaacgag    1260
gatgtcttcc cttcgtggtt ctccaaggag cctgtctact tgccgctaaa gaaacccata    1320
tcttacaaat atgttgttct cgacgaacgc ggcgacatcg tgaggtaggc gacagaggac    1380
atagacagaa acatctattt tactgtccat gtgtatcaat agttacatct atctacaggg    1440
atctatctac ttgaatatat ctacagggat ctatctactt gaatatatct acagggatct    1500
atctacttga atatatctac agggatctat ctacgtttat gtgtctatct tctatctaat    1560
tattcatata cgcgtctaca tctgtacatg tgtataaaag gatatgcagt gtctgtatgc    1620
gaaggcggag cggagtgggt tgtgtacgag ggtccaaggg ggcgttgcat gcgaagagca    1680
tttttctcgg ttttttggaca ggtgggaaga atgcgaggga aatcgcgagt tggtgcccac    1740
gggcttggag atgacggtgg aggatgacga tggcctttt agggagcaga tgacgaatcg    1800
cggcgaccac ggagtcgaag gcgatgacga cgtaagttcc cttctctgag tttggagttt    1860
ctctccctct atgcttctta ggaggctctt cttctcttcg ttcttgtgag gttctcttct    1920
tctcttcgtt cttgtgaggt tctcttcttc tcttcgttct tgtgaggttc tcttcttctc    1980
ttcgttcttg tgaggttctc ttcttctctt cgttcttgtg aggttctctt cttctcttcg    2040
ttcttgtgag gttctcttct tctcttcgtt cttttgaggt tctcttcttc tcttcgttct    2100
tttgaggttc tcttcttctc ttcgttcttt tgaggttctc ttcttctctt cgttcttttg    2160
aggttctctt cttctcttcg ttcttttgag gttctcttct tctcttcgtt cttttgaggt    2220
tctcttcttc tcttcgttct tgtgaggttc tcttcttctc ttcgttcttg tgaggttctc    2280
ttcttcgctt cgttcttgtg aggttctctc gcgttgcatg cctctctcgt agcttgctcc    2340
gccggcgcgt tctgatcccg acgccggcct cgttcccgtt ccccaggggt cttggccctc    2400
ggcggttgtc gccacgtttt cttccgctgt gctgcggaac tcgaacgcgt ttgtcgcgtc    2460
tgggcgcttc tctgcggttt ttcggctcag gtgtctgtgg cggctctgga caaggaggag    2520
gtggacgcgc gcaaccggat gctggcgatt caagaagaag agcctgagtt cgacgagaac    2580
gacagcgtaa ttgtgtgtgc tcttgacttg cctctgcgcg tggtgcgtgt ctcgccgtct    2640
cgtgaggctt ctccgctgcc ctcctctctg cccgcgtcgt cgaccgactc ttccggccaa    2700
acagaaaagc gcgcggtttc attcccggaa gacgcgggcg cgagtgcccg cgctcgagt    2760 tcgaccgtcg cggcgactcg ggaggaggaa acgactcgca ctgcgagttc ctttccaaaa    2820
gtcgaggaga cggcggagag aggacgcgac agctctctcg ctctttggcc tggcgcagcg    2880
cgcgacgctg ccggcgactt cggggaggcg cttcagccgc gcgcgacgcg cagccgacga    2940
ggcacctttg aagtgaggcc gagcaagagc gcgttgttgc cttcgctgtt tcacctgagg    3000
aagaagacgc ggctgcctgt gcgtttcgtc gggtggccgg gcatccacgt cgagaacgaa    3060
gaggagcagg cggagattgc ggagctgctg cgagcctacg actgttcgcc gatcttccca    3120
gacaaagacg agttcgactg ccatctcacc ttctgccatc aggtcctgtg gccgctgttt    3180
cacaacgtcg tcgtccttga ctccaatacc caggtcccgt tcgactccga cctctgggcc    3240
aagtaccagg ctgtgaacaa actgtgggcg gacgcggtgc tccgccaggc gcacgaaacc    3300
gacatggtct gggtccacga ctaccacctg ctcctcgcgc ccatgcacat tacgcggaaa    3360
```

-continued

```
gtccgacgcg ccaacgtcgg cttctttctt cacatcccct tccctcttc cgaaatcttc    3420 aggtgtctcc cttgccgaga agacgtgagt cgaaaagaaa aaaacgcgac gcgcgtcaac   3480
acctgcggct gtggcggagc ggtctctgct cggggtgta tgtacacccg aggggcttcc    3540
cggaggtgtg agcaggccag gccgcgaggg cggcctctcc tccgacggcg ttgccatttt   3600
tttgcatgca agcttcagga aacacgcttt cttgccgcgg ctctcggtgc gtctgtctcg   3660
ttcgttcttt gcgttccccg tatcgatcca accaacatgg acagacgccg gttgtgggtc   3720
tgtgtctgtg tgcatgtatg cgcatctagg gacatgcgta tgagacgcaa atgtcttcaa   3780
cttgtattct gagtgcgtcc tgacgccgat gtgtatactg ggcgttgctt cgctgttgcg   3840
ctgtgcaagt cctttgaccg gttcggcggc ttttcctcct tctcttgttc agattttgcg   3900
agggatgctg tgcgcggact tgattgggtt tcacctcttc gagtacgcgc gccactttct   3960
ggtcgcatgc aagcggctgc tcggcctcga gcaccatttt tgtcgagggg gcattctgaa   4020
catcgagtac ggcggccgca acgtctcggt ccgcatcggc catgtccaca ttcagtacgc   4080
cgacattcgc tcgaaaatcg aggcaaaccc ggtggttctg cagatggcgc gagacatcag   4140
gtaaaacaca cggacatcca gagacaggaa agaaagggga aatgggggaa atatgaaaga   4200
cagggctacc ccgctggacg gggctcgatt tcgagaagct ccaggtgtct agacaccgcg   4260
ctttaccgca agtagttgtg ggtgcagaga ccaagttgtg tttcctcttc ccctttggtg   4320
gaaagtgttc gatcctttcc agattccatg cacttctgta tggccgttct gtcgttttcc   4380
aacgacgcct cggcttctct gcggtgtccg tacggcacct gtttcccgag tgctgcgacg   4440
cgttttctct gaacattccg gattttctgg atctccgttt cgcaaaagga atgtggaatt   4500
tttagcctcc ggtgtccgtc gtctctctgc atgcctgttc agacaaaaac acgtcggaaa   4560
attcatcttc gtctccgtgg accgctgcga gaaattggcc ggtctcctcc tcaaagttcg   4620
cgccttccag gcgtttctcg tgacctactc ttatgccagg gtatgttcct tcaaaagcgt   4680
tgtgcgcgca ttgtcctctg ttgttctcaa ccttcttcct ccgtcgcgcc tggacggagg   4740
ctctcccttc gcttcccttt ttctctctct gcttctttac ttccgtcgac gcttgtgtgg   4800
gtgcttggct gtggcttta dacgcgtcgc gcgtgtgaat ggagccgcag agtgtatccg   4860
cgagaaacgc gcatcaatgc gtagcgcgaa ctcgacttcc ttcgaggtcc agcttgagta   4920
gcctccccag caaagggag tttatgtgga cctagacatc ccttgaacat tgcggtcgac   4980
actttcctct cgactccgct gcgttttcag ggaaatgtcg tcctcattca gtacgcgtat   5040
cctaccatca aatacgcaga agacacagaa accatggcga cggaactcaa agagctcgtg   5100
gagaaagtca atgcccagtt cgccttgcca gatcgcccag gtgaggagaa atcgcaggtt   5160 cttttcagt ctgccgaggt ctctgcagcg tgttctttct tgggagca agggcgtctt     5220 ttttcggcaa aaccttctac cgcagtcttg ggtcactggt gcatcttgcc gctgtcgctc   5280
tgcacttgcc gctgtcgctc tgcacttgcc gctgtcgctc tgcacttgcc gttgtcgctc   5340
tgcacttgcc gctgtcgctc tgcacttgtc gttgtcgctc tgcacttgcc gttgtcgagc   5400
tctcccgagt tccgccgaat tccttctct ctcgcgggtc ggctttcctc ttcgcgacag     5460
caaagacaac ggcgctgctc tgctgcctgg gtcgctgtct gtcgaggcgc catgtgaaaa   5520
actcgtcaag aatcattcag tcggtgtctg tgtgtctctc tggggagggg agagggggt   5580 ctcctcatcg gctggccttg tcttctctgc ttgcgcggtc aaagaatcgt ttctctgggg   5640
tcgccagtgc actttgcggg tctcttcgtc tctctggaac ggcctctttt ttcagatttc   5700
```

```
caacatatcg aactccacat ccagccggtc ggctgggagg agaagtgggc gttgtttacc    5760
gcgggcgact gcttccttga cacatcgatc cgagatggcc tgaatctcaa tccgttcgaa    5820
tttatctgtt gccacaaaga caacgtcacc ggtgtgattt tatcagagtt cacggggtgc    5880
agcagagccc tcgcctcggc cattcgcgtc aatccttgga aggtcagttg aaaaagcaag    5940
tcagttgaaa aaacaagaca cacgcgaagc gcgctgagag acaaagggag ttcttctctc    6000
tcgtgccgtc tcctctcttt cgtctcgctc tttcgtcttt ctcctcccct tcttctctgg    6060
ctcgtcttcc gctgtagccg ccactctgcg ttcgtccgct gcgcctctgc aggtggaggc    6120
ggtggcagat gcgatggaca gaatcatcaa catgcctgtg gaggagcagc gcgaccggtt    6180
cacccgcgac cgcgactact tgagtcacaa cagtacgcag aagtgggcag acgaaaacat    6240
tctggatctg cgacgagccc ggaaaccaga cgacttcgtc tacgtctctt ggggtctcgg    6300
caacaccttc cgcgtcctag gcatggactc caacttccgg taagaagagt tgttaggacc    6360
gggggaacgg tcgacggcca aggcaggtcc acgcgacagt gcaacagaga gcggggaagc    6420
tgtcaagggg cgaacgcgtc agctctgctc agccaaagac gcggtcgggg ggccttcggg    6480
ggaagagaaa cgcacatgtg gtattccagc tctttcaaag ccggctgaac aaggtgctct    6540
gatgtgccaa ggacttcgct gtcggcgcgc ggatctgcgt agcgtcttct gccctagatc    6600
gcagcagcag gagtgtcaga gcgccgctgc aggagaacat cggcgaggaa ggaagggcgc    6660
ctggagtcga gtccaagaag gagaagccgc ggcagatccc ggaggaaacg acgaagagca    6720
ggaagggtgc cggcgcgcag agaggaagac agcgagaagg ggcggccgag gccggggaca    6780
gtgtggagaa aatgcgacag agcagtggag aacgggagga gaccagggga tggacaagtc    6840
gagaaggaag tcgaggaaaa ggacagcgag gaatcgacga agaagagagg gggaagggaa    6900
ccaatgcagc gcttttcaag gtttacggca acgaccagtt ctgcggagcg cctgcgattc    6960
gacccttcga actcgagttc tccagaagcg ttttcggact tgttgctgc tcctgttttc      7020 caggtttctg gacacaaatc aagtggtgcg aggctaccga acttctcgac atcgcgtctt    7080
cttcttcgac tgcgaaggca cactcgcgcc ggacagacgc cgaatcactt ttgtacctgg    7140
cggcgaaaat ctttttgcgc aaggtcgccc gccttcgccg caagtcaagg actgtctcca    7200
ggcgcttgtc gacgaccaaa gaaacactgt tgtcattctc tcgggacgcg acagacacct    7260
cctagaggaa tggttctctt ccatcagagg cattggactt tgtgccgaac acggtaaggc    7320
gacagtgtag gtgcttcgac aaatctcgac gtcttccccc ccccctttcc ccccccccc     7380 ccccccacac acacacacac acacatctc acagatacat atgtatatgt atacatatat     7440
atacagttgt gtgcattata cgtacgcata tatatatacg tatgtatgca tatgcatata    7500
aaagcgtaca ctgatgtgcc gtatgcagaa acatagacgt agggatgcat tctgtggttc    7560
acggacatgt gagttgggag acagcgagag gaatcggttt cgttgagggt tcctggaatc    7620
gtcgagagtg agagtttgcg aaggatcggg tggctggatc tgaaaataaa gttttttcga    7680
gttctgcgga agcgaagagc cgtagggtgt cggaaacagg agagattctg caggggaaag    7740
acacacgaga tgcgcggttt ccgaggacac acacctggtc ccttcactca catgcagcat    7800
ctgctagctc ccacaatcca tggtcaatga gactccgttg ataaaagatc ccttccttct    7860
accacttcca cgttaatata tatatattta tatatatata tatatatagg tctatgtgta    7920
gatccgtaga aaggcgtata tgcatgtatc tgcacttttg tgtcggcgtg tatgtaaatg    7980
tatttacaca tacagatcca tgaatctcca tccatacgtt tttgtattta tgtagacata    8040
tatatatata tatatatatg tgtatgtata ggggggagat tgtgtgtttt tttgtcgttt    8100
```

```
gcttgagagg tttgttttca gtgcgttgtg gtgataagag cttttggagt gacctgcggt    8160
tggttttcag gttttactta ccgggttccg ggcatcacgg gggaccagtg gcactgcatg    8220
tctcgtcaaa cagacttcac atggaagcaa gtggcgatcg agctgatgct gcagtatgtg    8280
aagcgaactc agggctcatt catcgaaaac aaagtaggtg aacggtggtt tttctttct    8340
ggaacgtctc ccttgcgtgg acctcacgct ctctcctcga aacgtcgccg cccccgccac    8400
acagagctgc cggcgccttc tctctcctcg actagagaac tcgcaggtcg cggtcgagag    8460
cggagtcgaa gacgagtctc tttttcgctt cagttgcgaa gcgcgtcgtt tctgacttgg    8520
cgtccacgaa gaactggaaa aaacctgtg ctggaacggt tctcaagagt cgaaaaccga    8580
cagttgtgac gcttgggacc cgcaagctga cttccaagtg cgacgcgaag ttcgctgcgt    8640
ttgaacactt gccagttgcg agaggatctc tgtagttcct tgcagacatt tcatgtccgc    8700
cgattccttc tctgcgcttg tgcgcagtct tcttgtcggc agttccttgc ggctggcggt    8760
agaaccgtac caaacacact ggcgtttaca cagagccccg ctgcgtctga ttcaccttgt    8820
gaaggaggag tgcgagggtg gctgttctgg acaagctttt gttcaccgtg acgtccgcct    8880
caaaactccg gaatgcacat cgcagagtcg gattcctgcg tctacagacg ctggcttttc    8940
tcttgtgcat gtgcctccag tcctgctcgg actcgaagct gaatgtgaca acagtgaatt    9000
cttctctcgt tctgctgcag ggaagtgctc tcgtcttcca gtaccgcgac gcagatccgg    9060
atttcggcag catgcaagcc aaggatctct cgaactacct cgggtgagaa actcgcattc    9120
tgcgcgaaca ccctcagcgc ttctcaggct ttgttcgccg catttcttca gacaaggaaa    9180
atgggtcggt gaagggcact gcgtcaggcg ccttcgcctc tcgccttcgg gtgcgcaacg    9240
tgtatcgaaa aggaatctga tttcttttca gggaactgct cttcggctat cctgtctcgg    9300
tcatgagcgg gaaaggctac gtggaagtga aactgcgagg tgtcaacaaa gggcatgcag    9360
tcgagaaagt tctgcggaaa ctcagcaacc tccacggaga cgtcgacttc gttctctgcg    9420
tcggagatga caggtaaaca gaccaatgaa agctgacgaa cgagacgcaa gaaaactcgc    9480
acgtgagcca tctacttcta ctcacgtgaa tacacataca tgcacatgca cacatactac    9540
ctacatatgt atatgcatat atatatatat atatatatat atatgtgcat atatatatat    9600
atatatatgt atatgcgtag agaagtactt gtgcagttct gtgtttgtga gtggatattc    9660
ctgtgcacag aggcgtagcg tttttcatgt gagttttaga agtgaatgta tgctgtttag    9720
tctggagaag gcgtcggctc ttttcagggc gcatacttt gaggaaaggt gagtttcgca    9780
gttgagggaa cgggaagcga gggtgttggc aggacgcgat tgagaagact gcattccaga    9840
ggccttcctt tcttctgaat tttcttcaga agcgacgaag acatgttcgc ggtcatcaac    9900
gccatgacgg aagacgggga ccagctgtgc ctgccagagg gcagcggcgc cgggagcagc    9960
ggcctctatc gccacacaca gtcgaaggat cgaattccta gacgcaactc tgtctctgta   10020
cgcggcgggt cgatgacgca acgcgtcaaa attggggaag cgagctgtcc tcagagatct   10080
gcgtacttct tccacactta cagacgtata catggctttc tgcgcagttg ctgctgtatc   10140
tgtaaatgtt tatgccgctc tttgtccaac atacatatac atatacatat atatatatat   10200
ttatttattt aatatattta atatattgat attataagt gtatatatgt acagaaacgt   10260
tgcagaagtg cgtaggttga tagatgtgtg ccgtgagagg aagaaagccc tgacgtaccg   10320
tgagatgtgt gtcgcgagag tttgaaaaga catacacata tacatatata catatatata   10380
catatatata tatgtatata tatgtatata tatgtatctc gaactgttga gatacacgtc   10440
```

```
tgcataggtg taagtaacta gatgccaata cacagacaac agactttatt tgaatgtgcg    10500
tacatctttt ctctcgcttt cagtcggatg agaaccgagc agaagctgtc gttggaaacg    10560
tggagggact catgaagcgt gacgggtcga tgcagcatgc ggggggcgctc ggcagcggct    10620 tgacctctgc gtcttccagc acaagtctca gtgggcacac aaaggtaaag gaaacaactg    10680
cgggggaagg cgtagaaagg cgagcaggaa ggcgaggagg aagagaagac aaagcgagga    10740
gcgagggaga gaccgaacgc agaaacaagg aggtgacgca aaggaggaga gccgaggag    10800 gaaggaggga cgaacacagg caaaagaag agcagcagaa gggagggaga cgaacagcga    10860
gggagagaag agagcagaca aggagacgat acaacagagg aaagaaagca ggggaagacg    10920
cgcggggcgt accagagaaa gaagaaagga gacaggtacg aagcgaacgg tagggcggag    10980
ggagggagcg agagaagaga aacgagagg agagactcaa ccttgcgttc gaacaaggat     11040
gcagagcacg gagaagaatc gaaagggct gcggagcccg acgatacaaa gaggagaaaa    11100
cagaaacaaa agacagagaa aaagaaacaa gacacaggag cgcagacaca gcatgaggaa    11160
acgaggacgg aagtgatgca agtgtgtatc tctttgttgt gttggaatgt gcagaaaacg    11220
agtcctcact ttttcacatg cacagtcggc aagaagccgt ccaacgctcg gtatgttttt    11280
tttaaaaaac aaagtttctt agagcacttt tccccgcgtt ttcgtctcgt gccgtctcat    11340
ctgcgtcttt ccttctcagc gcattacttc actttcttct tttttttcttt cgttgttcta    11400 atccagtctt cttgcgtgtg tgaatgctgt ctcgtccttc gtctctctcc atgcgtattt    11460
ctgttcctct cttggcccgc agtcgcctcc gtcaggggg aacgcaaacg acgcggcgac    11520
gtggaacgcg aaatgtgcag aaggtgctcc acggtctcca gagttttctg aagtgtgtct    11580
tcaagtttcg ccgaacaacg attcgtgtcg actgttcgga taacttcaaa agacgacgcg    11640
ccatccttgt ttccctcctc tcgtttctgg cttttggcttt ttcgaaatgc ggagtttctc    11700
tgtttcattc gtcttttttgg cccgttctcg atctcttcac aggtattacc tcaacgacac    11760
tgaggatgtc tccgatctcc tcgactctct gcagcagtgc actgagaagg taaacttctt    11820
gcccccagac acactctgtt cgcaggtgga ggcgtccgcc gtgtttttca gtttaatccg    11880
gttcttgcct tgggcctctc cccccccttt gttctacgcc atcggctctc ttcatgcgcg    11940
tcccgtcatg tgccgtcgcg ttctctttgc ggtgtccctc cttctctttc ctcgcttcgt    12000 gtgtgttttct cgtcgttttc tgtggcgtca ccccatcac tggctccctc cctcccatcc    12060
tgtctcttct gctgtcgcgt tctctctctt tttctgtgtt tgttcaatcc gcttgagctt    12120
ttcatctcgc tgcagctgtg ctcggctcgt gtggttctcc aggacgggaa ggagcagtgg    12180
agttcgtcga aggacgcgag ttgcctctcg gcgccagtcg tggcggccgc ggcggctgcg    12240
ggctcgctcg cggggaacgc ggcggtgcag ctgaggaaag gcgacagcgc agcttcgaac    12300
tttgcgagtc tgtggagatc gcctctggga tcaggagcag gtcgcacgag agaacgaacg    12360
ctcgcgcagt gggcggggca ggcaccgagc gccatcttca gtcgcccgt cggtgccgtt    12420 gaagttcgcg ccaacgcagc tggcagcaca gatcgcccaa cagacgagta g              12471
```

<210> SEQ ID NO 2
<211> LENGTH: 200
<212> TYPE: DNA
<213> ORGANISM: Toxoplasma gondii

<400> SEQUENCE: 2

```
atgctgtaca ccagggtttt cttccgtgca gtggttcgga cagacttcgg tgaacgagtc     60
gccgtcgtcg ggtcttcccc gtctctgggg aattggcagg tgaggctgcg tcgccgtcgc    120
```

```
ctgcgccgct tcgtgacacg gcgaacggtc gaaatgacaa gggaaaaccg ttcgttagga      180
aaaaccgttc gttctgaggc                                                  200

<210> SEQ ID NO 3
<211> LENGTH: 3666
<212> TYPE: DNA
<213> ORGANISM: Toxoplasma gondii

<400> SEQUENCE: 3
atgctgtaca ccagggtttt cttccgtgca gtggttcgga cagacttcgg tgaacgagtc       60
gccgtcgtcg ggtcttcccc gtctctgggg aattggcagg ctgaacacgg ccatgagctg      120
accacaaacg aggatgtctt cccttcgtgg ttctccaagg agcctgtcta cttgccgcta      180
aagaaaccca tcttacaa atatgttgtt ctcgacgaac gcggcgacat cgtgaggtgg        240
gaagaatgcg agggaaatcg cgagttggtg cccacgggct ggagatgac ggtggaggat       300 gacgatggcc tttttaggga gcagatgacg aatcgcggcg accacggagt cgaaggcgat      360
gacgacgtgt ctgtggcggc tctggacaag gaggaggtgg acgcgcgcaa ccggatgctg      420
gcgattcaag aagaagagcc tgagttcgac gagaacgaca cgtaattgt gtgtgctctt       480 gacttgcctc tgcgcgtggt gcgtgtctcg ccgtctcgtg aggcttctcc gctgccctcc      540
tctctgcccg cgtcgtcgac cgactcttcc ggccaaacag aaaagcgcgc ggtttcattc      600
ccggaagacg cgggcgcgag tgcccggcgc tcgagttcga ccgtcgcggc gactcgggag      660
gaggaaacga ctcgcactgc gagttccttt ccaaaagtcg aggagacggc ggagagagga      720
cgcgacagct ctctcgctct ttggcctggc gcagcgcgcg acgctgccgg cgacttcggg      780
gaggcgcttc agccgcgcgc gacgcgcagc cgacgaggca cctttgaagt gaggccgagc      840
aagagcgcgt tgttgccttc gctgtttcac ctgaggaaga agacgcggct gcctgtgcgt      900
ttcgtcgggt ggccgggcat ccacgtcgag aacgaagagg agcaggcgga gattgcggag      960
ctgctgcgag cctacgactg ttcgccgatc ttcccagaca aagacgagtt cgactgccat     1020
ctcaccttct gccatcaggt cctgtggccg ctgtttcaca acgtcgtcgt ccttgactcc     1080
aatacccagg tcccgttcga ctccgacctc tgggccaagt accaggctgt gaacaaactg     1140
tgggcggacg cggtgctccg ccaggcgcac gaaaccgaca tggtctgggt ccacgactac     1200
cacctgctcc tcgcgcccat gcacattacg cggaaagtcc gacgcgccaa cgtcggcttc     1260
tttcttcaca tccccttccc ctcttccgaa atcttcaggt gtctcccttg ccgagacatt     1320
ttgcgaggga tgctgtgcgc ggacttgatt gggtttcacc tcttcgagta cgcgcgccac     1380
tttctggtcg catgcaagcg gctgctcggc ctcgagcacc atttttgtcg aggggggcatt    1440 ctgaacatcg agtacggcgg ccgcaacgtc tcggtccgca tcggccatgt ccacattcag     1500
tacgccgaca ttcgctcgaa atcgaggca aacccggtgg ttctgcagat ggcgcgagac     1560
atcagacaaa aacacgtcgg aaaattcatc ttcgtctccg tggaccgctg cgagaaattg     1620
gccggtctcc tcctcaaagt tcgcgccttc caggcgtttc tcgtgaccta ctcttatgcc     1680
aggggaaatg tcgtcctcat tcagtacgcg tatcctacca tcaaatacgc agaagacaca     1740
gaaaccatgg cgacggaact caaagagctc gtggagaaag tcaatgccca gttcgccttg     1800
ccagatcgcc cagatttcca acatatcgaa ctccacatcc agccggtcgg ctgggaggag     1860
aagtgggcgt tgtttaccgc gggcgactgc ttccttgaca catcgatccg agatggcctg     1920
aatctcaatc cgttcgaatt tatctgttgc cacaaagaca acgtcaccgg tgtgatttta     1980
```

```
tcagagttca cggggtgcag cagagccctc gcctcggcca ttcgcgtcaa tccttggaag    2040
gtggaggcgg tggcagatgc gatggacaga atcatcaaca tgcctgtgga ggagcagcgc    2100
gaccggttca cccgcgaccg cgactacttg agtcacaaca gtacgcagaa gtgggcagac    2160
gaaaacattc tggatctgcg acgagcccgg aaaccagacg acttcgtcta cgtctcttgg    2220
ggtctcggca acaccttccg cgtcctaggc atggactcca acttccggtt tctggacaca    2280
aatcaagtgg tgcgaggcta ccgaacttct cgacatcgcg tcttcttctt cgactgcgaa    2340
ggcacactcg cgccggacag acgccgaatc acttttgtac ctggcggcga aaatctttt    2400 gcgcaaggtc gcccgccttc gccgcaagtc aaggactgtc tccaggcgct tgtcgacgac    2460
caaagaaaca ctgttgtcat tctctcggga cgcgacagac acctcctaga ggaatggttc    2520
tcttccatca gaggcattgg actttgtgcc gaacacggtt tttactaccg ggttccgggc    2580
atcacggggg accagtggca ctgcatgtct cgtcaaacag acttcacatg gaagcaagtg    2640
gcgatcgagc tgatgctgca gtatgtgaag cgaactcagg gctcattcat cgaaaacaaa    2700
ggaagtgctc tcgtcttcca gtaccgcgac gcagatccgg atttcggcag catgcaagcc    2760
aaggatctct cgaactacct cggggaactg ctcttcggct atcctgtctc ggtcatgagc    2820
gggaaaggct acgtggaagt gaaactgcga ggtgtcaaca aagggcatgc agtcgagaaa    2880
gttctgcgga aactcagcaa cctccacgga gacgtcgact cgttctctg cgtcggagat    2940 gacagaagcg acgaagacat gttcgcggtc atcaacgcca tgacgaagga cggggaccag    3000
ctgtgcctgc cagagggcag cggcgccggg agcagcggcc tctatcgcca cacacagtcg    3060
aaggatcgaa ttcctagacg caactctgtc tcttcggatg agaaccgagc agaagctgtc    3120
gttggaaacg tggagggact catgaagcgt gacgggtcga tgcagcatgc gggggcgctc    3180
ggcagcggct tgacctctgc gtcttccagc acaagtctca gtgggcacac aaagaaaacg    3240
agtcctcact ttttcacatg cacagtcggc aagaagccgt ccaacgctcg gtattacctc    3300
aacgacactg aggatgtctc cgatctcctc gactctctgc agcagtgcac tgagaaggac    3360
gggaaggagc agtggagttc gtcgaaggac gcgagttgcc tctcggcgcc agtcgtggcg    3420
gccgcggcgg ctgcgggctc gctcgcgggg aacgcggcgg tgcagctgag gaaaggcgac    3480
agcgcagctt cgaactttgc gagtctgtgg agatcgcctc tgggatcagg agcaggtcgc    3540
acgagagaac gaacgctcgc gcagtgggcg gggcaggcac cgagcgccat cttcagtcgc    3600
cccgtcggtg ccgttgaagt tcgcgccaac gcagctggca gcacagatcg cccaacagac    3660
gagtag                                                               3666
```

<210> SEQ ID NO 4
<211> LENGTH: 44
<212> TYPE: DNA
<213> ORGANISM: Artificial Sequence
<220> FEATURE:
<223> OTHER INFORMATION: proto-spacer sequence, PAM motif and N-terminal
      sequence of WT T. gondii targeted by CRISPR

<400> SEQUENCE: 4

```
cccgtctctg gggaattggc aggtgaggct gcgtcgccgt cgcc                      44
```

<210> SEQ ID NO 5
<211> LENGTH: 44
<212> TYPE: DNA
<213> ORGANISM: Artificial Sequence
<220> FEATURE:
<223> OTHER INFORMATION: T. gondii mutant

```
<400> SEQUENCE: 5
cccgtctctg gggaattcgg caggtgaggc tgcgtcgccg tcgc                    44

<210> SEQ ID NO 6
<211> LENGTH: 43
<212> TYPE: DNA
<213> ORGANISM: Artificial Sequence
<220> FEATURE:
<223> OTHER INFORMATION: T. gondii mutant
<220> FEATURE:
<221> NAME/KEY: misc_feature
<222> LOCATION: (17)..(17)
<223> OTHER INFORMATION: n is a sequence of 181 heterologous nucleotides
<220> FEATURE:
<221> NAME/KEY: misc_feature
<222> LOCATION: (17)..(17)
<223> OTHER INFORMATION: n is a sequence of 182 heterologous nucleotides

<400> SEQUENCE: 6
cccgtctctg gggaaanggc aggcaggtga ggctgcgtcg ccg                     43

<210> SEQ ID NO 7
<211> LENGTH: 43
<212> TYPE: DNA
<213> ORGANISM: Artificial Sequence
<220> FEATURE:
<223> OTHER INFORMATION: T. gondii mutant

<400> SEQUENCE: 7
cccgtctctg gggaatggca ggtgaggctg cgtcgccgtc gcc                     43

<210> SEQ ID NO 8
<211> LENGTH: 38
<212> TYPE: DNA
<213> ORGANISM: Artificial Sequence
<220> FEATURE:
<223> OTHER INFORMATION: T. gondii mutant
<220> FEATURE:
<221> NAME/KEY: misc_feature
<222> LOCATION: (21)..(21)
<223> OTHER INFORMATION: n is sequence of >1000 heterologous nucleotides

<400> SEQUENCE: 8
cccgtctctg gggaatttga nttaggcagg tgaggctg                           38

<210> SEQ ID NO 9
<211> LENGTH: 39
<212> TYPE: DNA
<213> ORGANISM: Artificial Sequence
<220> FEATURE:
<223> OTHER INFORMATION: T. gondii mutant

<400> SEQUENCE: 9
gacagacttc ggtgaacgag tcgcctgcgc cgcttcgtg                          39

<210> SEQ ID NO 10
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 10
gggaattggc gttttagagc tagaaatagc aag                                33

<210> SEQ ID NO 11
<211> LENGTH: 31
```

<212> TYPE: DNA
<213> ORGANISM: Artificial Sequence
<220> FEATURE:
<223> OTHER INFORMATION: oligonucleotide primer

<400> SEQUENCE: 11
cagagacggg caacttgaca tccccattta c                              31

<210> SEQ ID NO 12
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 12
atgctgtaca ccagggtttt cttcc                                     25

<210> SEQ ID NO 13
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 13
gatgcagact ctacgagaca ggcac                                     25

<210> SEQ ID NO 14
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 14
ctcagatcta ctttcccgag aggaagagtg                                30

<210> SEQ ID NO 15
<211> LENGTH: 80
<212> TYPE: DNA
<213> ORGANISM: Artificial Sequence
<220> FEATURE:
<223> OTHER INFORMATION: oligonucleotide primer

<400> SEQUENCE: 15
ttcctaggtc ctgctccagc agcgtagtcc gggacatcgt acgggtatcc tgcaccagcg    60
ttcacatctg cgatcagagc                                               80

<210> SEQ ID NO 16
<211> LENGTH: 59
<212> TYPE: DNA
<213> ORGANISM: Artificial Sequence
<220> FEATURE:
<223> OTHER INFORMATION: oligonucleotide primer

<400> SEQUENCE: 16
ggtcttcccc gtctctgggg aattgactag ctgagcaggt gaggctgcgt cgccgtcgc     59

<210> SEQ ID NO 17
<211> LENGTH: 59
<212> TYPE: DNA
<213> ORGANISM: Artificial Sequence
<220> FEATURE:
<223> OTHER INFORMATION: oligonucleotide primer

```
<400> SEQUENCE: 17
gcgacggcga cgcagcctca cctgctcagc tagtcaattc cccagagacg gggaagacc        59

<210> SEQ ID NO 18
<211> LENGTH: 220
<212> TYPE: DNA
<213> ORGANISM: Artificial Sequence
<220> FEATURE:
<223> OTHER INFORMATION: sequence of portion of TPS/TPP-like gene with
      protospacer, PAM motif and insert sequence

<400> SEQUENCE: 18
cccgtctctg gggaaagccg gcgaacgtgg cgagaaagga agggaagaaa gcgaaaggag        60
cgggcgctag ggcgctggca agtgtagcgg tcacgctgcg cgtaaccacc acacccgccg       120
cgcttaatgc gccgctacag ggcgcgtccc attcgcctcg ggggagccct tcagcttctc       180
atagtggctg gccaggtagg caggtgaggc tgcgtcgccg                              220

<210> SEQ ID NO 19
<211> LENGTH: 1045
<212> TYPE: DNA
<213> ORGANISM: Artificial Sequence
<220> FEATURE:
<223> OTHER INFORMATION: sequence of portion of TPS/TPP-like gene with
      protospacer and PAM sequence and partial sequence of insert
      sequence
<220> FEATURE:
<221> NAME/KEY: misc_feature
<222> LOCATION: (473)..(473)
<223> OTHER INFORMATION: n is a, c, t or g
<220> FEATURE:
<221> NAME/KEY: misc_feature
<222> LOCATION: (479)..(479)
<223> OTHER INFORMATION: n is a, c, t or g
<220> FEATURE:
<221> NAME/KEY: misc_feature
<222> LOCATION: (483)..(483)
<223> OTHER INFORMATION: n is a, c, t or g
<220> FEATURE:
<221> NAME/KEY: misc_feature
<222> LOCATION: (486)..(487)
<223> OTHER INFORMATION: n is a, c, t or g
<220> FEATURE:
<221> NAME/KEY: misc_feature
<222> LOCATION: (493)..(494)
<223> OTHER INFORMATION: n is a, c, t or g
<220> FEATURE:
<221> NAME/KEY: misc_feature
<222> LOCATION: (498)..(499)
<223> OTHER INFORMATION: n is a, c, t or g
<220> FEATURE:
<221> NAME/KEY: misc_feature
<222> LOCATION: (507)..(508)
<223> OTHER INFORMATION: n is a, c, t or g
<220> FEATURE:
<221> NAME/KEY: misc_feature
<222> LOCATION: (510)..(510)
<223> OTHER INFORMATION: n is a, c, t or g
<220> FEATURE:
<221> NAME/KEY: misc_feature
<222> LOCATION: (512)..(512)
<223> OTHER INFORMATION: n is a, c, t or g
<220> FEATURE:
<221> NAME/KEY: misc_feature
<222> LOCATION: (514)..(514)
<223> OTHER INFORMATION: n is a, c, t or g
<220> FEATURE:
<221> NAME/KEY: misc_feature
<222> LOCATION: (525)..(526)
<223> OTHER INFORMATION: n is a, c, t or g
<220> FEATURE:
<221> NAME/KEY: misc_feature
<222> LOCATION: (530)..(530)
```

```
<223> OTHER INFORMATION: n is a, c, t or g
<220> FEATURE:
<221> NAME/KEY: misc_feature
<222> LOCATION: (545)..(545)
<223> OTHER INFORMATION: n is a, c, t or g
<220> FEATURE:
<221> NAME/KEY: misc_feature
<222> LOCATION: (547)..(548)
<223> OTHER INFORMATION: n is a, c, t or g
<220> FEATURE:
<221> NAME/KEY: misc_feature
<222> LOCATION: (563)..(565)
<223> OTHER INFORMATION: n is a, c, t or g
<220> FEATURE:
<221> NAME/KEY: misc_feature
<222> LOCATION: (576)..(576)
<223> OTHER INFORMATION: n is a, c, t or g
<220> FEATURE:
<221> NAME/KEY: misc_feature
<222> LOCATION: (580)..(581)
<223> OTHER INFORMATION: n is a, c, t or g
<220> FEATURE:
<221> NAME/KEY: misc_feature
<222> LOCATION: (596)..(596)
<223> OTHER INFORMATION: n is a, c, t or g
<220> FEATURE:
<221> NAME/KEY: misc_feature
<222> LOCATION: (624)..(624)
<223> OTHER INFORMATION: n is a, c, t or g
<220> FEATURE:
<221> NAME/KEY: misc_feature
<222> LOCATION: (626)..(628)
<223> OTHER INFORMATION: n is a, c, t or g
<220> FEATURE:
<221> NAME/KEY: misc_feature
<222> LOCATION: (631)..(631)
<223> OTHER INFORMATION: n is a, c, t or g
<220> FEATURE:
<221> NAME/KEY: misc_feature
<222> LOCATION: (634)..(634)
<223> OTHER INFORMATION: n is a, c, t or g
<220> FEATURE:
<221> NAME/KEY: misc_feature
<222> LOCATION: (645)..(647)
<223> OTHER INFORMATION: n is a, c, t or g
<220> FEATURE:
<221> NAME/KEY: misc_feature
<222> LOCATION: (658)..(658)
<223> OTHER INFORMATION: n is a, c, t or g
<220> FEATURE:
<221> NAME/KEY: misc_feature
<222> LOCATION: (676)..(677)
<223> OTHER INFORMATION: n is a, c, t or g
<220> FEATURE:
<221> NAME/KEY: misc_feature
<222> LOCATION: (687)..(687)
<223> OTHER INFORMATION: n is a, c, t or g
<220> FEATURE:
<221> NAME/KEY: misc_feature
<222> LOCATION: (701)..(701)
<223> OTHER INFORMATION: n is a, c, t or g
<220> FEATURE:
<221> NAME/KEY: misc_feature
<222> LOCATION: (726)..(726)
<223> OTHER INFORMATION: n is a, c, t or g
<220> FEATURE:
<221> NAME/KEY: misc_feature
<222> LOCATION: (739)..(741)
<223> OTHER INFORMATION: n is a, c, t or g
<220> FEATURE:
<221> NAME/KEY: misc_feature
<222> LOCATION: (776)..(776)
<223> OTHER INFORMATION: n is a, c, t or g
<220> FEATURE:
<221> NAME/KEY: misc_feature
<222> LOCATION: (801)..(803)
<223> OTHER INFORMATION: n is a, c, t or g
<220> FEATURE:
<221> NAME/KEY: misc_feature
```

```
<222> LOCATION: (822)..(824)
<223> OTHER INFORMATION: n is a, c, t or g
<220> FEATURE:
<221> NAME/KEY: misc_feature
<222> LOCATION: (839)..(841)
<223> OTHER INFORMATION: n is a, c, t or g
<220> FEATURE:
<221> NAME/KEY: misc_feature
<222> LOCATION: (885)..(885)
<223> OTHER INFORMATION: n is a, c, t or g
<220> FEATURE:
<221> NAME/KEY: misc_feature
<222> LOCATION: (887)..(887)
<223> OTHER INFORMATION: n is a, c, t or g
<220> FEATURE:
<221> NAME/KEY: misc_feature
<222> LOCATION: (899)..(900)
<223> OTHER INFORMATION: n is a, c, t or g
<220> FEATURE:
<221> NAME/KEY: misc_feature
<222> LOCATION: (917)..(918)
<223> OTHER INFORMATION: n is a, c, t or g
<220> FEATURE:
<221> NAME/KEY: misc_feature
<222> LOCATION: (920)..(920)
<223> OTHER INFORMATION: n is a, c, t or g
<220> FEATURE:
<221> NAME/KEY: misc_feature
<222> LOCATION: (922)..(922)
<223> OTHER INFORMATION: n is a, c, t or g
<220> FEATURE:
<221> NAME/KEY: misc_feature
<222> LOCATION: (927)..(927)
<223> OTHER INFORMATION: n is a, c, t or g
<220> FEATURE:
<221> NAME/KEY: misc_feature
<222> LOCATION: (952)..(952)
<223> OTHER INFORMATION: n is a, c, t or g
<220> FEATURE:
<221> NAME/KEY: misc_feature
<222> LOCATION: (959)..(959)
<223> OTHER INFORMATION: n is a, c, t or g
<220> FEATURE:
<221> NAME/KEY: misc_feature
<222> LOCATION: (986)..(986)
<223> OTHER INFORMATION: n is a, c, t or g
<220> FEATURE:
<221> NAME/KEY: misc_feature
<222> LOCATION: (1005)..(1005)
<223> OTHER INFORMATION: n is a, c, t or g
<220> FEATURE:
<221> NAME/KEY: misc_feature
<222> LOCATION: (1008)..(1008)
<223> OTHER INFORMATION: n is a, c, t or g

<400> SEQUENCE: 19
gtcgggtctt ccccgtctct ggggaatttg acgcgcctcc tgcagaacgc gagacactgg      60
gatatgtaga gccaaggggg aaaccttcga actctcgaat gtcttctctg acaagaatca     120
tatttccatc agttctgtca gattttcaaa tggcgacctg cagaggcctg cttcctccct     180
gtgcgctctt cgaaggggct ttctgtcgcg caggtaact gagttgttcc gttgtggctt      240
gcaggtgtca catccacaaa aaccggccga ctctaaatag gagtgtttcg cagcaagcag     300
cgaaagttta tgactgggtc cgaatctctg aacggatgtg tggcggacct ggctgatgtt     360
gatcgccgtc gacacacgcg ccagtcgcaa cgaccagtct ttgaagctgc acgcacatga     420
aatcacggac cgtggaaaag gcaacggatg taaaacttat tccataccg tcnacctcna      480 ggnggnnccc ggnnccccnt tcgcccnntn gngngtcgta ttgcnttcn ctggccgtcg      540 ttttncnncg tcgtgcctgg gannnccctg gcgttnccn ncttggtcgc cttgcngcgc      600 gtccccctt cgccggctgg cgtntnnnct naagggcccg ctccnncgc ccttcccngc       660
```

```
tcttgcgctt cctgtnnggc ctgctgncac gtctccctgt ntgcggcgct gttcgtcgcg      720
gccgcntcgt ggttgtgtnn ngcctccccc ggtgtcccgg ctccctttg cccttngccc       780 ttgtgcgccc cgcgtcccctt nnngccttc cttttccttt tnnnttttcc ccgccctgnn      840
ntcttgcttt gccttttgcc tctggcctcc cgttcctggc ttttntntcc cccgcgccnn      900
ctttccgctg ttcccgnncn tnctccnctg ccttttttcc ctggccgccc gncgcgccnt     960
ccgctgcgcc ccggttttcg ctctcntggg tctcgcctgg ggttngcntg acggtatcga     1020
taagctttta ggcaggtgag gctgc                                            1045

<210> SEQ ID NO 20
<211> LENGTH: 48
<212> TYPE: PRT
<213> ORGANISM: Artificial Sequence
<220> FEATURE:
<223> OTHER INFORMATION: Modified C-terminus of hexokinase

<400> SEQUENCE: 20

Ala Asp Val Asn Ala Gly Ala Gly Tyr Pro Tyr Asp Val Pro Asp Tyr
1               5                   10                  15

Ala Ala Gly Ala Gly Pro Arg Ala Gly Ala Gly Tyr Pro Tyr Asp Val
            20                  25                  30

Pro Asp Tyr Ala Ala Gly Ala Gly Pro Gly Asp Val Asp Ile Glu Leu
        35                  40                  45

<210> SEQ ID NO 21
<211> LENGTH: 58
<212> TYPE: DNA
<213> ORGANISM: Artificial Sequence
<220> FEATURE:
<223> OTHER INFORMATION: deleted sequence from SEQ ID NO:9

<400> SEQUENCE: 21
gtcgccgtcg tcgggtcttc cccgtctctg gggaattggc aggtgaggct gcgtcgcc        58

<210> SEQ ID NO 22
<211> LENGTH: 20
<212> TYPE: DNA
<213> ORGANISM: Artificial Sequence
<220> FEATURE:
<223> OTHER INFORMATION: protospacer sequence

<400> SEQUENCE: 22
cccgtctctg gggaattggc                                                  20

<210> SEQ ID NO 23
<211> LENGTH: 3277
<212> TYPE: DNA
<213> ORGANISM: Toxoplasma gondii

<400> SEQUENCE: 23
atgcagcctc gtcaaccagg cgacgaagcg aagcagctcg cggagctgga ggtgtggaca      60
tcacagctgg gtcgacgggg accataaaat ctgtgtaatt tcgtccgtgt gcagtgtggg     120
tgtgtacgta ggttatgcac acatttgagt tgatgctgat ttgcacgaat agcgctgcat    180
tttggcgcct tgtgtaaatg cgccgggaaa aatacgtcaa aatgtcctat ttttcgtccc     240
tggtgctgcc acctcgggaa tgtttcctgg gcattcgaag atgcacggtg gaaaaatggt     300
cgtacctact tcccccgatg aagtgcaagt ccgttggagc ctcgtatttg tgtgtggcag     360
ggtttgtgtg acaagcagct gcccaaaagc tgccttgatt tcagcacgaa caacttgggt    420
```

-continued

```
ctctcgtgcg acgcgaagca gtagcgagaa acctgagttt accggggagc ggggagtgac    480
aaatgtgaga tttctgagca catgcgggcc cgggaaagag cttttttta gcatgcaacg     540
attctgtgtg acaggccaaa gaacaacagt cctatctttt ccaattccat gtccgctcag    600
gtcgttcgcc aaatgatgac cccgacacgc gaggttctgc tggagctgca cgaaagcttt    660
ttgaaggagc tacaacgcgt gagtattgtg gcctctgttt gacaaattgc tatttcgttt    720
caaggagtaa ctttcagtgg tgggaaggcc gtgcactacc atgctcttgc ctctctagca    780
accccgttt acacttttgt ctctgtgaaa tgatcgaagc gagagagaat ttcgttttca     840
agcgtcacgg tactgacagt cttcagaac ggaggtggga tgactgtacc gtctggttgc     900
atgacactcg tgcaagaagg ccgttgctgt tcttgtgcgt tcgctctcgg tgtcttctcg    960
gttgtgcata tttgctgttt gttcgaagct ctctccgctt cttcgcctgc ctcgctttcg   1020
ggcgcacgag acagcttcgc cttcatctcc atttcgtcgt ctgaaactgg attttgcgct   1080
cagggcttgg aaatgcacaa agacacggc atcacatggg tgcctgagga atgctcgatg    1140
aaaatgctgg acagctgcgt gtcgaatctg ccgactggtg ccgaagttgg cgaggcatat   1200
gccatcgact tcggaggctc gacatgccgg gctgttcgtt gttctcttct tggcaagggc   1260
aaaatggaaa ttattcaaga caaaatctgg taagcacact ttaacgaatg gcgttggacg   1320
ctgtcgctag ctgccggttt gttgagagcg aacgagaagc tggcgagcct gtcatcgtgg   1380
tgctcaatgt gtgctttgct ttgcgtgttt acgtacagcc tgagaagcgc ggaacatcga   1440
tgcgccaagg gattcatgga caagaaggca ggaggcaaag aactgttcga ccaattcgcc   1500
atgtgcatcc gcggcctgat ggataggtcc ggagacctga agaaggcgga agagaccaac   1560
acacctgtcc cagttggatt cactttctct tttccttgcg cccaagcggt gagttttgg    1620
aatcgtaaaa cagagcacta ttgggtcctc gatgtcggta actttcccga gaggaagagt   1680
gagggaacga cactttgctg acatttcttc aggaactggc aaggccacaa atgcggcgaa   1740
aggtggaagc cgggtttctg atgtcgtgac tcatacactt cgagaaagcc atcgatttgt   1800
gtttccaggc gttgaactct agctttctca ttgagtggac aaagggcttc gaaactggcc   1860
gcgagaaccc ggatcgtgta gaaggcaaag atgtggcagt gttgcttgcc gatgcactgc   1920
aacgtcataa cgttcctgct gtctgcaagg ctatcgtgaa cgacacggta agcacatttt   1980
acgtggaagc gtgagagacc atggttgtgt ccgaaggcat aactagccgt gcagcgatgg   2040
ctcccttgat gtgcgcatcc acgcgggagt attctttttt tctgctgact atagtctgtt   2100
gagtgggaaa gcggtgagcc gctcactgtg aaacccgtct ttggacttcg cttgcctctg   2160
tcaggttggc acattggtgt cttgcgcata tcaaagagtg ccaggcactc cggagtgccg   2220
tgttggactc atcatcggca ccgggttcaa cgcgtgctac gtggaacctg aagctagcaa   2280
ctatggctac acgggtaccg tcgtgaatat ggaggcaggc aacttccaca aggatcttcc   2340
gcgcaacgaa atcgacgtcg aggtgggtct gtggtgatgc aggatctgga agattaactc   2400
tccttgcgca catgcaagag ttggtgtttc ttttgaggac ggtatatgag gtgcagttat   2460
gggcgctcaa ttaggctatc ctgttacatt tgttctctgc gttcaggtcg atgagaagac   2520
acacaacaga ggcaaacagc aattcgagaa actcgtgtcg ggctactaca tcggcgaaat   2580
cgtccgggtc gctgcagtca gagtatttgg cgcccgtgcc cccgagaaag caaggtaaac   2640
aatcttctgt gtggatgttg aaggctgctg ggcgaatcct tgggttctta gacaccgcga   2700
cacgattcc ccgaataaca caacttccgg ttactgctgt gtatgtgttt ctcagtgtca    2760
gacactcgat tcatggtgaa acggcctcga cgatccgtga tgaccatagc caggacaaag   2820
```

```
ccgccagcat tcaggctatc aaggagtgct ggggtgtgac gatggacttg gacgacatca    2880
agtgcatctg ggagatttgc cgactcgtct tcgaccgctc agccgcgttc gctgcaacgc    2940
tggcggtcgc tctgtgctac cgaacagggg taagttccgt agtaactaaa attttttcca    3000
aactatcccg gcgcattcag ttctgatttt ttcccgttca ggcgcgattc ctaaacgagg    3060
tggacgctgt gattctgctt gtgctgttgt gcagcgactt gacaccggat ccaccgtagg    3120
aattgatggt gctttgtatg tgaagaacca gtggtaccgg gaggctgttg agtactacac    3180
aaaattggtc gccggcgacg cggcgaaaaa cattcactac tgcattgcgg atgacggctc    3240
tggcaagggt gctgctctga tcgcagatgt gaactga                             3277

<210> SEQ ID NO 24
<211> LENGTH: 1789
<212> TYPE: DNA
<213> ORGANISM: Artificial Sequence
<220> FEATURE:
<223> OTHER INFORMATION: gBlock 1 sequence

<400> SEQUENCE: 24
catatagatc tatgctgtac accagggttt tcttccgtgc agtggttcgg acagacttcg      60
gtgaacgagt cgccgtcgtc gggtcttccc cgtctctggg gaattggcag gctgaacacg     120
gccatgagct gaccacaaac gaggatgtct tcccttcgtg gttctccaag gagcctgtct     180
acttgccgct aaagaaaccc atatcttaca aatatgttgt tctcgacgaa cgcggcgaca     240
tcgtgaggtg ggaagaatgc gagggaaatc gcgagttggt gcccacgggc ttggagatga     300
cggtggagga tgacgatggc ctttttaggg agcagatgac gaatcgcggc gaccacggag     360
tcgaaggcga tgacgacgtg tctgtggcgg ctctggacaa ggaggaggtg gacgcgcgca     420
accggatgct ggcgattcaa gaagaagagc ctgagttcga cgagaacgac agcgtaattg     480
tgtgtgctct tgacttgcct ctgcgcgtgg tgcgtgtctc gccgtctcgt gaggcttctc     540
cgctgccctc ctcgctgcct cgtcgtcgac ccgactcttc cggccaaaca gaaaagcgag     600
cggtttcatt cccggaagac gcgggagcga gtgcacggcg ctcgagttcg accgtcgcgg     660
caactcggga ggaggaaacg actcgcactg cgagttcctt tcctaaagtc gaggagacgg     720
cggaaagagg acgagacagc tcgctcgctc tttggcctgg cgcagcacgc gacgctgccg     780
gcgacttcgg ggaggcgctt cagccgagag cgacccgcag ccgacgaggc acctttgaag     840
tgaggccgag caagagcgcg ttgcttcctt cgctgtttca cctgcgcaag aagacgcggc     900
tgcctgtgcg tttcgtcggg tggccgggaa tccacgtcga gaacgaagag gagcaggcgg     960
agattgcgga gctgctgcga gcctacgact gttcgccgat cttcccagac aaagacgagt    1020
tcgactgcca tctcacccttc tgccatcagg tcctgtggcc gctgtttcac aacgtcgtcg    1080
tccttgactc caatacccag gtccgttcg actccgacct ctgggccaag taccaggctg    1140
tgaacaaact gtgggcggac gcggtgctcc gccaggcgca cgaaaccgac atggtctggg    1200
tccacgacta ccacctgctc ctcgcgccca tgcacattac gcggaaagtc cgacgcgcca    1260
acgtcggctt ctttcttcac atcccccttcc cctcttccga aatcttcagg tgtctcccctt    1320 gccgagaaga catttttgcga gggatgctgt gcgcggactt gattgggttt cacctcttcg    1380
agtacgcgcg ccactttctg gtcgcatgca agcggctgct cggcctcgag caccattttt    1440
gtcgaggggg cattctgaac atcgagtacg cggccgcaa cgtctcggtc cgcatcggcc    1500
atgtccacat tcagtacgcc gacattcgct cgaaaatcga ggcaaacccg gtggttctgc    1560
```

```
agatggcgcg agacatcaga caaaaacacg tcggaaaatt catcttcgtc tccgtggacc    1620
gctgcgagaa attggccggt ctcctcctca aagttcgcgc cttccaggcg tttctcgtga    1680
cctactctta tgccagggga aatgtcgtcc tcattcagta cgcgtatcct accatcaaat    1740
acgcagaaga cacagaaacc atggcgacgg aactcaaaga gctcgtgga               1789
```

<210> SEQ ID NO 25
<211> LENGTH: 1915
<212> TYPE: DNA
<213> ORGANISM: Artificial Sequence
<220> FEATURE:
<223> OTHER INFORMATION: gBlock 2 sequence

<400> SEQUENCE: 25

```
ctcaaagagc tcgtggagaa agtcaatgcc cagttcgcct tgccagatcg cccagatttc      60
caacatatcg aactccacat ccagccggtc ggctgggagg agaagtgggc gttgtttacc     120
gcgggcgact gcttccttga cacatcgatc cgagatggcc tgaatctcaa tccgttcgaa     180
tttatctgtt gccacaaaga caacgtcacc ggtgtgattt atcagagtt cacggggtgc     240 agcagagccc tcgcctcggc cattcgcgtc aatccttgga aggtggaggc ggtggcagat     300
gcgatggaca gaatcatcaa catgcctgtg gaggagcagc gcgaccggtt cacccgcgac     360
cgcgactact gagtcacaa cagtacgcag aagtgggcag acgaaaacat tctggatctg     420
cgacgagccc ggaaaccaga cgacttcgtc tacgtctctt ggggtctcgg caacaccttc     480
cgcgtcctag gcatggactc caacttccgg tttctggaca caaatcaagt ggtgcgaggc     540
taccgaactt ctcgacatcg cgtcttcttc ttcgactgcg aaggcacact cgcgccggac     600
agacgccgaa tcacttttgt acctggcggc gaaaatcttt ttgcgcaagg tcgcccgcct     660
tcgccgcaag tcaaggactg tctccaggcg cttgtcgacg accaaagaaa cactgttgtc     720
attctctcgg gacgcgacag acacctccta gaggaatggt tctcttccat cagaggcatt     780
ggactttgtg ccgaacacgg ttttactac cgggttccgg gcatcacggg gaccagtgg      840 cactgcatgt ctcgtcaaac agacttcaca tggaagcaag tggcgatcga gctgatgctg     900
cagtatgtga agcgaactca gggctcattc atcgaaaaca aaggaagtgc tctcgtcttc     960
cagtaccgcg acgcagatcc ggatttcggc agcatgcaag ccaaggatct ctcgaactac    1020
ctcggggaac tgctcttcgg ctatcctgtc tcggtcatga gcgggaaagg ctacgtggaa    1080
gtgaaactgc gaggtgtcaa caagggcat gcagtcgaga aagttctgcg aaactcagc     1140 aacctccacg gagacgtcga cttcgttctc tgcgtcggag atgacagaag cgacgaagac    1200
atgttcgcgg tcatcaacgc aatgacggaa gacggagacc agctgtgcct gccagagggc    1260
agcggagccg gcagcagcgg cctctatcgc cacacgcagt cgaaggatcg aattcctaga    1320
cgcaactctg tcagttcgga tgagaatcga gcagaagctg tcgttggaaa cgtcaagga     1380 ctcatgaagc gtgacggctc gatgcaacac gcaggagcac tgggatctgg attgacgagt    1440
gcatcgtcta gcaccagtct tagtggacac accaagaaga ccagtccgca cttcttcacc    1500
tgtaccgtcg ggaagaaacc ttcgaacgca cggtattacc tgaacgacac ggaagatgtc    1560
tccgatctgc tcgactcgct gcagcaatgc actgagaaag acggcaagga gcagtggagt    1620
tcgagcaagg acgcgagttg cctctcggca ccagtcgtgg cagctgcagc ggctgcggga    1680
tcgctcgcag gcaacgcagc ggtccagctg cgcaaaggcg actctgcagc atcgaacttt    1740
gcgagtctgt ggagatcgcc gctcggatct ggagctggac gcaccagaga gcgaacgctc    1800
gcgcagtggg ctggacaggc accgagcgcc atcttcagtc gacctgtcgg agcagttgag    1860
```

```
gttcgagcca acgcagctgg cagcacagat cgcccaacag acgaggctag catat    1915
```

<210> SEQ ID NO 26
<211> LENGTH: 885
<212> TYPE: DNA
<213> ORGANISM: Artificial Sequence
<220> FEATURE:
<223> OTHER INFORMATION: gBlock 3 sequence

<400> SEQUENCE: 26

```
catatagatc tatgcacgag atcgtcgaca agaacggaaa gaaggtccag aaaaacaacc     60
tcaatgacga gatcaagatc attttcacag accttgatgg cacgcttctg aattcggaga    120
ataaagtttc gaacagaac ctggagtctc ttatccgagc gcaagaaaag gggatcaaag     180
tggtcatcgc gacggggcga tctatcttca gcgtcgaaaa cgtgattggc gaacacgtga    240
agaaaaaccg catttctctg cttcccggca tctacatgaa cggctgcgtg acgtttgatg    300
aaaagggatc tcgggtcatc gacagaatta tgaataacga tctcaagatg gagattcacg    360
aattctctaa acagattaac atttcgaagt acgcgatctg gttctgcctc gagaagacgt    420
actgcttcga aatcaatgac tgcattcgcg agtatatgga ggtcgaggcg ctgaacccgg    480
atgtgattga agacaatatg ctcgaggggc tgacagtcta taaggttctc ttttcgctcc    540
cggagaacat tctggaaaac acacttaaac tctgtaggga gaagttttcg cacaggatca    600
acgtcgcgaa taccttccag tcctacgtgg agctcttcca ccaacatacc aataaattcg    660
aaggggtgaa ggaaatctgt aaatactaca acatttccct taacaacgcc ttggccatgg    720
gcgatggcga gaatgatatt gaaatgttgt cgggattgac acattctgtt ggagttcaca    780
atgcgagcga gaaggttaag aactcggcgg cctatgtcgg gccttctaat aatgaacatg    840
cgatctctca tgttctcaaa accttctgcg acattgctag catat                    885
```

<210> SEQ ID NO 27
<211> LENGTH: 1487
<212> TYPE: DNA
<213> ORGANISM: Artificial Sequence
<220> FEATURE:
<223> OTHER INFORMATION: gBlock 4 sequence

<400> SEQUENCE: 27

```
catatagatc tatgtccgtt tatggcaaga tccctagcac ttcttttgag catgagaata     60
cattcgagct ctctggcgac ctcttggacc cggaggaact gaagtctctt ggagtctccg    120
gaagaattat ctatgtcctg cgccaccttc cgtttaaaag ctcgattaat gaagagacgc    180
gagaatggga tctttccgga cgacggggcg ctactactat gtactcgtcc atgaactggt    240
tggccaatag cacgtattgg cagaccacac tggtcggctg gaccggggtt attccgaccg    300
tttctgagaa ggaggagaat aaggatgcgg ttaccagatt ggactcgcaa gacgtgaagc    360
gcttcgaaga acatattcc caatggaact ctggggaacg cagcacagag tatgtgcctg    420
tgtggctgcc tgggccggaa aaaggcagcg aaaccatcat taacgaaacc agatcccagc    480
agtctcgctg gctcgcgtac gcagaaaatg ttatccgacc ccttattcac tataagtatt    540
ggccgtctag cgaggtggac gagaatgagg agcaatggtg gcgggattac gttaagatga    600
atcacgcttt cgctgataaa atttgtgaaa tctataagcc gggagacttt attatcgttc    660
aagactacag cctgttcctg gttccgcagc tgatcagaaa taaaattgac gacgcagtta    720
ttgggttcta tcatcatcac ccgtttccgt cctccgaaat cgctcgatgc ttcccccggc    780
```

```
gcagagcaat tctgcgatcg gttctcggag cggattttat cgggtttgaa gactattctt    840
atgcacgcca tttatttcc  tgctgttccc gtgttctgga cttggagatc gggcacgatt    900
gggtgaatct gaatggcaat aaggtgactg tgagagcaat acagtgggc  attgacgttc    960 cccgcattat ccgtagcagc gggaatgttt cggtctccga gaaattggaa gagcttaata   1020
aacggtatga acatgaag   gtgatccttg gcagagatcg gctcgacgag ctgtatgggg   1080
tccctcagaa acttagatcg tttcagcgct ttttgcgaac gtaccggag  tggcgaaaaa   1140 aggttgtgct cattcagatc acgatctcct ctgcctttaa gcatcctaag cttctcagca   1200
gcatcaagaa gctcgtgcaa gcaatcaacc aagagttcgg gacggacgac tacactcccg   1260
ttcaccatgt ggaagagcaa ctggaaccgg cagactattt cgcccttttg accagagccg   1320
atgctttgtt tatcaattcg atccgagagg gcgtctctaa tcttgccctt gaatacgtgg   1380
tttgccagcg agatcgctat ggtatggtct tgctctcgga atttacggcc acaagcgcca   1440
tgttgcacga cgttcctctg atcaatccgt gggattataa cgaatgt                 1487

<210> SEQ ID NO 28
<211> LENGTH: 1006
<212> TYPE: DNA
<213> ORGANISM: Artificial Sequence
<220> FEATURE:
<223> OTHER INFORMATION: gBlock 5 sequence

<400> SEQUENCE: 28
ccgtgggatt ataacgaatg tgctgaaatc atttctaatg cactttccac ccctctggaa     60
cgccgcaaga tgattgaacg cgagtcgtat aagcaagtca ctacacacac gatgcaatct    120
tggaccagct ctctgatccg atctctcgcc aacaagcttg ccgctactaa aactgaccaa    180
agaatcccta ctctgacgcc ggaacacgct ctgtcggtct actccaaggc gtctaagcga    240
ctgtttatga tggactatga tggaacgttg accccgatcg tccgcgatcc taatgctgcg    300
gtcccttcga agaaacttct ggataatctg caacacttg  ccgccgaccc caaaaatcag    360
gtgtggatta tctcgggccg agatcaacag ttcctgcgaa attggatgga cgatatcaag    420
ggactcgggt tgtctgctga gcatggctcg ttcgttcgaa agccgcattc cacaacgtgg    480
attaatcttg cagagctgct ggatatgtcg tggaagaagg aggttcgacg aatcttccag    540
tattatacag accgcaccca ggggtctagc atcgaagaga aacgctgtgc gatgacgtgg    600
cattacagaa aagctgaccc cgaaaacgga gcattccagg cacttgagtg tgaagcccgtt   660 ctcgaggaac tggtctgtag caagtacgat gtcgaaatca tgcgaggaaa agcgaatctc    720
gaagtcagac cctctagcat caataaagga ggcattgtca agcaaatctt gtccagctat    780
cctgaggaca gcctgccctc gttcattttc tgcgcaggcg acgaccgcac ggacgaggac    840
atgtttcggt cccttcataa aaatacgcgg attaataagg aaacatcctt tgctgtcacg    900
atcggctcgg acaagaagct gtccatcgca gactggtgca tcgccgatcc cgcaaatgtt    960
attgatatcc tggcagacct ggccaatttc accaacgcta gcatat                  1006

<210> SEQ ID NO 29
<211> LENGTH: 1505
<212> TYPE: DNA
<213> ORGANISM: Artificial Sequence
<220> FEATURE:
<223> OTHER INFORMATION: gBlock 6 sequence

<400> SEQUENCE: 29
tataagatct atgactacgg acaacgctaa agcgcagctg acctcgtctt ctggaggcaa     60
```

```
cattatagtg gtgtcgaacc gccttcccgt gacaatcact aaaaacagca gcacgggaca    120
gtacgagtat gcgatgtcgt ccggaggcct ggtcacggcg ctcgaagggc tgaagaaaac    180
gtacacgttc aagtggttcg gatggcctgg gcttgagatt ccggacgatg agaaggacca    240
ggtgcgcaag gaccttctgg agaagtttaa tgccgtcccc atctttctga gcgatgaaat    300
cgcagacctc cactacaacg ggttcagcaa ttctattctc tggccgctct ccattacca     360 tcctggcgag atcaattttg acgagaatgc gtggttggca tacaacgagg caaaccagac    420
gttcaccaac gagattgcta agacgatgaa ccacaacgac cttatctggg tgcatgacta    480
ccacctcatg ctcgttccgg agatgctgcg cgtcaagatt cacgagaagc aactgcagaa    540
cgttaaggtc ggctggttcc tgcacacgcc gtttccttcg agcgagattt acagaatcct    600
tccggtccgc caagagattt tgaagggagt cctctcgtgt gatctcgtcg ggttccacac    660
atatgactat gcgagacact tcttgtcttc cgtccagcga gtgcttaacg tgaacacact    720
cccgaatggg gtggaatacc agggcagatt cgttaacgtc ggggcctttc ctatcggcat    780
cgacgtggac aagttcaccg atgggttgaa aaaggaatcc gtccaaaaga gaatccaaca    840
gcttaaggaa actttcaaag gctgcaagat catagttgga gtcgaccggc tggactacat    900
caaaggcgtg cctcagaagt tgcacgctat ggaggtgttt ctgaatgagc atccagaatg    960
gcgaggcaaa gttgttctgg tccaggttgc agtgccatct cgcggagatg tggaagagta   1020
ccaatatctc cgatctgtgg tcaatgagct cgtcggacga atcaacggcc agttcggcac   1080
tgtggaattt gtccccatcc atttcatgca caagtctata ccatttgaag agctgatttc   1140
gctctatgcc gtgagcgacg tctgccttgt ctcgtccact cgggacggca tgaacttggt   1200
ttcctacgaa tatattgctt gccaagaaga gaagaaaggc tccctcatcc tgtctgagtt   1260
tacaggtgcc gcacagtcct tgaatggtgc gattattgtc aatccttgga acaccgacga   1320
tctttctgat gcgatcaacg aggccttgac gttgcccgac gtcaagaaag aagttaactg   1380
ggaaaaactt tacaaataca tctctaaata cacttctgcc ttctggggtg aaaatttcgt   1440
ccacgaactc tactctacat cgtctagctc gacaagctcc tctgcgacca aaaacgctag   1500
ctata                                                              1505
```

<210> SEQ ID NO 30
<211> LENGTH: 1733
<212> TYPE: DNA
<213> ORGANISM: Artificial Sequence
<220> FEATURE:
<223> OTHER INFORMATION: gBlock 7 sequence

<400> SEQUENCE: 30

```
catatagatc tatgctgtac accagggttt tcttccgtgc agtggttcgg acagacttcg     60
gtgaacgagt cgccgtcgtc gggtcttccc cgtctctggg gaattggcag gctgaacacg    120
gccatgagct gaccacaaac gaggatgtct tcccttcgtg gttctccaag gagcctgtct    180
acttgccgct aaagaaaccc atatcttaca aatatgttgt tctcgacgaa cgcggcgaca    240
tcgtgaggtg ggaagaatgc gagggaaatc gcgagttggt gcccacgggc ttggagatga    300
cggtggagga tgacgatggc ctttttaggg agcagatgac gaatcgcggc gaccacggag    360
tcgaaggcga tgacgacgtg tctgtggcgg ctctggacaa ggaggaggtg gacgcgcgca    420
accggatgct ggcgattcaa gaagaagagc ctgagttcga cgagaacgac agcgtaattg    480
tggtcgctaa ccgcttgcct ctgcgcgtgg tgcgtgtctc gccgtctcgt gaggcttctc    540
```

```
cgctgccctc ctcgctgcct gcgtcgtcga ccgactcttc cggccaaaca gaaaagcgag      600
cggtttcatt cccggaagac gcgggagcga gtgcacggcg ctcgagttcg accgtcgcgg      660
caactcggga ggaggaaacg actcgcactg cgagttcctt tcctaaagtc gaggagacgg      720
cggaaagagg acgagacagc tcgctcgctc tttggcctgg cgcagcacgc gacgctgccg      780
gcgacttcgg ggaggcgctt cagccgagag cgacccgcag ccgacgaggc acctttgaag      840
tgaggccgag caagggcgga ttgcttcctt cgctgtttca cctgcgcaag aagacgcggc      900
tgcctgtgcg ttgggtcggg tggccgggaa tccacgtcga gaacgaagag gagcaggcgg      960
agattgcgga gctgctgcga gcctacgact gttcgccgat cttcctcgac aaagacgagt     1020
tcgactgcca ttacaacggc ttctcgaatt ctatcctgtg gccgctgttt cacaacgtcg     1080
tcgtccttga ctccaatacc caggtcccgt cgactccga cctctgggcc aagtaccagg      1140
ctgtgaacaa actgtgggcg gacgcggtgc tccgccaggc gcacgaaacc gacatggtct     1200
gggtccacga ctaccacctg ctcctcgcgc ccatgcacct ccgccggaaa gtccgacgcg     1260
ccaacgtcgg cttctttctt cacatcccct ccctcttc cgaaatcttc aggtgtctcc       1320
cttgccgaga agacattttg cgaggggtgc tgtgcgcgga cttgattggg tttcacctct     1380
tcgagtacgc gcgccacttt ctggtcgcat gcaagcggct gctcggcctc gagcaccatt     1440
tttgtcgagg gggcattctg aacatcgagt acggcggccg caacgtctcg gtccgcatcg     1500
gccctatcgg cattgactac gccgacattc gctcgaaaat cgaggcaaac ccggtggttc     1560
tgcagatggc gcgagacatc agacaaaaac acgtcggaaa attcatcttc gtctccgtgg     1620
accgcctgga catgatcaag ggtctcctcc tcaaagttcg cgccttccag gcgtttctcg     1680
tgacctactc ttatgccagg ggaaatgtcg tcctcattca gtacgcgtat cct            1733
```

<210> SEQ ID NO 31  
<211> LENGTH: 1964  
<212> TYPE: DNA  
<213> ORGANISM: Artificial Sequence  
<220> FEATURE:  
<223> OTHER INFORMATION: gBlock 8 sequence

<400> SEQUENCE: 31

```
cgtcctcatt cagtacgcgt atcctacccg cacggacgtc cctgagtacc agaagctcaa       60
atctcaggtg cacgagctcg tgggcagaat caatggacag ttcggcttgg tcgatcgccc      120
agatttccaa catatcgaac tccacatcca gccggtcggc tgggaggagc tctgggcgtt      180
gtttaccgcg ggcgacgtta tgcttgtgac atcgatccga gatggcatga atctcgtctc      240
gtacgaattt atctgttgcc acaaagacaa cgtcaccggt gtgattttat cagagttcac      300
ggggtgcagc agagccctcg cctcggccat tcgcgtcaat ccttggaagg tggaggcggt      360
ggcagatgcg atggacagaa tcatcaacat gcctgtggag gagcagcgcg accggttcac      420
ccgcgaccgc gactacttga gtcacaacag tacgcagaag tgggcagacg aaaacattct      480
ggatctgcga cgagcccgga accagacga cttcgtctac gtctcttggg gtctcggcaa      540
caccttccgc gtcctaggca tggactccaa cttccggttt ctggacacaa atcaagtggt      600
gcgaggctac cgaacttctc gacatcgcgt cttcttcttc gactacgacg gcacactctc      660
tccgatcgta gaggacccgg ataatctttt tgcgcaaggt cgcccgcctt cgccgcaagt      720
caaggactgt ctccaggcgc ttgtcgacga ccaaagaaac actgttgtca ttctctcggg      780
acgcgacaga cacctcctag aggaatggtt ctccttccatc agaggcattg gactttgtgc      840
cgaacacggt ttttactacc gggttccggg catcacgggg gaccagtggc actgcatgtc      900
```

```
tcgtcaaaca gacttcacat ggaagcaagt ggcgatcgag ctgatgctgc agtatgtgaa    960
gcgaactcag ggctcattca tcgaaaacaa aggaagtgct ctcgtcttcc agtaccgcga   1020
cgcagatccg gatttcggca gcatgcaagc caaggatctc tcgaactacc tcggggaact   1080
gctcttcggc tatcctgtct cggtcatgag cgggaaaggc tacgtggaag tgaaactgcg   1140
aggtgtcaac aaagggcatg cagtcgagaa agttctgcgg aaactcagca acctccacgg   1200
agacgtcgac ttcgttctct gcgtcggaga tgacagaacg gacgaagaca tgttcgcggt   1260
catcaacgcc atgacggaag acggggacca gctgtgcctg ccagagggca gcggcgccgg   1320
gagcagcggc ctctatcgcc acacacagtc gaaggatcga attcctagac gcaactctgt   1380
ctcttcggat gagaaccgag cagaagctgt cgttggaaac gtggagggac tcatgaagcg   1440
tgacgggtcg atgcagcatg cggggcgct cggcagcggc ttgacctctg cgtcttccag   1500
cacaagtctc agtgggcaca caaagaaaac gagtcctcac ttttcacat gcacagtcgg   1560 caagaagccg tccaacgctc ggtattacct caacgacact gaggatgtct ccgatctcct   1620
cgactctctg cagcagtgca ctgagaagga cgggaaggag cagtggagtt cgtcgaagga   1680
cgcgagttgc ctctcggcgc cagtcgtggc agctgcagct gctgcgggat cgctcgcggg   1740
gaacgcggcg gtgcagctga ggaaaggcga cagcgcagct tcgaactttg cgagtctgtg   1800
gagatcgcct ctgggatcag gagcaggtcg cacgagagaa cgaacgctcg cgcagtgggc   1860
ggggcaggca ccgagcgcca tcttcagtcg ccccgtcggt gccgttgaag ttcgcgccaa   1920
cgcagctggc agcacagatc gcccaacaga cgaggctagc atat                   1964
```

<210> SEQ ID NO 32
<211> LENGTH: 1789
<212> TYPE: DNA
<213> ORGANISM: Artificial Sequence
<220> FEATURE:
<223> OTHER INFORMATION: gBlock 9 seqeunce

<400> SEQUENCE: 32

```
catatagatc tatgctgtac accagggttt tcttccgtgc agtggttcgg acagacttcg     60
gtgaacgagt cgccgtcgtc gggtcttccc cgtctctggg aatctccag gctgaacacg    120 gccatgagct gaccacaaac gaggatgtcg cgccttcgtg gttctccaag gagcctgtct    180
acttgccgct aaagaaaccc atatcttaca aatatgttgt tctcgacgaa cgcggcgaca    240
tcgtgaggct ggaagaatgc gagggaaatc gcgagttggt gcccacgggc ttggagatga    300
cggtggagga tgacgatggc cttttaggg agcagatgac gaatcgcggc gaccacggag    360
tcgaaggcga tgacgacgtg tctgtggcgg ctctggacaa ggaggaggtg gacgcgcgca    420
accggatgct ggcgattcaa gaagaagagc ctgagttcga cgagaacgac agcgtaattg    480
tgtgtgctct tgacttgcct ctgcgcgtgg tgcgtgtctc gccgtctcgt gaggcttctc    540
cgctgccctc ctcgctgcct gcgtcgtcga ccgactcttc cggccaaaca gaaaagcgag    600
cggtttcatt cccggaagac gcgggagcga gtgcacggcg ctcgagttcg accgtcgcgg    660
caactcggga ggaggaaacg actcgcactg cgagttcctt tcctaaagtc gaggagacgg    720
cggaaagagg acgagacagc tcgctcgctc tttggcctgg cgcagcacgc gacgctgccg    780
gcgacttcgg ggaggcgctt cagccgagag cgacccgcag ccgacgaggc accttttgaag   840 tgaggccgag caagagcgcg ttgcttcctt cgctgtttca cctgcgcaag aagacgcggc    900
tgcctgtgcg tttcgtcggg tggccgggaa tccacgtcga gaacgaagag gagcaggcgg    960
```

```
agattgcgga gctgctgcga gcctacgact gttcgccgat cttcccagac aaagacgagt   1020
tcgactgcca tctcaccttc tgccatcagg tcctgtggcc gctgtttcac aacgtcgtcg   1080
tccttgactc caatacccag gtcccgttcg actccgacct ctgggccaag taccaggctg   1140
tgaacaaact gtgggcggac gcggtgctcc gccaggcgca cgaaaccgac atggtctggg   1200
tccacgacta ccacctgctc ctcgcgccca tgcacattac gcggaaagtc cgacgcgcca   1260
acgtcggctt ctttcttcac atcccctccc cctcttccga aatcttcagg tgtcccctt    1320 gccgagaaga cattttgcga gggatgctgt gcgcggactt gattgggttt cacctcttcg   1380
agtacgcgcg ccactttctg gtcgcatgca agcggctgct cggcctcgag caccattttt   1440 gtcgagggggg cattctgaac atcgagtacg gcggccgcaa cgtctcggtc cgcatcggcc  1500
atgtccacat tcagtacgcc gacattcgct cgaaaatcga ggcaaacccg gtggttctgc   1560
agatggcgcg agacatcaga caaaaacacg tcggaaaatt catcttcgtc tccgtggacc   1620
gctgcgagaa attggccggt ctcctcctca aagttcgcgc cttccaggcg tttctcgtga   1680
cctactctta tgccagggga aatgtcgtcc tcattcagta cgcgtatcct accatcaaat   1740
acgcagaaga cacagaaacc atggcgacgg aactcaaaga gctcgtgga               1789

<210> SEQ ID NO 33
<211> LENGTH: 440
<212> TYPE: DNA
<213> ORGANISM: Artificial Sequence
<220> FEATURE:
<223> OTHER INFORMATION: gBlock 10 sequence

<400> SEQUENCE: 33
ctctcaggtg ggcagtggcg tcggtttctt ctctcttcat tctcttgtcg cctgcgaagt   60
cgcgctgcgt gtctgcagct cgcgtttctt gtcgaggata aatacgcggt gccccaagac   120
atcgaaggag tcgtcgtcgg tgcggagact gttgccctgg tccagacgcg tacgcaggtc   180
cctagggaac aaaagttgat ttctgaagaa gatttgaacg gtgaacaaaa gctaatctcc   240
gaggaagact tgaacggtgc tagggccgag gagcagaagc tgatctccga ggaggacctg   300
tgagcacaca gcatcgtctt gacgcgtctc gacctcgctc tcgcgactca cttctccgga   360
gagacggaaa aacggtgcga gtcaagaact caggagaccc cgaatccgca gcttctacac   420
atcacggttc aggccggtca                                              440

<210> SEQ ID NO 34
<211> LENGTH: 35
<212> TYPE: DNA
<213> ORGANISM: Artificial Sequence
<220> FEATURE:
<223> OTHER INFORMATION: synthetic oligo sequence

<400> SEQUENCE: 34
catatagatc tatgctgtac accagggttt tcttc                             35

<210> SEQ ID NO 35
<211> LENGTH: 24
<212> TYPE: DNA
<213> ORGANISM: Artificial Sequence
<220> FEATURE:
<223> OTHER INFORMATION: synthetic oligo sequence

<400> SEQUENCE: 35
tccacgagct ctttgagttc cgtc                                         24
```

<210> SEQ ID NO 36
<211> LENGTH: 29
<212> TYPE: DNA
<213> ORGANISM: Artificial Sequence
<220> FEATURE:
<223> OTHER INFORMATION: synthetic oligo sequence

<400> SEQUENCE: 36
ctcaaagagc tcgtggagaa agtcaatgc                                   29

<210> SEQ ID NO 37
<211> LENGTH: 28
<212> TYPE: DNA
<213> ORGANISM: Artificial Sequence
<220> FEATURE:
<223> OTHER INFORMATION: synthetic oligo sequence

<400> SEQUENCE: 37
atatgctagc ctcgtctgtt gggcgatc                                    28

<210> SEQ ID NO 38
<211> LENGTH: 32
<212> TYPE: DNA
<213> ORGANISM: Artificial Sequence
<220> FEATURE:
<223> OTHER INFORMATION: synthetic oligo sequence

<400> SEQUENCE: 38
catatagatc tatgcacgag atcgtcgaca ag                               32

<210> SEQ ID NO 39
<211> LENGTH: 31
<212> TYPE: DNA
<213> ORGANISM: Artificial Sequence
<220> FEATURE:
<223> OTHER INFORMATION: synthetic oligo sequence

<400> SEQUENCE: 39
atatgctagc aatgtcgcag aaggttttga g                                31

<210> SEQ ID NO 40
<211> LENGTH: 32
<212> TYPE: DNA
<213> ORGANISM: Artificial Sequence
<220> FEATURE:
<223> OTHER INFORMATION: synthetic oligo sequence

<400> SEQUENCE: 40
catatagatc tatgtccgtt tatggcaaga tc                               32

<210> SEQ ID NO 41
<211> LENGTH: 28
<212> TYPE: DNA
<213> ORGANISM: Artificial Sequence
<220> FEATURE:
<223> OTHER INFORMATION: synthetic oligo sequence

<400> SEQUENCE: 41
acattcgtta taatcccacg gattgatc                                    28

<210> SEQ ID NO 42
<211> LENGTH: 30
<212> TYPE: DNA
<213> ORGANISM: Artificial Sequence
<220> FEATURE:
<223> OTHER INFORMATION: synthetic oligo sequence

```
<400> SEQUENCE: 42
ccgtgggatt ataacgaatg tgctgaaatc                                      30

<210> SEQ ID NO 43
<211> LENGTH: 28
<212> TYPE: DNA
<213> ORGANISM: Artificial Sequence
<220> FEATURE:
<223> OTHER INFORMATION: synthetic oligo sequence

<400> SEQUENCE: 43
atatgctagc gttggtgaaa ttggccag                                        28

<210> SEQ ID NO 44
<211> LENGTH: 29
<212> TYPE: DNA
<213> ORGANISM: Artificial Sequence
<220> FEATURE:
<223> OTHER INFORMATION: synthetic oligo sequence

<400> SEQUENCE: 44
atatgctagc gagacagtcc ttgacttgc                                       29

<210> SEQ ID NO 45
<211> LENGTH: 27
<212> TYPE: DNA
<213> ORGANISM: Artificial Sequence
<220> FEATURE:
<223> OTHER INFORMATION: synthetic oligo sequence

<400> SEQUENCE: 45
cacgagatcg tcgacaagaa cggaaag                                         27

<210> SEQ ID NO 46
<211> LENGTH: 27
<212> TYPE: DNA
<213> ORGANISM: Artificial Sequence
<220> FEATURE:
<223> OTHER INFORMATION: synthetic oligo sequence

<400> SEQUENCE: 46
gcatatagat ctatgctgta caccagg                                         27

<210> SEQ ID NO 47
<211> LENGTH: 16
<212> TYPE: DNA
<213> ORGANISM: Artificial Sequence
<220> FEATURE:
<223> OTHER INFORMATION: synthetic oligo sequence

<400> SEQUENCE: 47
aggcgggcga ccttgc                                                     16

<210> SEQ ID NO 48
<211> LENGTH: 18
<212> TYPE: DNA
<213> ORGANISM: Artificial Sequence
<220> FEATURE:
<223> OTHER INFORMATION: synthetic oligo sequence

<400> SEQUENCE: 48
cttgacttgc ggcgaagg                                                   18

<210> SEQ ID NO 49
<211> LENGTH: 29
```

```
<212> TYPE: DNA
<213> ORGANISM: Artificial Sequence
<220> FEATURE:
<223> OTHER INFORMATION: synthetic oligo sequence

<400> SEQUENCE: 49
tccgtttatg gcaagatccc tagcacttc                                    29

<210> SEQ ID NO 50
<211> LENGTH: 33
<212> TYPE: DNA
<213> ORGANISM: Artificial Sequence
<220> FEATURE:
<223> OTHER INFORMATION: synthetic oligo sequence

<400> SEQUENCE: 50
tataagatct atgactacgg acaacgctaa agc                               33

<210> SEQ ID NO 51
<211> LENGTH: 27
<212> TYPE: DNA
<213> ORGANISM: Artificial Sequence
<220> FEATURE:
<223> OTHER INFORMATION: synthetic oligo sequence

<400> SEQUENCE: 51
tatagctagc gttttggtc gcagagg                                       27

<210> SEQ ID NO 52
<211> LENGTH: 39
<212> TYPE: DNA
<213> ORGANISM: Artificial Sequence
<220> FEATURE:
<223> OTHER INFORMATION: synthetic oligo sequence

<400> SEQUENCE: 52
tataagatct atgctgtaca ccagggtttt cttccgtgc                         39

<210> SEQ ID NO 53
<211> LENGTH: 27
<212> TYPE: DNA
<213> ORGANISM: Artificial Sequence
<220> FEATURE:
<223> OTHER INFORMATION: synthetic oligo sequence

<400> SEQUENCE: 53
cggaggcctg ccctgctccc taaaaag                                      27

<210> SEQ ID NO 54
<211> LENGTH: 25
<212> TYPE: DNA
<213> ORGANISM: Artificial Sequence
<220> FEATURE:
<223> OTHER INFORMATION: synthetic oligo sequence

<400> SEQUENCE: 54
tcccgagcct ccgcgattcg tcatc                                        25

<210> SEQ ID NO 55
<211> LENGTH: 30
<212> TYPE: DNA
<213> ORGANISM: Artificial Sequence
<220> FEATURE:
<223> OTHER INFORMATION: synthetic oligo sequence

<400> SEQUENCE: 55
```
actacggaca acgctaaagc gcagctgacc                                    30

<210> SEQ ID NO 56
<211> LENGTH: 27
<212> TYPE: DNA
<213> ORGANISM: Artificial Sequence
<220> FEATURE:
<223> OTHER INFORMATION: synthetic soligo sequence

<400> SEQUENCE: 56
aggatacgcg tactgaatga ggacgac                                       27

<210> SEQ ID NO 57
<211> LENGTH: 28
<212> TYPE: DNA
<213> ORGANISM: Artificial Sequence
<220> FEATURE:
<223> OTHER INFORMATION: synthetic oligo sequence

<400> SEQUENCE: 57
cgtcctcatt cagtacgcgt atcctacc                                      28

<210> SEQ ID NO 58
<211> LENGTH: 29
<212> TYPE: DNA
<213> ORGANISM: Artificial Sequence
<220> FEATURE:
<223> OTHER INFORMATION: synthetic oligo sequence

<400> SEQUENCE: 58
tgatagatct tgtgcagaag gtgctccac                                     29

<210> SEQ ID NO 59
<211> LENGTH: 28
<212> TYPE: DNA
<213> ORGANISM: Artificial Sequence
<220> FEATURE:
<223> OTHER INFORMATION: synthetic oligo sequence

<400> SEQUENCE: 59
tatacctagg ctcgtctgtt gggcgatc                                      28

<210> SEQ ID NO 60
<211> LENGTH: 22
<212> TYPE: DNA
<213> ORGANISM: Artificial Sequence
<220> FEATURE:
<223> OTHER INFORMATION: synthetic oligo sequence

<400> SEQUENCE: 60
ctctcaggtg ggcagtggcg tc                                            22

<210> SEQ ID NO 61
<211> LENGTH: 21
<212> TYPE: DNA
<213> ORGANISM: Artificial Sequence
<220> FEATURE:
<223> OTHER INFORMATION: synthetic oligo sequence

<400> SEQUENCE: 61
tgaccggcct gaaccgtgat g                                             21

<210> SEQ ID NO 62
<211> LENGTH: 33
<212> TYPE: DNA
<213> ORGANISM: Artificial Sequence -continued

```
<220> FEATURE:
<223> OTHER INFORMATION: synthetic oligo sequence

<400> SEQUENCE: 62
gagtcgtcgt gttttagagc tagaaatagc aag                    33

<210> SEQ ID NO 63
<211> LENGTH: 30
<212> TYPE: DNA
<213> ORGANISM: Artificial Sequence
<220> FEATURE:
<223> OTHER INFORMATION: synthetic oligo sequence

<400> SEQUENCE: 63
cttcgatgtc aacttgacat ccccatttac                        30
```

PARASITE VACCINE

CROSS REFERENCE TO RELATED APPLICATIONS

The present invention is a national stage application which claims priority from PCT Application No. PCT/AU2019/050433 filed May 10, 2019, and Australian Patent Application No. 2018901691 filed 15 May 2018 and Australian Patent Application No. 2018904620 filed 5 Dec. 2018. The entire contents of these documents are incorporated by reference in their entirety.

All documents cited or referenced herein, and all documents cited or referenced in herein cited documents, together with any manufacturer's instructions, descriptions, product specifications, and product sheets for any products mentioned herein or in any document incorporated by reference herein, are hereby incorporated herein by reference in their entirety.

The entire content of the electronic submission of the sequence listing is incorporated by reference in its entirety for all purposes.

The entire content of the patent deposit receipts referred to herein is incorporated by reference in their entirety.

FIELD OF THE DISCLOSURE

The present disclosure provides mutant parasites, in particular protozoan parasites comprising a mutation of the trehalose-6-phosphate synthase/6-phosphate phosphatase (TPS/TPP)-like gene of *Toxoplasma gondii* (herein referred to as '*Toxoplasma*') or a homologue thereof as well as vaccines comprising same.

BACKGROUND

The phylum Apicomplexa comprises a group of obligate intracellular parasites that cause a range of disease by actively invading and replicating within host cells. Like all intracellular pathogens, these parasites extensively modify their host cells in order to prevent immune clearance while permitting nutrient acquisition for growth.

*Toxoplasma gondii* (*Toxoplasma*) is one of the most common human pathogens infecting 10-80% of individuals within a population (Fischer H G et al. (1997) Eur J Immunol. 27:1539-48). In humans, the risk is to unborn human babies and immunocompromised individuals. A pregnant woman may have the infection and unknowingly infect the foetus. Even if diagnosed and treated, the child may be born with permanent brain and eye damage. Diagnosis during pregnancy is uncertain at best and treatment uncertain and risky. For this reason, efforts to prevent infection during pregnancy are important.

*Toxoplasma*, which is the cause of toxoplasmosis, is an obligate intracellular protozoan parasite. As well as infecting humans, it can infect virtually all warm blooded animals. It has been found worldwide with nearly one-third of humanity having been exposed to the parasite. *Toxoplasma* is transmitted with the ingestion of sporulated oocytes present in soil, water or vegetables contaminated with cat faeces, or by ingesting raw or undercooked meat harbouring tissue cysts.

In farm livestock, species such as sheep and goats, congenital infection is common and may result in abortion and neonatal mortality (Buxton (1998) Vet Res 29: 289-310). Animals bred to produce meat for human consumption may be persistently infected with *Toxoplasma*, contained within tissue cysts in the muscles and viscera and can act as important sources of infection for people.

A very important animal in the life cycle of *Toxoplasma* and the epidemiology of the disease is the cat. Young cats tend to become infected with *Toxoplasma* when they go hunting for the first time and eat wild rodents and birds. Following a primary infection, cats will shed millions of oocysts in their faeces that can survive for 12-18 months in the environment, depending on climactic conditions, and are an important source of infection for grazing animals (Tenter et al. (2000) Int J Parasitol 30: 1217-1258).

It is known in the art that animals can be immunized against toxoplasmosis. However, vaccines to date have not been completely successful or otherwise suffer from shortcomings. For example, primary infection of cats (an important carrier of *Toxoplasma*) is usually followed by oocyst shedding before build-up of immunity. This phenomenon largely defeats the purpose of immunization, in that infective oocysts in the cat faeces are a prime carrier of the disease. Furthermore, all known strains of the organism used for primary infections of mammals, while effective for purposes of building up immunity, tend to persist in the mammal for a long period of time, and possibly for a lifetime, with the result that the mammal is chronically infected. This in turn raises the possibility that if such a mammal becomes immunosuppressed later in life, the infection may reactivate with debilitating or even fatal results, furthermore, it is uncertain whether the meat and viscera used for human consumption could be infected with this strain.

At present, only one commercial vaccine "Toxovax" (Intervet) based on live attenuated S48 strain of *Toxoplasma* has been licensed for use to avoid congenital infection in ewes (Buxton D (1993) Parasitol Today 9:335-337). However, this vaccine is expensive, causes adverse effects, and has a short shelf-life (as it typically required administration within 3 weeks of manufacture). Additionally, since attenuation of the vaccine is produced through repeated serial passage, it is slow to manufacture due to its slow growth. Additionally, the vaccine is genetically undefined and accordingly the mechanism of attenuation is not known. Furthermore, studies have shown that this vaccine can revert to a pathogenic strain and therefore it is not suitable for human use (Zhang N Z et al. (2013) Expert Rev. Vaccines 12(11):1287-1299). The vaccine does not produce cysts and thus the immune system will not see antigen during this stage of the lifecycle. The other disadvantage of this vaccine is that it is only partially protective in animals in so far as the vaccine leads to a reduced level of cyst burden but not complete absence since only about 60-70% of ewes are protected from abortion (Zhang N Z et al. (2013) Expert Rev. Vaccines 12(11):1287-Thus, there is a need in the art for effective vaccines which provide an adequate and consistent level of immunity when immunized into an animal but which do not persist and cause chronic infection in the immunized animal through return to virulence. Furthermore, there is a need in the art for vaccines which are genetically defined and which can be safely used for non-human animals and humans.

SUMMARY OF THE DISCLOSURE

In work leading up the present disclosure, the inventors determined that the $Ca^{2+}$ dependent protein kinase, CDPK2 is a critical regulator of amylopectin metabolism. Increased synthesis and loss of degradation of amylopectin in CDPK2 deficient parasites results in the hyper-accumulation of this sugar polymer (Uboldi A et al. (2015) *Host Cell and Microbe* 18:670-681).

The inventors have now identified a protein in *Toxoplasma* that has homology to two enzymes of the trehalose biosynthetic pathway of bacteria, fungi and plants, namely trehalose-6-phosphate synthase (TPS) and trehalose/6-phosphate phosphatase (TPP). Notably, both TPS and TPP proteins and the trehalose biosynthetic pathway in which they function are not present in mammalian cells. The *Toxoplasma* TPS/TPP-like gene contains both trehalose 6-phosphate synthase (TPS)-like and trehalose 6-phosphate phosphatase (TPP)-like domains arranged in tandem, as well as an N-terminal amylopectin-binding CBM20 domain, allowing for direct interaction with amylopectin. In particular, the inventors have found that this protein has a regulatory role in glucose/amylopectin metabolism in *Toxoplasma*. However, in contrast to the plant proteins, the TPS/TPP-like protein in parasites lacks important substrate binding residues and neither T6P biosynthetic activity from the TPS domain, nor trehalose production from the TPP domain has been detected.

The present disclosure is based on the finding that disruption of the TPS/TPP-like gene in parasites containing the TPS/TPP-like gene or a homolog thereof alters starch (e.g. amylopectin) metabolism in the parasite. More particularly, the inventors found that disruption of the TPS/TPP-like gene results in greater attenuation of *Toxoplasma* parasites than disruption of the CDPK2 gene. Additionally, the TPS/TPP-like gene mutants were incapable of forming cysts.

The vaccines of the present disclosure provide a number of advantages over prior art vaccines such as Toxovax. These advantages include:
(i) they are genetically defined;
(ii) they have a known mechanism of attenuation; and
(iii) they produce cysts (bradyzoites) that do not persist in the host thus allowing for an immune response to by mounted. However, because the cysts cannot persist in the host, the risk of transmission to humans is considerably low to absent.

Attenuation of the mutant TPS/TPP parasites described herein was achieved by altering the growth medium of the parasites to contain glucose. In glucose-free medium, the parasites grow normally. However, in the presence of glucose-containing medium, parasites comprising a disruption of the TPS/TPP-like protein will massively accumulate amylopectin within the cytoplasm which goes on uncontrolled. For type II mutant *T. gondii* parasites, the amylopectin accumulation continued uncontrollably resulting in death. Such mutants comprising an inactivating mutation of the TPS/TPP-like gene are referred to herein in the description and examples as Δtps/tpp mutants. The inventors show herein that when Δtps/tpp parasites are given to mice, they become completely attenuated in vivo.

Vaccines comprising Δtps/tpp parasites are thus particularly useful. Because the parasites once introduced into the host become attenuated and ultimately die, they cannot revert to virulence in the immunised host and furthermore, are not capable of forming persistent tissue cysts in the immunised host. These properties make the vaccine attractive for human and animal use.

Additionally, vaccines comprising Δtps/tpp parasites are particularly useful for the immunisation of cats since oocyst production relies on normal starch metabolism and thus it is likely that oocyst shedding will be prevented.

In a first aspect, the present disclosure provides an isolated mutant parasite, wherein the mutant is attenuated when grown in glucose-containing medium but not attenuated in glucose-free (i.e. glutamine-containing) medium. The term "isolated mutant parasite" as used herein is also intended to refer to a population of such mutant parasites. In a particular example, the mutant is live. In one example, the mutant parasite uncontrollably accumulates starch-like amylopectin stores when grown in glucose-containing medium. In another example, the parasite is a protozoan parasite. In a particular example, the parasite is *Toxoplasma gondii* (*T. gondii*).

In one example, the parasite comprises an inactivating mutation of the trehalose-6-phosphate synthase/6-phosphate phosphatase (TPS/TPP)-like gene of *T. gondii* or a homolog thereof. In one example, the mutant parasite is a Δtps/tpp parasite. In one example, the mutant parasite is not a ΔCDPK2 mutant as described in Uboldi A et al., (2015) Cell Host & Microbe 18,670-681.

In one example, the TPS/TPP-like gene is TGGT1_297720 in the *Toxoplasma* Genomics Resource (named loxodb.org) or a homolog thereof. In one example, the TPS/TPP-like gene comprises or consists of the sequence according to SEQ ID NO:1 (FIG. 1). In one example, the sequence is the genomic sequence of the TPS/TPP-like gene. In one example the sequence is the cDNA sequence of the TPS/TPP-like gene, for example as shown in SEQ ID NO:3. The TPS/TPP-like gene also extends to homologs of TPS/TPP-like gene of *Toxoplasma*, said homolog being present in a parasite, particularly a protozoan parasite, more particularly a coccidian parasite. In some examples, the homolog comprises at least 80% identity to SEQ ID NO:1 or the N-terminal 200 nucleotides thereof (SEQ ID NO:2).

The skilled person will appreciate that there are a number of different methods by which a gene can be inactivated or mutated in accordance with the present disclosure. In one example, the mutation results in inactivation of the TPS/TPP-like gene which is achieved by either a targeted or a non-targeted (i.e. random) disruption of the gene. The disruption may occur in a coding or non-coding sequence of the TPS/TPP-like gene. In a further example, inactivation of TPS/TPP-like gene function is caused by disruption of one or more regulatory sequences upstream of the TPS/TPP gene such that transcription of the gene is prevented. In another example, the disruption is a frame-shift mutation in the coding sequence of the TPS/TPP-like gene. In one example, either the TPS-like domain or the TPP-like domain is disrupted or inactivated (either partially or wholly). In another example, both the TPS-like and TPP-like domains are disrupted or inactivated (either partially or wholly). In another example, inactivation of the TPS/TPP-like gene is caused by gene knock-down or gene knock-out.

In certain examples, targeted disruption of the TPS/TPP-like gene comprises an insertion or deletion of one or more contiguous nucleotides in the TPS/TPP-like gene. In other examples, the insertion or deletion causes a frame-shift in the TPS/TPP-like gene sequence. In a further example, the insertion or deletion results in formation of a stop codon thus truncating translation of the resulting protein. Still further, inactivation of the TPS/TPP-like gene may occur through removal of all of the gene (i.e. null mutation).

In an example, the TPS/TPP-like gene is inactivated or disrupted such that uncontrolled amylopectin accumulation occurs in the parasite when grown in glucose-containing medium.

In one example, the mutant parasite comprises an insertion of one or more contiguous or non-contiguous heterologous nucleotides within the TPS/TPP-like gene, for example the TPS/TPP-like gene sequence according to SEQ ID NO:1 or SEQ ID NO:3. In a further example, the mutant parasite comprises a deletion of one or more contiguous or non-contiguous native nucleotides within the TPS/TPP-like gene sequence, for example, the TPS/TPP-like gene sequence according to SEQ ID NO:1 or SEQ ID NO:3.

For example, the mutant parasite may comprise an insertion of between 1 and 1500 heterologous nucleotides within the TPS/TPP-like gene of *Toxoplasma* or a homolog thereof. In a further example, the mutant parasite comprises an insertion of between 1 and 1000 heterologous nucleotides, between 1 and 800 heterologous nucleotides, between 1 and 750 heterologous nucleotides, between 1 and 500 heterologous nucleotides, between 1 and 250 heterologous nucleotides, between 1 and 100 heterologous nucleotides, between 1 and 50 heterologous nucleotides, between 1 and 25 heterologous nucleotides, between 1 and 20 heterologous nucleotides, between 1 and 15 heterologous nucleotides, between 1 and 10 heterologous nucleotides, or between 1 and 5 heterologous nucleotides. The mutant parasite may comprise an insertion of at least three, at least five, at least ten, at least twenty, at least forty, at least fifty, at least eighty, at least one hundred and/or up to five hundred heterologous nucleotides. The inserted nucleotides may be contiguous or non-contiguous.

In certain examples, the mutant parasite comprises a deletion of native nucleotides within the TPS/TPP-like gene sequence. In further examples, the mutant parasite comprises a deletion of between 1 and 1000 contiguous nucleotides, between 1 and 800 contiguous nucleotides, between 1 and 750 contiguous nucleotides, between 1 and 500 contiguous nucleotides, between 1 and 250 contiguous nucleotides, between 1 and 100 contiguous nucleotides, between 1 and 50 contiguous nucleotides, between 1 and 25 contiguous nucleotides, between 1 and 20 contiguous nucleotides, between 1 and 15 contiguous nucleotides, between 1 and 10 contiguous nucleotides, or between 1 and 5 contiguous nucleotides within the native TPS/TPP-like gene sequence of *Toxoplasma* or a homolog thereof The mutant parasite may comprise a deletion of at least three, at least five, at least ten, at least twenty, at least forty, at least fifty, at least eighty, at least one hundred and/or up to five hundred native nucleotides.

In another example, the deleted nucleotides are non-contiguous.

In another example, the TPS/TPP mutant parasite (Δtps/tpp parasite) accumulates amylopectin stores at a substantially faster rate compared to a corresponding parasite containing wild-type TPS/TPP.

The TPS/TPP-like gene may be disrupted at any location within in the gene (e.g. at any nucleotide position within the TPS/TPP-like gene sequence). More particularly, disruption may occur at any nucleotide position within the TPS/TPP-like gene sequence set forth in SEQ ID NO:1, SEQ ID NO:2 (corresponding to the first 200 nucleotides from the N-terminus of SEQ ID NO:1) or SEQ ID NO:3. In one example, disruption of the TPS/TPP-like gene may occur within the TPS-like domain. In one example, disruption of the TPS/TPP-like gene may occur within the TPP-like domain. In one example, disruption the TPS/TPP-like gene may occur within the amylopectin-binding domain (also known as the carbohydrate binding domain 20 (i.e. CBM20)).

In certain examples, the TPS/TPP-like gene or homolog thereof is disrupted at a point within the first exon sequence defined by nucleotide residues at position 1 to 99 of SEQ ID NO:1 or SEQ ID NO:2. In other example, the TPS/TPP-like gene is disrupted at any nucleotide position within the second exon sequence, the third exon sequence, the fourth exon sequence, within the fifth exon sequence, within the sixth exon sequence, within the seventh exon sequence, within the eight exon sequence, within the ninth exon sequence, within the tenth exon sequence, within the eleventh exon sequence, within the twelfth exon sequence, within the thirteenth exon sequence, within the fourteenth exon sequence, within the fifteenth exon sequence, within the sixteenth exon sequence, within the seventeenth exon sequence or within the eighteenth exon sequence of the TPS/TPP-like gene sequence according to SEQ ID NO:1 or homolog thereof.

It will be appreciated that any parasite, in particular protozoan parasite comprising a TPS/TPP-like gene of the disclosure or a homolog thereof can be mutated according to the present disclosure. In one example the parasite is a coccidian parasite. In another example, the parasite belongs to the Apicomplexa phylum. In other examples, the parasite is selected from the group consisting of a *Toxoplasma, Neospora, Cryptosporidium* or *Eimeria* parasites. In a further example, the parasite is *Neospora caninum, Toxoplasma gondii* or *Eimeria tenella*.

In one example, the TPS/TPP-like gene is disrupted by nucleotide insertion or deletion at any nucleotide residue located between and/or including position 1 and 500, position 501 and 1000, position 1001 and 1500, position 1501 and 3000 or position 3001 and 3666 of SEQ ID NO:3.

In another example, the TPS/TPP-like gene is disrupted by nucleotide insertion or deletion at any nucleotide residue between and/or including residues 40 and 150, residues 50 and 140, residues 55 and 125, residues 60 and 120 or residues 78 and 100 of SEQ ID NO:1 or SEQ ID NO:2.

In another example, the TPS/TPP-like gene is disrupted by nucleotide insertion or deletion at any nucleotide position between and/or including residues 78 to 97 of SEQ ID NO:1 or SEQ ID NO:2.

In a further example, the disruption of the TPS/TSS-like gene results in loss of the proto-spacer sequence (CCCGTCTCTGGGGAATTGGC; SEQ ID NO:22) and/or the proto-spacer adjacent motif (PAM) sequence (AGG).

In certain examples, the mutant parasite is a *Toxoplasma* mutant. The *Toxoplasma* mutant according to the disclosure may be derived from any strain. For example, the *Toxoplasma* mutant may be the RH (Type I), Pru (Type II) or CTG (Type III) strain of *Toxoplasma gondii*. In a particular example, the *Toxoplasma* is a Type II mutant.

In one specific example, the TPS/TPP-like gene is disrupted by nucleotide insertion or deletion within the sequence of SEQ ID NO:1, SEQ ID NO:2 or SEQ ID NO:3 set forth as CCCGTCTCTGGGGAATTGGCAGGTGAGGCTGCGTCGCCGTCGCC (SEQ ID NO:4).

In a specific example, the mutant comprises a single C nucleotide insertion within the TPS/TPP-like gene according to SEQ ID NO:2 or SEQ ID NO:3, or the sequence set forth in SEQ ID NO:4. In a further specific example, the mutant comprises the sequence CCCGTCTCTGGGGAATTCGGCAGGTGAGGCTGCGTCGCCGTCGC (SEQ ID NO:5).

In another specific example, the mutant comprises a TPS/TPP-like gene sequence having an insertion of heterologous nucleotides, for example sequence derived from the CRISPR/cas9 plasmid used to generate the mutant.

In another specific example, the mutant comprises a 183 bp insertion of heterologous nucleotides within the TPS/TPP-like gene according to SEQ ID NO:2 or SEQ ID NO:3, or the sequence set forth in SEQ ID NO:4. In another specific example, the mutant comprises the sequence CCCGTCTCTGGGGAAA(+182)GGCAGGCAGGT-GAGGCTGCGTCGCCG (SEQ ID NO:6) wherein the mutant comprises the insertion of an A nucleotide plus an adjacent additional insertion of 182 contiguous heterologous nucleotides.

In another specific example, the mutant comprises the sequence CCCGTCTCTGGGGAATTTGA(>1000)TT-AGGCAGGTGAGGCTG (SEQ ID NO:8) wherein >1000 refers to the insertion of greater than 1000 contiguous heterologous nucleotides.

In another specific example, the mutant comprises a single T nucleotide deletion within the sequence of the TPS/TPP-like gene comprising a sequence set forth in SEQ ID NO:2, SEQ ID NO:3 or SEQ ID NO:4. In a further specific example, the mutant comprises the sequence CCCGTCTCTGGGGAATGGCAGGTGAGGCTGCGT-CGCCGTCGCC (SEQ ID NO:7).

In another specific example, the mutant comprises a deletion of nucleotide residues from position 48 to 115 of SEQ ID NO:1. In a further specific example, the mutant comprises the sequence GACAGACTTCGGTGAAC-GAGTCGCCTGCGCCGCTTCGTG (SEQ ID NO:9).

The present disclosure also provides a *Toxoplasma gondii* mutant deposited with the American Type Culture Collection, 10801 University Blvd., Manassas, Va. 20110-2209 on Sep. 14, 2018 and having the designation PTA-125165 (also referred to herein as RH:Dhxgprt:Dtps/tpp cl-23 (SEQ ID NO:7).

The present disclosure also provides a *Toxoplasma gondii* mutant deposited with the American Type Culture Collection, 10801 University Blvd., Manassas, Va. 20110-2209 on Sep. 14, 2018 and having the designation PTA-125166 (also referred to herein as Pru:tdTomato:TPS/TPP).

The present disclosure also contemplates mutant parasites comprising one or more additional gene activations, inactivations or disruptions in combination with the inactivated or disrupted TPS/TPP-like gene described herein, wherein starch accumulation is increased relative to wild-type parasites. In one example, the additional gene is the CDPK2 gene. Generation of parasites comprising an inactivation of the CDPK2 gene (Δcdpk2) is described in Uboldi A et al., (2015) Cell Host & Microbe 18,670-681). Thus, in one example the present disclosure provides a mutant parasite comprising or consisting of a mutation in the TPS/TPP-like gene and a mutation in the CDPK2 gene. In particular, the mutation is such that normal starch metabolism is compromised in the mutant parasite. In one example, the combination of mutations results in one or more of the following i) increase in size of amylopectin granules, ii) increase in number of amylopectin granules, or iii) more rapid accumulation of amylopectin granules.

In another example, the mutant parasite comprises or consist of a mutation in the TPS/TPP-like gene and a modified hexokinase (HxK) gene. In one example, the hexokinase is C-terminal modified as described herein. In one example, the mutant parasite comprises a modified C-terminus having the following sequence ADVNAGAGY-PYDVPDYAAGAGPRAGAGYPYDVPDYAAGAGPGD-VDIEL (SEQ ID NO:20).

In one example, the mutant parasite comprises or consists of a mutated TPS/TPP-like gene and a HA-tagged HxK gene (designated Δtps/tpp:HxK-HA).

The present disclosure also provides a *Toxoplasma gondii* mutant deposited with the American Type Culture Collection, 10801 University Blvd., Manassas, Va. 20110-2209 on Sep. 14, 2018 and having the designation PTA-125164 (also referred to herein as RH: Δhxgprt:Ku80:Δtps/tpp:HxK-HA cl-1 SEQ ID NO:9).

The skilled person will be familiar with methodologies that can be utilised to introduce a targeted or non-targeted (i.e. random) insertion or deletion of nucleotide residues within the TPS/TPP-like gene sequence. For example, targeted disruption of the TPS/TPP-like gene can be made using clustered regularly interspaced short palindromic repeats (CRISPR). If CRISPR is to be utilised, a proto-spacer sequence corresponding to about a 20 bp region of the target gene can be designed together with a proto-spacer adjacent motif of about 2-6 bp which includes a GG dinucleotide and which immediately follows the DNA sequence to be targeted. CRISPR methodology is known in the art and described for example in Shen B et al (2014) MBio 13; 5(3). In another example, disruption of the TPS/TPP-like gene is caused by homologous recombination. In yet another example, disruption of the TPS/TPP-like gene is caused by mutagenesis. In a still further example, disruption of the TPS/TPP-like gene is caused by knocking-out the gene. In yet another example, disruption of the TPS/TPP-like gene is caused by using a 'hit and run' strategy as described for example in Michel Cohen-Tannoudji and Charles Babinet (1998) Molecular Human Reproduction vol 4(10):929-938. Other methods known in the art for disrupting or inactivating a gene are considered to be within the scope of the present disclosure.

In a second aspect, the present disclosure provides a vaccine comprising the mutant parasite according to the first aspect of the disclosure. In one example, the vaccine comprises an isolated mutant intracellular parasite wherein the parasite uncontrollably accumulates starch-like amylopectin stores when grown in glucose-containing medium. In another example, the parasite is a protozoan parasite. In another example, the vaccine comprises a parasite having an inactivating mutation of the trehalose-6-phosphate synthase/6-phosphate phosphatase (TPS/TPP)-like gene.

In one example, the parasite is *Toxoplasma* or other parasite described herein.

In one example, the vaccine further comprises a pharmaceutically acceptable carrier or excipient.

In a further example, the mutant parasite is unable to persist in an animal vaccinated with the vaccine. For example, the mutant parasite is unable to remain viable in the vaccinated animal for more than 2-3 days.

In one example, oocyst shedding is prevented or substantially reduced in an animal vaccinated with the vaccine.

In one example, the mutant parasite is attenuated in vitro prior to administration to an animal by growth in glucose-containing medium. Such attenuation can be achieved by culturing the mutant parasite in glucose-containing media for a suitable period of time to permit the formation of starch granules in the parasite. In one example, the culture period is about 1-7 days, preferably about 1-2 days. In a further example, the culture period is about 24 hours.

In a third aspect, the present disclosure provides a method of vaccinating an animal against a parasite, comprising administering to the animal, a mutant parasite according to the first aspect or the vaccine comprising a mutant parasite according to the second aspect. In one example, the parasite is a protozoan parasite. In one example, the method is a method of vaccinating an animal against toxoplasmosis. In a further example, the method of vaccinating an animal against toxoplasmosis, comprises administering to the animal, a mutant *Toxoplasma* parasite according to the first aspect or the vaccine comprising a mutant *Toxoplasma* parasite according to the second aspect.

In one example, the vaccine is administered to the animal in an effective amount.

The animal to be vaccinated according to this aspect may be any warm blooded animal, and preferably an animal that is susceptible to toxoplasmosis. The warm-blooded animal may also include a member of the cat family (natural host for *Toxoplasma*).

In another example, the animal is selected from the group consisting of human, cattle, sheep, goat, bird, cat, pig, new-world monkey, Australian native marsupial, bear, deer or racoon. Examples of Australian native marsupials include the koala, kangaroo, wallaby, quokka, wombat, quoll, Tasmanian devil, brushtail possum, potoroo and dunnart.

In another example, the human is a non-pregnant female human.

In a fourth aspect, the present disclosure provides a method for vaccinating an animal against a parasitic infection or condition without concomitant oocyst shedding, comprising administering to the animal a mutant parasite according to the first aspect or the vaccine according to the second aspect. For example, the parasitic infection may include toxoplasmosis caused by *Toxoplasma* and the parasitic condition may include spontaneous abortion.

In one example, the disclosure provides a method for vaccinating an animal against toxoplasmosis without concomitant oocyst shedding, comprising administering to the animal a mutant *Toxoplasma* parasite according to the first aspect or the vaccine comprising a mutant *Toxoplasma* parasite according to the second aspect.

In one example, the animal is a cat e.g. domestic cat.

In certain examples, the vaccines of the disclosure protect against subsequent *Toxoplasma* challenge.

The vaccine may be administered to the animal in any suitable form including intra-muscular, subcutaneous and oral. In a particular example, the vaccine is administered orally.

In one example, the vaccine is administered together with a pharmaceutically acceptable carrier or excipient. In another example, the pharmaceutically acceptable carrier is saline.

The form (i.e. sexual stage) in which the parasite is administered to an animal may differ. For example, the vaccine may comprise mutant parasites in tachyzoite and/or bradyzoite form. In another example, the vaccine may comprise mutant parasites in oocyst form.

The vaccine dose administered to the animal will be at the discretion of the clinician or veterinarian depending on the size and weight of the animal. In certain examples, the vaccine dose comprises at least about 1,000-2,000 parasites (e.g. tachyzoites). In other examples, the vaccine dose may comprise at least about 1,500, 1,800, 2,200, 2,500, 5,000, 8,000 or 10,000 or greater parasites (e.g. tachyzoites) depending on the animal.

It will be appreciated that a vaccine provided in oocyst form will not require storage under refrigerated conditions (e.g. at a temperature between 2-8° C.). Accordingly, this facilitates convenient and cost-effective transportation of the vaccine to remote communities and allows for the vaccine to be transported without compromising the quality (i.e. potency) of the vaccine. In certain examples, the vaccine dose may comprise at least about 20 oocysts. In other examples, the vaccine comprises at least about 30, 40, 50, 60, 70, 80, 90, 100 oocysts. In yet another example, the vaccine comprises between 100 and 200 oocysts. In certain examples, the oocytes are provided together with a pharmaceutically acceptable diluent or excipient.

The vaccine may be administered to the animal in single or multiple doses.

In one example, the vaccine is administered to the animal prior to tupping or mating. In a further example, the vaccine is administered to the animal at least four weeks prior to tupping or mating.

In some examples, the vaccine may further comprise an adjuvant.

In certain examples, the vaccine is provided together with instructions for use. The instructions for use may require that the vaccine is reconstituted prior to administration to an animal for immunisation. For example, if the vaccine is provided in oocyst form, the vaccine may be provided with a suitable pharmaceutically acceptable diluent or excipient which is added to the oocysts prior to administration directly to the animal.

In certain examples, the oocysts can be cultured in a glutamine rich medium for a period of time sufficient to transform the oocysts to tachyzoites. In an example, the culture period is about 3-4 days. The tachyzoites can then be used to immunise an animal after being added to a suitable pharmaceutically acceptable diluent or excipient. The tachyzoites will naturally become attenuated following immunisation to the animal as the parasite will obtain its glucose source from the immunized host animal.

In an alternative example, the cultured tachyzoites can be attenuated in culture prior to administration to the animal by transferring the culture medium to medium comprising glucose or glucose and glutamine. The tachyzoites can then be cultured for a period of time to allow for the accumulation of starch granules with the parasite. In one example, this period of culture is about 1-2 days as above. Accumulation of starch granules in the parasites can be determined visibly by microscopy or Periodic-acid-Schiff (Pas) staining in a sample of the culture.

In a fifth aspect, the present disclosure provides for the use of a mutant parasite according to the first aspect or vaccine comprising a mutant parasite according to the second aspect in the manufacture of a medicament for vaccinating an animal. In one example, the medicament is for vaccinating an animal against toxoplasmosis.

In a particular example, the present disclosure provides for the use of a mutant *Toxoplasma* parasite according to the first aspect or the vaccine comprising a mutant *Toxoplasma* parasite according to the second aspect in the manufacture of a medicament for vaccinating an animal against toxoplasmosis.

In a sixth aspect, the present disclosure provides a mutant parasite according to the first aspect or vaccine comprising a mutant parasite according to the second aspect for use or when used in vaccinating an animal. In one example, the use is for vaccinating an animal against toxoplasmosis.

In a seventh aspect, the present disclosure provides a method of preventing toxoplasmosis in an animal, the method comprising administering to the animal a mutant *Toxoplasma* parasite according to the first aspect or a vaccine comprising a mutant *Toxoplasma* parasite according to the second aspect.

In an eighth aspect, the present disclosure provides oligonucleotide primers comprising or consisting of the sequence set forth in SEQ ID NO:10 and SEQ ID NO:11 for use in a method of disrupting the TPS/TPP-like gene of *Toxoplasma gondii*. In a particular example, the method is CRISPR/Cas9.

In a ninth aspect, the present disclosure provides a CRISPR/Cas9 method of disrupting the TPS/TPP-like gene of *Toxoplasma gondii* wherein the method comprises oligonucleotide primers comprising or consisting of the sequence set forth in SEQ ID NO:10 and SEQ ID NO:11.

In a tenth aspect, the present disclosure provides an oligonucleotide primer pair comprising or consisting of:
(i) SEQ ID NO:12 and SEQ ID NO:13;
(ii) SEQ ID NO:14 and SEQ ID NO:15; or
(iii) SEQ ID NO:16 and SEQ ID NO:17.

In an eleventh aspect, the present disclosure provides a kit comprising a first vessel containing mutant oocysts lacking a functional TPS/TPP-like gene, a second vessel containing a pharmaceutically acceptable excipient or diluent, a delivery device and instructions for use for combining the contents of the vessels and vaccinating an animal. In one example, the vessel is an ampoule or vial. In certain examples, the ampoule or vial includes a seal which can be punctured with a syringe. In a further example, the delivery device is a syringe for administration of the vaccine to an animal. In a further example, the mutant oocytes are *Toxoplasma* oocysts.

DESCRIPTION OF THE FIGURES

FIG. 1 shows the genomic sequence of the TPS/TPP-like gene from *T. gondii*. Introns are highlighted. The proto-spacer sequence is underlined followed by the AGG PAM sequence targeted by CRISPR.

FIG. 2 shows the N-terminal sequence of the TPS/TPP-like gene (first 200 nucleotides). The proto-spacer sequence and PAM sequences are indicated.

FIG. 3 shows A) the sequence of the wild-type (WT) TPS/TPP-like gene of *T. gondii* indicating the location of the proto-spacer sequence (bold and underlined text) and the PAM motif (highlighted). B) sequence of the RH:Δhxgprt:Δtps/tpp clone-1 having a single "C" nucleotide insertion. C) sequence of RH:Δhxgprt:Δtps/tpp clone-2 having a 183 bp insertion (A+182 bp) originating from the CRISPR/Cas9 plasmid. D) sequence of the RH:Δhxgprt:Δtps/tpp clone-23 having a single "T" base deletion. E) sequence of Pru:tdTomato:Δtps/tpp cl-2 having an insertion of greater than 1000 bp. F) sequence of RH:Δhxgprt:Δtps/tpp:Hexokinase-HA cl-1 having a 58 bp deletion, including the entire protospacer sequence and PAM motif.

FIG. 4 shows the genomic Sequence of *T. gondii* hexokinase (HxK). Introns are highlighted.

FIG. 6 shows A) Intracellular RH:Δtps/tpp tachyzoites hyperaccumulate amylopectin, B) detected with PAS stain when cultivated in the presence of medium containing glucose.

FIG. 7 shows A) total amylopectin pool and B) $^{13}$C-glucose levels in isolated parental RH and RH: Δtps/tpp tachyzoites were measured after extraction, amylase digestion and GC/MS.

FIG. 9 shows A) Glucose uptake by parental RH and RH:Δtgtps/tpp tachyzoites using $^{14}$C-glucose. B) Kinetics of turnover of intracellular pools of glucose-6-phosphate were assessed by labeling parasites with $^{13}$C-glucose and following incorporation of $^{13}$C into glucose-6-phosphate by GC/MS.

Figure 5:
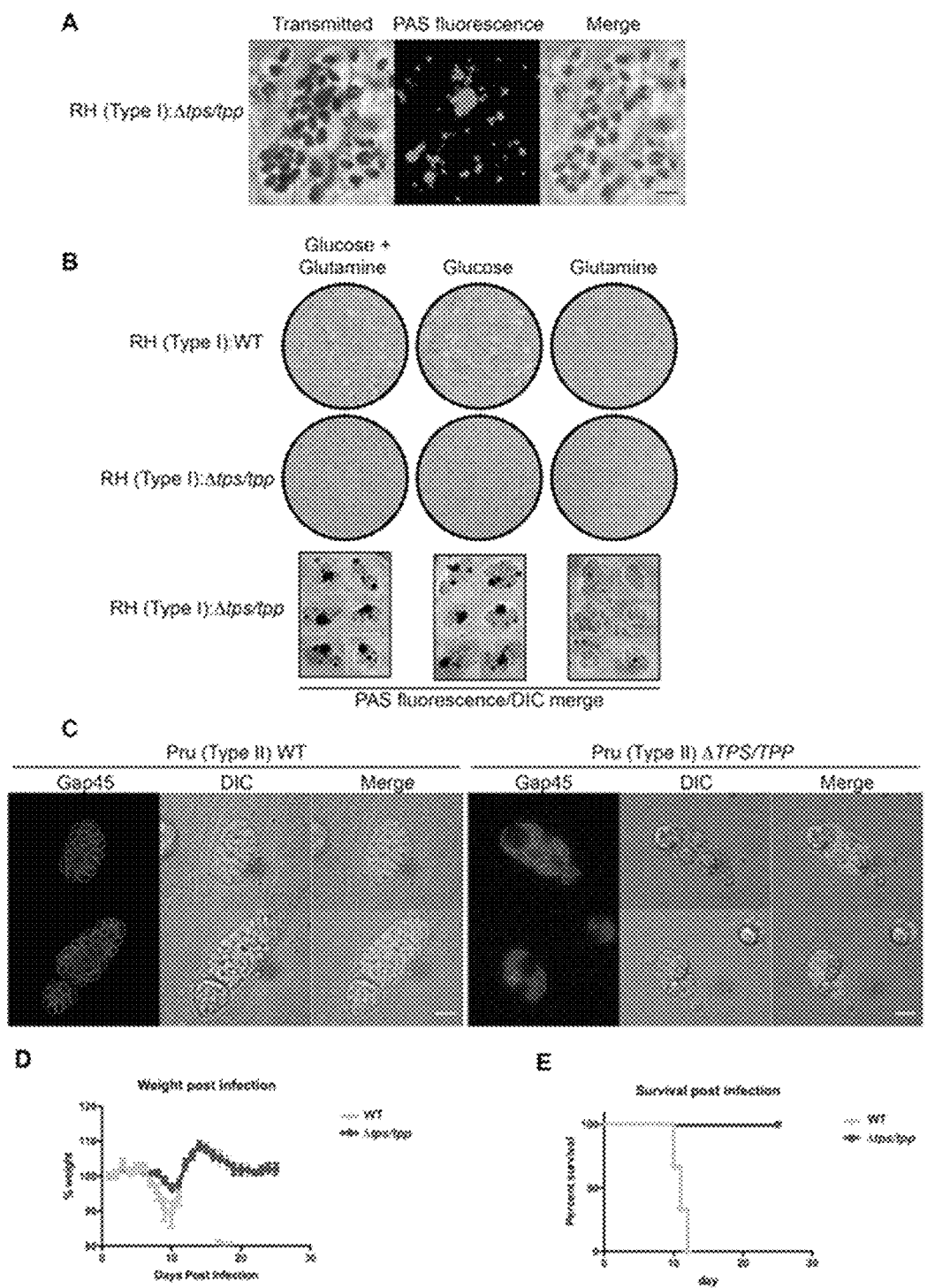
FIG. 5 shows that that Δtps/tpp parasites grown in glucose-containing medium accumulate amylopectin and exhibit reduced virulence in vivo. A) RH:Δtps/tpp parasites accumulate large amounts of amylopectin. Amylopectin was detected by periodic acid-Schiff fluorescence. Scale bar=5 μm. B) Plaque assays indicate that RH:Δtps/tpp parasites are defective for growth on glucose. Pas fluorescence shows the accumulation of amylopectin in glucose-containing medium compared to no or low amylopectin levels when grown in glucose-free, glutamine-containing medium. C) Type II Pru:tdTomato:Δtps/tpp parasites hyper-accumulate amylopectin in glucose-containing medium leading to morphological aberrations. Pru: tdTomato:Δtps/tpp parasites were generated in medium lacking glucose, before switching to glucose-containing medium. GAP45 staining, detected by IFA with anti-Gap45 antibodies, indicates the parasite periphery. Scale bars represent 10 μm. D) C57BL/6 mice infected with wild-type Pru:tdTomato parasites lost significant body weight over time, with loss peaking at 10 days-post infections. In contrast, the mice infected with Pru:tdTomato:Δtps/tpp parasites did not lose body weight E) At around 10 days-post infection, C57BL/6 mice infected with wild-type Pru parasites rapidly succumbed to the infection. In contrast, the mice infected with Pru:tdTomato:Δtps/tpp parasites remained healthy over the duration of the experiment. C57BL/6 mice were inoculated with 10000 Pru:tdtomato:Δtps/tpp or WT parasites and their change in body mass and survival were monitored over time.

The bradyzoite surface protein SRS9 was detected with anti-SRS9 antibodies, while amylopectin was detected via PAS staining. The scale bar represents 5 μm.

FIG. 17 Immunization with ATPS/TPP *Toxoplasma* protects against subsequent challenge. Naïve and ΔTPS/TPP immunized animals were challenged with 1×10⁴ wildtype (PruΔhx) *Toxoplasma* tachyzoites i.p. A) Body weight was monitored daily and B) Kaplan-Meier survival curves generated. Animals were culled when they had dropped 10% body weight for more than three consecutive days or 15% for more than one day.

KEY TO SEQUENCE LISTING

SEQ ID NO:1: shows the genomic sequence of the TPS/TPP-like gene from *T. gondii*.
SEQ ID NO:2: shows the N-terminal sequence of the TPS/TPP-like gene (first 200 nucleotides).
SEQ ID NO:3: shows the cDNA sequence of the TPS/TPP-like gene from *T. gondii*.
SEQ ID NO:4: sequence of a N-terminal portion of the wild-type TPS/TPP-like gene from *T. gondii* targeted for CRISPR including the 20 bp WT protospacer sequence and PAM motif.
SEQ ID NO:5: shows a sequence of a portion of the mutated TPS/TPP-like gene from *T. gondii* containing a single C insertion at residue 18 (FIG. 3B).
SEQ ID NO:6: shows a sequence of a portion of the mutated TPS/TPP-like gene from *T. gondii* containing an insertion of heterologous nucleotides following residue 15 (FIG. 3C).
SEQ ID NO:7: shows a sequence of a portion of the mutated TPS/TPP-like gene from *T. gondii* containing a deletion of a single T nucleotide (3D).
SEQ ID NO:8: shows a sequence of a portion of the mutated TPS/TPP-like gene from *T. gondii* containing an insertion of greater than 1000 nucleotides following residue 20 (FIG. 3E).
SEQ ID NO:9: shows a sequence of a portion of the mutated TPS/TPP-like gene from *T. gondii* which has a 58 bp deletion including the entire protospacer sequence and PAM motif (FIG. 3F).
SEQ ID NO:10: shows the sequence of an oligonucleotide primer.
SEQ ID NO:11: shows the sequence of an oligonucleotide primer.
SEQ ID NO:12: shows the sequence of an oligonucleotide primer.
SEQ ID NO:13: shows the sequence of an oligonucleotide primer.
SEQ ID NO:14: shows the sequence of an oligonucleotide primer.
SEQ ID NO:15: shows the sequence of an oligonucleotide primer.
SEQ ID NO:16: shows the sequence of an oligonucleotide primer.
SEQ ID NO:17: shows the sequence of an oligonucleotide primer.
SEQ ID NO:18: shows the sequence of a mutant comprising a 183 bp insertion sequence within SEQ ID NO:4.
SEQ ID NO:19: shows the sequence of a mutant comprising a >1 kb insertion sequence (partial sequence obtained) disrupting the TPS/TPP locus in SEQ ID NO:8.
SEQ ID NO:20: shows the sequence of the HA-tagged hexokinase modified C-terminus.
SEQ ID NO:21: shows the the 58 bp deletion sequence from SEQ ID NO:9.
SEQ ID NO:22: shows the sequence of the 20 bp protospacer.
SEQ ID NO:23: shows the genomic sequence of hexokinase gene from *T. gondii*.
SEQ ID NO:24: sequence of gBlock No. 1.
SEQ ID NO:25: sequence of gBlock No. 2.
SEQ ID NO:26: sequence of gBlock No. 3.
SEQ ID NO:27: sequence of gBlock No. 4.
SEQ ID NO:28: sequence of gBlock No. 5.
SEQ ID NO:29: sequence of gBlock No. 6.
SEQ ID NO:30: sequence of gBlock No. 7.
SEQ ID NO:31: sequence of gBlock No. 8.
SEQ ID NO:32: sequence of gBlock No. 9.
SEQ ID NO:33: sequence of gBlock No. 10.
SEQ ID NO:34: sequence of forward primer.
SEQ ID NO:35: sequence of reverse primer.
SEQ ID NO:36: sequence of forward primer.
SEQ ID NO:37: sequence of reverse primer.
SEQ ID NO:38: sequence of forward primer.
SEQ ID NO:39: sequence of reverse primer.
SEQ ID NO:40: sequence of forward primer.
SEQ ID NO:41: sequence of reverse primer.
SEQ ID NO:42: sequence of forward primer.
SEQ ID NO:43: sequence of reverse primer.
SEQ ID NO:44: sequence of reverse primer.
SEQ ID NO:45: sequence of forward primer.
SEQ ID NO:46: sequence of forward primer.
SEQ ID NO:47: sequence of short linker.
SEQ ID NO:48: sequence of long linker.
SEQ ID NO:49: sequence of forward primer.
SEQ ID NO:50: sequence of forward primer.
SEQ ID NO:51: sequence of reverse primer.
SEQ ID NO:52: sequence of forward primer.
SEQ ID NO:53: sequence reverse primer.
SEQ ID NO:54: sequence of reverse primer.
SEQ ID NO:55: sequence of forward primer.
SEQ ID NO:56: oligonucleotide sequence.
SEQ ID NO:57: oligonucleotide sequence.
SEQ ID NO:58: oligonucleotide sequence.
SEQ ID NO:59: oligonucleotide sequence.
SEQ ID NO:60: oligonucleotide sequence.
SEQ ID NO:61: oligonucleotide sequence.
SEQ ID NO:62: oligonucleotide sequence.
SEQ ID NO:63: oligonucleotide sequence.

DETAILED DESCRIPTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, Perbal (1984), Sambrook et al., (1989), Brown (1991), Glover and Hames (1995 and 1996), and Ausubel et al., (1988, including all updates until present), Harlow and Lane, (1988), Coligan et al., (including all updates until present) and Zola (1987).

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

The present invention employs conventional molecular biology, microbiology and recombinant DNA techniques within the skill of the art. See for example, Sambrook et al "Molecular Cloning" A Laboratory Manual (1989).

Selected Definitions

The term "and/or", e.g., "X and/or Y" shall be understood to mean either "X and Y" or "X or Y" and shall be taken to provide explicit support for both means or for either meaning.

Reference to the singular forms "a", "an" and "the" is also understood to imply the inclusion of plural forms unless the context dictates otherwise.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent (%), up or down (higher or lower).

By "isolated" it is meant a parasite that is removed from its native environment. In a particular example, it refers to a mutant parasite whose genotype is altered relative to the native parasite.

The term "disruption" as used herein refers to a gene (e.g. the TPS/TPP-like gene) whose native sequence has been modified through insertion or deletion of nucleotides within the sequence. The insertion or deletion may encompass a single nucleotide or up to thousands of nucleotides within the target sequence. The nucleotides being inserted or deleted may be continguous, partially contiguous or non-contiguous. The term "disruption" is understood to encompass mutations which are introduced at a particular nucleotide location within a sequence or directed to occur within a particular region of nucleotides targeted for mutation. Non-targeted disruptions which are also encompassed by the term "disruption" are understood to refer to randomly introduced mutations into a sequence, meaning that the mutation is introduced at a random location (which is not predetermined) within a given sequence. The CRISPR-derived mutations described herein are generally understood in the art to refer to a targeted mutations. While it cannot be predicted whether the CRISPR repair mechanism with result in an insertion or deletion of nucleotides, the proto-spacer and PAM motif are used to direct the mutations to a particular location within a sequence (e.g. the TPS/TPP-like gene described herein).

The term "knock-out" as referred to herein refers to a process in which a part or all of a gene is replaced or disrupted with an artificial piece of DNA such as DNA from *Toxoplasma* or another organism or from the Cas9 and RNA guide containing plasmid used for transfection.

The term "native TPS/TPP-like gene" as used herein refers to a gene having both trehalose phosphate synthase (TPS) and trehalose 6-phosphate phosphatase (TPP) domains arranged in tandem, as well as an N-terminal amylopectin-binding CBM20 domain. Said gene is that in the form in which it naturally occurs in a given parasite. For example, the native TPS/TPP-like gene sequence in *Toxoplasma* can be derived from the ToxoDB Gene ID TGGT1_297720 (shown in FIG. 1) in the *Toxoplasma* Genomics Resource (www.Toxodb.org).

The term "inactivating mutation" as referred to herein refers to a mutation which negatively affects transcription of a given gene so that the resulting protein cannot be produced. Inactivating mutations can be produced by different means, for example deletion of native nucleotides or insertion of heterologous nucleotides within the gene sequence. An inactivating mutation can also be caused by an insertion or deletion that results in a frame shift in the gene sequence compared to the native sequence.

The term "homolog thereof" of a TPS/TPP-like gene refers to a gene sequence that is genetically related to a TPS/TPP-like gene designated ToxoDB Gene ID TGGT1_297720 (shown in FIG. 1). In the context of the present disclosure it refers to other TPS/TPP-like gene present in other parasitic organisms beyond *Toxoplasma* where such parasites also store energy as amylopectin. Such homologs may comprise a sequence that is at least 70%, at least 75%, at least 80%, at least 85%, at least 90%, at least 92%, at least 95%, at least 97%, at least 98%, at least 99% identical to the TPS/TPP-like gene of *T. gondii*.

The term "Coccidia" as used herein refers to an obligate intracellular parasite belonging to the apicomplexan class. Such parasites must live and reproduce within an animal cell.

The term "composition", as used herein, means any composition, which contains at least one therapeutically or biologically active agent and is suitable for administration to a subject. Any of these formulations can be prepared by well-known and accepted methods of the art. See, for example, Gennaro, A. R., ed., Remington: The Science and Practice of Pharmacy, 20th Edition, Mack Publishing Co., Easton, Pa. (2000).

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

The term "animal" as used herein refers to any warm-blooded animal, including non-human animals (e.g. cat, sheep) or primate (e.g. human or monkey).

The term "vaccinating" as used herein refers to a process of inducing immunity to an infectious organism in an animal through immunization. Typically, immunisation of an animal is designed to provide protection against further challenge with the same infectious organism (i.e. immunogen) by stimulating the animal's immune system.

The term "proto-spacer adjacent motif (PAM)" sequence refers to a 2-6 base pair DNA sequence immediately following the DNA sequence targeted by the Cas9 nuclease in the CRISPR system. Cas9 will not successfully bind to or cleave the target DNA sequence if it is not followed by the PAM sequence. The canonical PAM sequence is 5'-NGG-3' wherein N is any nucleobase followed by two guanine (G) nucleobases.

The term "uncontrolled" should be given its ordinary meaning. Its understood to mean growth that occurs in a unrestrained manner.

The term "*Toxoplasma*" as used herein is understood to refer to *Toxoplasma gondii* and the terms can be used interchangeably.

Lifecycle of *Toxoplasma gondii* (*T. gondii*)

*Toxoplasma* primarily exists in three forms that are infective to humans and animals, oocysts (containing sporozites), tachyzoites and bradyzoites. All three stages are infectious for both intermediate and definitive hosts which may acquire a *Toxoplasma* infection mainly via one of the following routes: (A) horizontally by oral ingestion of infectious oocysts from the environment, (B) horizontally by oral ingestion of tissue cysts contained in raw or undercooked meat or primary offal (viscera) of intermediate hosts, or (C) vertically by transplacental transmission of tachyzoites. In addition, in several hosts tachyzoites may also be transmitted in the milk from the mother to the offspring.

Oocysts are thought to be only produced in the definitive host, members of the family Felidae. When passed in faeces, the oocysts can infect humans and other intermediate hosts (essentially any warm blooded animal). They then develop into tachyzoites which multiply rapidly by repeated endodyogeny. They divide rapidly in cells, causing tissue destruction and spreading the infection. Eventually tachyzoites localise to muscle tissues and the CNS where they convert to tissue cysts, or bradyzoites. This is thought to be a response to the host immune reaction.

Tissue cysts (containing bradyzoites) have a high affinity for neural and muscular tissues. They are located predominantly in the central nervous system (CNS), the eye, as well as skeletal and cardiac muscles. However, to a lesser extent they may also be found in visceral organs, such as lungs, liver, and kidneys. Tissue cysts are the terminal life-cycle stage in the intermediate host and are immediately infectious. In some intermediate host species, they may persist for the life of the host. The mechanism of this persistence is unknown. However, many investigators believe that tissue cysts break down periodically, with bradyzoites transforming to tachyzoites that reinvade host cells and again transform to bradyzoites within new tissue cysts (Dubey J P et al. (1998) Clin Microbiol. Rev 11:267-99).

Ingestion of cysts in contaminated meat results in the bradyzoites transforming back into tachyzoites upon entering the new host.

*Toxoplasma* was first recognised to be an important pathogen in livestock species following reports from New Zealand describing *Toxoplasma* organisms in placental tissue from aborting sheep and within an aborted ovine foetus (Hartley et al. (1954) Aust Vet J 30: 216-218, Hartley & Marshall, (1957) NZ Vet J 5: 119-124). The discovery in the late 1960's that cats could shed a new form of the parasite in their faeces that was very stable in the environment led to the recognition of the cat as the definitive host of the parasite.

Virtually all edible portions of an animal can harbor viable *Toxoplasma*. In one study, viable *Toxoplasma* was isolated from 17% of 1,000 adult pigs (sows) from a slaughter plant in Iowa. *Toxoplasma* infection is also prevalent in game animals. Among wild game, *Toxoplasma* infection is most prevalent in black bears and in white-tailed deer. Approximately 80% of black bears are infected in the U.S., and about 60% of raccoons have antibodies to *Toxoplasma* Because raccoons and bears scavenge for their food, infection in these animals is a good indicator of the prevalence of *Toxoplasma* in the environment.

The number of *Toxoplasma* tissue cysts in meat from food animals is very low. It is estimated that as few as 1 tissue cyst may be present in 100 grams of meat.

*Toxoplasma* parasites suitable for use in the present disclosure can be obtained from a depository such as the American Type Culture Collection (ATCC). The ATCC includes multiple deposits of *Toxoplasma*, for example ATCC Number PRA-340, PRA-426, PRA-344, 50950, 50174, 40050, 50839, 50940, 50611, 40615, 50943, 50942, 50856, 50851 and 50947.

Energy Utilisation of *Toxoplasma gondii* (*T. gondii*)

*Toxoplasma* tachyzoites must salvage carbon sources and other essential nutrients from their host cell. *Toxoplasma* reside within a unique parasitophorous vacuole in infected host cells that is surrounded by membrane that is thought freely permeable to many host metabolites.

To derive its energy, tachyzoites utilise both glucose and glutamine scavenged from the host cell (MacRae J I et al. (2012) Host Cell Microbe 12:682-692) and following host cell egress, tachyzoites accumulate γ-aminobutyric acid which may provide extracellular tachyzoites with a short term energy reserve to fuel motility and invasion (MacRae J I et al. (2012) Host Cell Microbe 12:682-692). *Toxoplasma* tachyzoites also produce the storage polysaccharide amylopectin which contains a backbone of α(1-4)-linked glucose residues modified with α(1-6)-linked branch points. Tachyzoites generally express very low levels of amylopectin unless stressed, in contrast bradyzoites and oocytes accumulate high levels of amylopectin granules in the cytoplasm (Coppin A et al. (2003) Biochimie 85:353-361). It has been postulated that amylopectin granules may be a long-term energy storage during transmission to maintain parasite viability in low-nutrient niches and/or to drive rapid differentiation when they encounter favourable conditions. However, little is known about how amylopectin accumulation and utilisation is regulated in different *Toxoplasma* life cell stages.

Amylopectin Characterisation

Structural and gas chromatography/mass spectroscopy analysis has determined that the granules in *Toxoplasma* are genuine amylopectin composed of α(1-4)-linked glucan linear chains with a low proportion of α(1-6) branches. The chains have an average length of 19 glucose molecules (Guerardel Y et al (2005) Microbes Infect 7(1):41-8).

Amylopectin is found in all stages of *Toxoplasma*. However, it has been experimentally shown that conversion of dormant encysted bradyzoites into newly transformed tachzyoites correlates with the disappearance of amylopectin granules (Coppin A et al. (2003) Biochimie 85:353-361). In *Toxoplasma*, during tissue cyst formation, there is synthesis of numerous (average: 21.8, range: 7-38) amylopectin granules within the bradyzoite at an average size of 358 nm (range: 192-630 nm) and the presence of specific lectin binding sugars in the cysts well (Von Brand, 1973). The bradyzoite form produces an extraordinarily high amount of amylopectin (glucose polymer) while it develops in glucose rich environments such as brain or muscle cells because of the decreased need for nutrients during this inactive period.

Amylopectin granules have been found to be present in a considerable range of sizes. The large amylopectin granules exhibit a rigid compact coiled ball of string structure to store large amounts of glucose molecules and have dimensions of the order of 0.4 μm. The neatly coiled, smooth-surfaced 'ball of string' structure of the larger amylopectin granules markedly with the more irregular shape and rod-like particulate composition of the smaller granules (Harris J R et al., (2004) Parasitology 128(Pt 3):269-82). Amylopectin granules can be identified using techniques such as iodine staining, periodic-acid Schiff staining or electron microscopy amongst others.

Trehalose-6-Phosphate Synthase/6-Phosphate Phosphatase (TPS/TPP)-Like Gene

Many fungi and plants synthesize the disaccharide, trehalose, via the concerted actions of the two enzymes, trehalose phosphate synthase (TPS) and trehalose phosphate phosphatase (TPP) (Thammahong A et al., (2017) Microbiol Mol Biol Rev 15; 81(2)). Trehalose synthesis is often increased under conditions of cellular stress, reflecting the potential role of this sugar as a short term energy reserve and as a compatible solute, stabilizing proteins in vivo. In addition, the constitutive synthesis and degradation of trehalose via an ATP-consuming futile cycle, may have a critical role in balancing fluxes through upper (ATP consuming) and lower (ATP generating) glycolysis in some fungi. Intriguingly, the genomes of all strains of *T. gondii* encode a protein which contains both TPS and TPP domains (toxodb accession no. TGME49_297720).

Both TPS and TPP proteins, and the trehalose biosynthetic pathway in which they function, are not present in mammalian cells. The *Toxoplasma* homologue (referred to herein as the TPS/TPP-like gene) contains both trehalose 6-phosphate synthase (TPS)-like and trehalose 6-phosphate phosphatase (TPP)-like domains arranged in tandem, as well as an N-terminal amylopectin-binding CBM20 domain, allowing for direct interaction with amylopectin.

Initial sequence analysis indicated that the TPS domain of *Toxoplasma gondii*, TgTPS/TPP shared strong homology with TPS proteins from *E. coli*, *S. cerevisiae* and *A. thaliana*, including residues important for binding the UDP-glucose donor. However the *Toxoplasma* TPS domain lacked several residues that are important TPS catalysis, including Gly22, Val366 and Lys267 (important for UDP-glucose binding) and Arg9, Arg300 and Tyr76 (important for glucose-6-phosphate binding), raising the possibility that this domain may not have T6P synthase activity. Similarly, while the C-terminal TgTPP-like domain appears to possess all the conserved motifs necessary for phosphatase activity, the TgTPP sequence contains additional insertions that may interfere with activity. Consistent with the possibility that the TgTPS/TPP lacks either trehalose phosphate synthase or trehalose-phosphate phosphatase activity, neither trehalose or trehalose phosphate could be detected in total cell extracts of tachyzoites using either GC/MS and LC/MS.

The tandem arrangement of TPS-like and TPP-like domains is also present in 11 paralogs found in *Arabidopsis* (Vandesteene L et al., (2012) Plant physiology 160:884-896), although only three of these have been shown to have T6P synthase activity (Vandesteene et al., (2012) and Delorge I et al., (2015) The Biochemical Journal 466:283-290) and none of these have been shown to have T6P phosphatase activity.

In addition to the dual domain proteins, *Arabidopsis* contains 10 proteins that contain an enzymatically active T6P phosphatase domain, but lack the TPS-like domain altogether (Vogel G et al., (1998) The Plant Journal: for cell and molecular biology 13:673-683). In yeast, the TPS and TPP proteins are separate, but form a complex with two additional accessory proteins (Bell W et al., (1992) European Journal of Biochemistry 209:951-959; Bell W et al., (1998) The Journal of Biological Chemistry 273:33311-33319; Vuorio 0. E et al., (1993) European Journal of Biochemistry 216:849-861). Importantly, the *S. cerevisiae* yeast homolog TPS1 is required for growth on glucose and disruption of this gene leads to accumulation of G6P (Eastmond P. J. and Graham I. A. et al., (2003) Current opinion in plant biology 6:231-235; Hohmann S. et al (1996) Molecular Biology 20:981-991). At least some *Arabidopsis* paralogs are also involved in sugar signalling and plant development (Eastmond P. J. et al., (2002) The Plant Journal: for cell and molecular biology 29:225-235; Gomez L. D. et al., (2006) The Plant Journal: for cell and molecular biology 46:69-84; Gomez L. D. et al., (2010) The Plant Journal: for cell and molecular biology 64:1-13; van Dijken A. J. et al., (2004) Plant physiology 135:969-977).

The sequence of the TPS/TPP-like gene in *T. gondii* is identified as ToxoDB Gene ID TGGT1_297720, the sequence of which is shown in FIG. 1 (SEQ ID NO:1). The ToxoDB gene resource is described in Gajria B et al., (2008) Nuc Acids Res 36(database issue):D553-D556.

Disrupting the TPS/TPP-Like Gene

As described herein, the present disclosure is directed to mutant parasites having a TPS/TPP-like gene which is disrupted resulting in gene inactivation. Inactivation of the TPS/TPP-like gene in the parasite can be effected by a number of different methods which are known in the art. The present disclosure is based on the finding that inactivation of the TPS/TPP-like gene in *Toxoplasma* results in amylopectin accumulation in the mutant parasites when grown in glucose-containing but not glucose-free medium.

A mutant of the present disclosure can be generated using any suitable method conventionally employed for producing gene knockout mutants. For example, a mutant can be obtained by single cross-over integration (e.g. as described in Fox and Bzik (2002) Nature 451(6874):926-9) or using a double cross-over gene replacement (Kim K et al., (1993) Science November 5; 262(5135):911-4).

In general, the generation of mutant *Toxoplasma* includes isolating the nucleic acid molecule of interest from *Toxoplasma* (e.g., as described herein); replacing, mutating, substituting or deleting all or a portion (e.g., one or more bp) of the gene to disrupt the coding or regulatory regions of the gene; and integrating the disrupted molecule into the genome of *Toxoplasma*. Using an appropriate drug-selectable marker e.g hxgprt, chloramphenicol acetyl transferase, DHFR-ts, or phleomycin, the mutant bearing the mutated sequence can be selected.

In particular embodiments, the selectable marker is selected for by positive and negative selection (e.g., HXGPRT).

Disruption of all or a portion of the TPS/TPP-like gene can be achieved by, e.g., replacing the coding sequence with a nucleic acid molecule encoding selectable marker, replacing the coding sequence with a nucleic acid molecule encoding an exogenous protein, etc. As is known to the skilled artisan, subsequent restriction endonuclease digestion and Southern blot analysis or sequencing of the mutant Toxoplasma genomic DNA can be used to confirm the disruption.

While mutants of the present invention can be produced from a virulent type I strain such as RH (as exemplified herein), a type II strain (as exemplified herein) as well as a type III strain can also be employed as well as any other strains belonging to Clades, A, B, C, D, E or F. A mutant of the present invention can alternatively be generated using Clustered Regularly Interspaced Short Palindromic Repeats (CRISPR) as described (Shen Z et al., (2014) Dev Cell September 8; 30(5):625-36; Sidik S. M. et al PLoS One 2014 Jun. 27; 9(6):e100450 PMID:24971596). Briefly, the technology consists of a guide RNA (gRNA) and a DNA endonuclease, Cas9 (typically from *Streptococcus pyogenes*). The gRNA (or protospacer sequence) determines where insertions or deletions (indels) will occur. Once the gRNA and Cas9 are expressed in cells, the gRNA will direct Cas9 to bind to the target sequence and introduce a double-strand break. The cell can then repair the break with either non-homologous end joining (NHEJ) or homologous directed repair (HDR). NHEJ is the most active repair mechanism in *Toxoplasma* and often leads to indels near the target sequence. If the insertion or deletion occurs within the open reading frame, it may introduce a frameshift that causes a premature stop codon, eliminating the gene function. If a homologous template is provided then HDR recombination can occur and also lead to the disruption or modification of the gene. In the current technology (Shen et al 2014 and Sidik et al 2014) guide sequences/protospacers are selected based on being adjacent to an PAM 'NGG' motif and consisting of 20 bps. A 'G' can be added to the 5' end to better initiate transcription. Protospacer sequences and their adjacent PAM motifs can be selected on either DNA strand, throughout the whole gene including promoters, terminators, coding sequence or introns or any other part of the gene that could affect the levels or fidelity of the gene product.

As described herein, by way of non-limiting example, mutant parasites can be generated by using mutagenesis to replace the UPRT proto-spacer sequence of plasmid pSAG1-Cas9-U6-sgUPRT with the target TPS/TPP proto-spacer sequence (SEQ ID NO:22) and transfecting the construct into the parasites to initiate the CRISPR/Cas9 protocol. Screening of mutants can be achieved for example using Fluorescence activated cell sorting (FACS) to sort the parasites into the wells of a 96 well microplate and then culturing for a period of time sufficient to identify clones that produced visible starch granules (amylopectin) when grown in glucose containing medium. Once a mutant clone is identified it can be maintained in glucose-free medium but containing glutamine to propagate the parasite until such time as it is required for vaccination. Mutants can also be isolated by initially growing transfected cells in glutamine media, cloning these out by limited dilution and then identifying those that are mutants by looking for the production of amylopectin when transferred to glucose-containing media.

Preferably, the mutant parasites of the invention are attenuated when grown in glucose-containing medium. As conventional in the art, the term "attenuated" refers to a weakened and/or less vigorous version of the native strain. Desirably, the attenuated mutant of the invention is capable of stimulating an immune response and creating immunity but not causing illness. Attenuation can be determined using methods as shown herein in the examples. In some examples, the extent of attenuation is at least 50%, at least 60%, at least 70%, at least 80%, at least 90% at least 95%, or greater than 95% relative to the corresponding wild-type parasite grown in the same medium.

Determining TPS/TPP-Like Gene Inactivation

Inactivation of the TPS/TPP-like gene can be assessed by examining amylopectin production by the mutant parasite in glucose-containing and glutamine-containing medium. For example, growth of mutant parasites can be assessed by plaque assays known in the art and as described herein. Plaque assays can be performed by assessing the growth capacity through the lytic cycle on confluent layers of human foreskin fibroblasts in medium containing either glucose or glutamine as a carbon source. Inactivation of the TPS/TPP-like gene will be evident by the accumulation of amylopectin granules in the tachyzoites themselves which can be observed by Pas staining. Growth of the same mutant parasite on glutamine containing medium should be comparable to wild-type parasites and if such mutant parasites are transferred to a glutamine containing medium, this should result in the disappearance or reduction of amylopectin granules in the parasites.

Virulence assays in mice can be performed as described herein. Survival and body weight of mice transfected with the mutant parasites can be measured over time. Mutants in which the TPS/TPP-like gene is inactivated will not significantly affect mice body weight over time compared to wild-type parasites which will result in loss of body weight in the mice and susceptibility to infection.

Vaccines

The present disclosure encompasses vaccines comprising the mutant parasites described herein. Preferably, the vaccine also includes a pharmaceutically acceptable excipient or diluent. The skilled person will know which appropriate excipient or diluent to use depending upon whether the vaccine is intended for human or veterinary use.

Administration of a mutant parasite disclosed herein can be carried out by any suitable means, including parenteral injection (such as intraperitoneal, subcutaneous, or intramuscular injection), orally, or by topical application (typically carried in a pharmaceutical formulation) to an airway surface. Topical application to an airway surface can be carried out by intranasal administration (e.g., by use of dropper, swab, or inhaler which deposits a pharmaceutical formulation intranasally). Oral administration can be in the form of an ingestible liquid or solid formulation.

In one example, the pharmaceutically acceptable excipient or diluent is an aqueous carrier. A variety of aqueous carriers can be used, e.g., buffered saline and the like. Exemplary carriers include water, saline, Ringer's solution, dextrose solution, and 5% human serum albumin. The compositions may contain pharmaceutically acceptable carriers as required to approximate physiological conditions such as pH adjusting and buffering agents, toxicity adjusting agents and the like, for example, sodium acetate, sodium chloride, potassium chloride, calcium chloride, sodium lactate and the like. Non-aqueous vehicles such as mixed oils and ethyl oleate may also be used. The vehicles may contain minor amounts of additives that enhance isotonicity and chemical stability, e.g., buffers and preservatives.

The vaccines of the present invention can include one or more veterinary-acceptable carriers. As used herein, "a veterinary-acceptable carrier" includes any and all solvents, dispersion media, coatings, adjuvants, stabilizing agents, diluents, preservatives, antibacterial and antifungal agents, isotonic agents, adsorption delaying agents, and the like. Diluents can include water, saline, dextrose, ethanol, glycerol, and the like. Isotonic agents can include sodium chloride, dextrose, mannitol, sorbitol, and lactose, among others. Stabilizers include albumin, among others. Adjuvants include, but are not limited to, the RIBI adjuvant system (Ribi Inc.), alum, aluminum hydroxide gel, Cholesterol, oil-in water emulsions, water-in-oil emulsions such as, e.g., Freund's complete and incomplete adjuvants, Block co-polymer (CytRx, Atlanta Ga.), SAF-M (Chiron, Emeryville Calif.), AMPHIGEN® adjuvant, saponin, Quil A, QS-21 (Cambridge Biotech Inc., Cambridge Mass.), GPI-0100 (Galenica Pharmaceuticals, Inc., Birmingham, Ala.) or other saponin fractions, monophosphoryl lipid A, Avridine lipid-amine adjuvant, heat-labile enterotoxin from *E. coli* (recombinant or otherwise), cholera toxin, or muramyl dipeptide, among many others.

Administration can be given in a single dose schedule, or a multiple dose schedule in which a primary course of treatment can be with 1-10 separate doses, followed by other doses given at subsequent time intervals required to maintain and or reinforce the response, for example, at 1-4 months for a second dose, and if needed, a subsequent dose(s) after several months Vaccine efficacy can be affected by a number of factors including the health status of the animal, genetic constitution, inter-current infection, age, nutritional status, current drug therapy and stress. Thus, in some examples it may be necessary to administer a further booster vaccine as described above.

The exact dosage for administration can be determined by the skilled practitioner, in light of factors related to the animal that requires prevention or treatment. Dosage and administration are adjusted to provide sufficient levels of the mutant parasite or vaccine containing same or to maintain the desired effect of preventing or reducing signs or symptoms of toxoplasmosis. Factors which may be taken into account include the severity of the disease state, general health of the subject, age, weight, and gender of the animal, diet, time and frequency of administration, drug combination(s), reaction sensitivities, and tolerance/response to therapy.

In certain examples, the vaccine dose comprises at least about 1,000-2,000 parasites (e.g. tachyzoites). In other example, the vaccine dose may comprise at least about 1,500, 1,800, 2,200, 2,500, 5,000, 8,000 or 10,000 or greater parasites (e.g. tachyzoites) depending on the animal.

In certain examples, the vaccine dose may comprise at least about 20 oocysts. In other examples, the vaccine comprises at least about 30, 40, 50, 60, 70, 80, 90, 100 oocysts. In yet another example, the vaccine comprises between 100 and 200 oocysts.

Uses of the Mutant *Toxoplasma gondii* (*T. gondii*)

In certain examples, the mutant *Toxoplasma* of the present disclosure can be used as a vehicle to deliver exogenous antigens from non-*Toxoplasma* disease agents (i.e., antigens not naturally expressed by the *Toxoplasma*). For example, CRISPR technology can be utilised to replace the TPS/TPP-like gene with an exogenous gene the encodes an antigen for which immunisation is desired.

Specific examples of exogenous antigens include tetanus toxoid (tetC), malarial antigens such as circumsporozoite protein (CSP) and merozoite surface protein-1 (MSP-1), *Bacillus anthracis* protective antigen, *Yersinia pestis* antigen, antigens from bacterial pathogens such as *Francisella tularensis*, Mycobacteria, *Legionella, Burkholderia, Brucella*, and *Coxiella*; antigens from viruses, particularly intracellular invaders such as HIV; other toxoids such as botulinum toxoid or Epsilon toxin; tumor antigens; multiagent biodefense antigens; antigens from non-biothreat infectious agents; plague antigens; and combinations of any of these.

In other examples, the mutant of *Toxoplasma* can be used to express any other genes one would want to express within a mammalian host cell. This could include genes encoding therapeutic peptides or proteins, e.g., therapeutic antibodies (e.g., Trastuzumab) proteins (e.g., interferons, blood factors, insulin, erythropoietin, and blood clotting factors), or enzymes (e.g., asparaginase, catalase, lipase, and tissue plasminogen activator) used in the treatment of diseases or conditions; as well as proteins, enzymes or peptides of use in screening assays to identify inhibitors or activators (i.e., effectors) of the same.

Additional non-*Toxoplasma* vaccine antigens that may be included are Leptospira antigens, clostridial antigens, rabies antigens, *Campylobacter* antigens and *Corynebacterim* antigens. The mutant *Toxoplasma* or vaccine containing the same can be employed in various methods inducing an immune response and protecting a subject against infection by *Toxoplasma* and/or a non-*Toxoplasma* disease. Such methods generally involve administering to an animal in need of treatment (e.g., an animal at risk of being exposed to an infectious disease or at risk of developing cancer) an effective amount of an attenuated mutant *Toxoplasma* or vaccine of the present invention thereby generating an immune response and protecting the animal against infection by *Toxoplasma* and/or the non-*Toxoplasma* disease.

An effective amount, as used in the context of the present disclosure, is an amount which produces a detectable immune response (e.g., a Th-1 response, natural granulocyte, neutrophil, macrophage, GR1+ macrophage, B cell, or T cell immune response) or antibody production. In accordance with some examples, the *Toxoplasma* mutant expresses an exogenous antigen thereby generating protective immunity against the pathogen or disease from which the antigen was derived or associated. However, in other examples, the *Toxoplasma* mutant of the disclosure alone is sufficient to generate an immune response to *Toxoplasma*. An effective amount of a *Toxoplasma* mutant of the disclosure prevents or treats the signs or symptoms of *Toxoplasma*. Responses to administration can be measured by monitoring T cell or antibody responses according to any suitable method known in the art.

In other example, the mutant *Toxoplasma* parasites described herein can be used to provide an industrial source of starch as an alternative to plant-derived sources of starch.

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Where reference is made to a URL or other such identifier or address, it is understood that such identifiers can change and particular information on the internet can come and go, but equivalent information can be found by searching the internet. Reference thereto evidences the availability and public dissemination of such information.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

EXAMPLES

Materials and Methods
Parasite Culture

*T. gondii* tachyzoites were maintained in human foreskin fibroblasts (HFFs) in D1 medium (Dulbecco's Modified Eagle medium [DMEM] supplemented with 1% foetal calf serum [Invitrogen] and 2 mM Glutamax [Gibco]) in a humidified atmosphere of 10% $CO_2$ at 37° C. For growth in glucose-free conditions, parasites were maintained in glucose-free DMEM supplemented with 4 mM glutamine and 6 mM Glutamax (Gibco). Before inoculation with parasites, HFFs were grown and maintained in D10 medium (DME supplemented with 10% cosmic calf serum [Thermo Scientific]).

DNA Cloning and Transfections

DNA amplification was performed using either PrimeSTAR HS or PrimeSTAR MAX DNA polymerase (Takara) according to the manufacturer's instructions. Restriction enzymes were from New England Biolabs (NEB). Oligonucleotide primers are provided in Table 1 below.

TABLE 1

Oligonucleotide primers

| Oligo # | Oligo sequence (5' → 3') | Description |
|---|---|---|
| 1 | gggaattggcGTTTTAGAGCTAGAAAT AGCAAG (SEQ ID NO:10) | TPS/TPP protospacer-Forward |
| 2 | cagagacgggcAACTTGACATCCCCAT TTAC (SEQ ID NO:11) | TPS/TPP protospacer-Reverse |
| 3 | ATGCTGTACACCAGGGTTTTCTTCC (SEQ ID NO:12) | Atps/tpp Screening-Forward |
| 4 | GATGCAGACTCTACGAGACAGGCAC (SEQ ID NO:13) | Atps/tpp Screening-Reverse |
| 5 | CTCAGATCTACTTTCCCGAGAGGAAGA GTG (SEQ ID NO:14) | HxK HA Ct-tagging-Forward |
| 6 | ttcctaggtcctgctccagcagcgtag tccgggacatcgtacgggtatcctgca ccagcGTTCACATCTGCGATCAGAGC (SEQ ID NO:15) | HxK HA Ct-tagging-Reverse |
| 7 | GGTCTTCCCCGTCTCTGGGGAATTGAC TAGCTGAGCAGGTGAGGCTGCGTCGCC GTCGC (SEQ ID NO:16) | Atps/tpp CRISPR stop-Forward |
| 8 | GCGACGGCGACGCAGCCTCACCTGCTC AGCTAGTCAATTCCCCAGAGACGGGGA AGACC (SEQ ID NO:17) | Atps/tpp CRISPR stop-Reverse |

Q5 mutagenesis (NEB) was performed according to the manufacturer's instructions. Some plasmids were constructed in-house and details of these plasmids are available upon request.

For electroporation using the 4D Nucleofector system (Lonza), $2 \times 10^6$ parasites were suspended in 20 µl of supplemented P3 solution containing variable amounts of DNA dependent on the experiment. Transfection was carried out in 20 µl Nucleocuvette strips (Lonza) using the F1-115 program (T cell, human unstimulated, HE).

Following electroporation, parasites were immediately transferred to HFFs in complete or glucose-free medium. For drug selection, recombinant parasites were selected by addition of chloramphenicol (20 µM), or mycophenolic acid (20 µg/mL) and xanthine (50 µg/mL), or with 5'-fluo-2'-deoxyuridine (FUDR) at 5 µM (for negative selection in the absence of uracil phosphoribosyl transferase [UPRT]).

Disruption of the genomic sequence of the trehalose synthase/phosphatase (TPS/TPP) gene (ToxoDB Gene ID TGGT1_297720; FIG. 1) was carried out using CRISPR/Cas9 technology (Shen Z et al., (2014) Dev Cell September 8; 30(5):625-36; Sidik S. M. et al PLoS One 2014 Jun. 27; 9(6):e100450 PMID:24971596). Q5 mutagenesis was used to replace the UPRT proto-spacer of plasmid pSAG1-Cas9-U6-sgUPRT (Shen et al., 2014) with the target TPS/TPP gene proto-spacer (CCCGTCTCTGGGGAATTGGC), using primers 1 and 2 in Table 1. Primer 2 also adds a 'G' to the 5' end of the protospacer to better initiate transcription. This construct (10 µg) was transfected into RH: Δhxgrpt parasites (Donald R G and Roos D S (1998) Mol Biochem Parisitol 15; 91(2):295-305). After 48 hours in culture, the parasites were FACS sorted (based on high GFP expression) into the wells of 96-well microplates (Corning) at 3 parasites/well. Two parasite clones that produced visible starch granules were sequenced using screening oligonucleotides 3 and 4 in Table 1. One clone housed a single point mutation (FIG. 3B; RH:Δhxgprt:Δtps/tpp cl-1), while the other contained a 183-base pair insertion originating from the transfection plasmid, both resulting in frame-shift mutations (FIG. 3C; designated RH:Δhxgprt:Δtps/tpp cl-2).

This mutant comprises the sequence shown below:

(SEQ ID NO: 18)
<u>CCCGTCTCTGGGGAA</u>AGCCGGCGAACGTGGCGAGAAAGGAAGGGAAGAAA

GCGAAAGGAGCGGGCGCTAGGGCGCTGGCAAGTGTAGCGGTCACGCTGCC

CGTAACCACCACACCCGCCGCGCTTAATGCCGCCGCTACAGGGCGCGTCCC

ATTCGCCTCGGGGGAGCCCTTCAGCTTCTCATAGTGGCTGGCCAGGTAGG

CAGGTGAGGCTGCGTCGCCG.

The proto-spacer is indicated by underline and the PAM motif is in bold text. The insert sequence is highlighted.

To counter the fact that the Δtps/tpp phenotype can revert back to wild-type phenotype over time in culture, Δtps/tpp parasites were also generated in glucose-free medium. By omitting glucose as a carbon source, the severe amylopectin phenotype is absent, but can be induced by subsequent addition of glucose to the medium. To do this, RH: Δhxgprt parasites that had been maintained in glucose-free DMEM supplemented with 4 mM glutamine and 6 mM Glutamax (Gibco), were transfected with 20 µg pSAG1-Cas9-U6-sgTPS/TPP. Parasites were cloned out by limiting dilution in glucose-free medium supplemented with Glutamax/glutamine. After 7 days, a clone of RH: Δhxgprt: Δtps/tpp) that produced starch granules when transferred to glucose-containing D1 medium was sequenced and found to contain a single base pair deletion resulting in gene disruption (FIG. 3; designated RH:Δhxgprt: Δtps/tpp cl-23).

For disruption of TPS/TPP in type II Pru:tdTomato parasites, 20 μg of pSAG1-Cas9-U6-sgTPS/TPP was transfected into parasites and cloned out immediately in 96-well plates at 5 parasites/well containing HFFs in D1 medium lacking glucose, but containing 6 mM glutamax and 4 mM glutamine. After 14 days, a single clonal line with visible starch accumulation was expanded further and sequenced, indicating the presence of a large >1 kb insert disrupting the TPS/TPP locus (FIG. 3E; Pru:tdTomato: Δtps/tpp cl-2).

This mutant comprises the sequence shown below:

(SEQ ID NO: 19)
GTCGGGTCTTCCCCGTCTCTGGGGAATTTGACGCGCCTCCTGCAGAACGC

GAGACACTGGGATATGTAGAGCCAAGGGGGAAACCTTCGAACTCTCGAAT

GTCTTCTCTGACAAGAATCATATTTCCATCAGTTCTGTCAGATTTTCAAA

TGGCGACCTGCAGAGGCCTGCTTCCTCCCTGTGCGCTCTTCGAAGGGGCT

TTCTGTCGCGCAGGGTAACTGAGTTGTTCCGTTGTGGCTTGCAGGTGTCA

CATCCACAAAAACCGGCCGACTCTAAATAGGAGTGTTTCGCAGCAAGCAG

CGAAAGTTTATGACTGGGTCCGAATCTCTGAACGGATGTGTGGCGGACCT

GGCTGATGTTGATCGCCGTCGACACACGCGCCAGTCGCAACGACCAGTCT

TTGAAGCTGCACGCACATGAAATCACGGACCGTGGAAAAGGCAACGGATG

TAAAACTTATTCCAATACCGTCNACCTCNAGGNGGNNCCCGGNNCCCNNT

TCGCCCNNTNGNGNGTCGTATTGCNNTTCNCTGGCCGTCGTTTTNCNNCG

TCGTGCCTGGGANNNCCCTGGCGTTNCCNNCTTGGTCGCCTTGCNGCGC

GTCCCCCTTTCGCCGGCTGGCGTNTNNNCTNAANGGCCCGCTCCNNNCGC

CCTTCCCNGCTCTTGCGCTTCCTGTNNGGCCTGCTGNCACGTCTCCCTGT

NTGCGGCGCTGTTCGTCGCGGCCGCNTCGTGGTTGTGTNNNGCCTCCCCC

GGTGTCCCGGCTCCCTTTTGCCCTTNGCCCTTGTGCGCCCCGCGTCCCTT

NNNGCCTTTCCTTTTCCTTTTNNNTTTTCCCCGCCCTGNNNTCTTGCTTT

GCCTTTTGCCTCTGGCCTCCCGTTCCTGGCTTTTNTNTCCCCGCGCGCNN

CTTTCCGCTGTTCCCGNNCNTNCTCCNCTGCCTTTTTCCCTGGCCGCCC

GNCGCGCCNTCCGCTGCGCCCCGGTTTTCGCTCTCNTGGGTCTCGCCTGG

GGTTNGCNTGACGGTATCGATAAGCTTTTAGGCAGGTGAGGCTGC.

The proto-spacer is indicated by underline and the PAM motif is in bold text. The insert sequence is highlighted. N indicates that the nucleotide base could not be determined from the sequence read.

Generation of ΔTps/Tpp Mutant with HA-Tagged Hexokinase

To generate Δtps/tpp parasites with hexokinase dual HA-tagged at its C-terminus, the 3' region of the *Toxoplasma* hexokinase (HxK) gene (Toxo DB gene #TGGT1_265450; FIG. 4) was amplified using oligonucleotides 5 and 6 having the sequence 5'-CTCAGATCTACTTTCCCGAGAGGA AGAGTG-3' (SEQ ID NO:14) and 5'-ttcctaggtcctgctcc agcagcgtagtccgggacatcgtacgggtatcctgcaccagcGTTCACA-TCTGCGATCAGAGC-3' (SEQ ID NO:15) respectively and inserted into pgCM3 (a kind gift from Giel van Dooren) via Bgl II and Avr II restriction sites. pgCH-HxK (20 μg) was linearized with Kas I before precipitating the DNA and transfecting into RH: Δhxgprt: ΔKu80 parasites. After 48 hours of culture, the transfected parasites were selected with 20 μM chloramphenicol. DNA sequencing of HA-tagged hexokinase revealed the following modified C-terminus: ADVNAGAGYPYDVPDYAAGAGPRAGAGYPYDVP-DYAAGAGPGDVIEL (SEQ ID NO:20) (where underlining highlights the original WT hexokinase C-terminus and shading highlights the two HA tags).

To disrupt TPS/TPP in the RH: Δhxgprt: Δku80:HxK-HA background, 10 μg of pSAG1-Cas9-U6-sgTPS/TPP was combined with 100 μg of annealed oligonucleotides 7 and 8 having the sequence 5'-GGTCTTCCCCGTCTCTGGG-GAATTGACTAGCTGAGCAGGTGAGGCTGCGTCGC-CGTCGC-3' (SEQ ID NO:16) and 5'-GCGACG GCGACGCAGCCTCACCTGCTCAGCTAGTCAAT-TCCCCAGAGACGGGGAAGACC-3' (SEQ ID NO:17) in Table 1 (Designed to insert a stop codon in the TPS/TPP reading frame) and electroporated into RH: Δhxgprt: Δku80: HxK-HA parasites.

In order to obtain viable parasites, the transfection and cloning procedures had to be carried out in glucose-free D1 medium supplemented with glutamine/Glutamax. Transfected parasites were cloned at 3 parasites/well in 96-well plates and a clone that produced starch granules when transferred to glucose-containing D1 medium was sequenced and found to contain a deletion of 58 bp resulting in TPS/TPP gene disruption (FIG. 3; RH: Δhxgprt: Δtps/tpp:HxK-HA cl-1). The sequence that was deleted is shown below:

(SEQ ID NO:21)
GTCGCCGTCGTCGGGTCTTCCCCGTCTCTGGGGAATTGGCAGgtgaggc
tgcgtcgcc

To generate Δcdpk2 parasites in the RH:Δhxgprt:Δku80:HxK-HA background, 20 μg of the CDPK2 gene knockout construct used previously (Uboldi A et al. (2015) Host Cell and Microbe 18:670-681), was digested with Nhe I/Cla I for transfection. Parasites were cloned by limiting dilution.

Plaque Assay to Determine Growth of ΔTps/Tpp Parasites in Glucose-Free and Glutamine-Free Conditions Parasites were scraped and passed through a 27-gauge needle to release intracellular parasites. Low speed centrifugation (450 rpm for 3 min in a Beckman GS-6KR centrifuge) was used to pellet debris and intact cells. This was followed by centrifugation at 2000 rpm for 5 min to pellet parasites. The parasites were resuspended in 10 ml of DMEM medium lacking both glucose and glutamine and centrifuged as before to pellet the parasites. The parasites were counted and added at 200 parasites/well to the wells of 6-well plates housing confluent HFF monolayers in medium containing both 5.55 mM glucose and 4 mM glutamine, or lacking either glucose or glutamine. The plaque assays were developed after 7 days by removing the medium, fixing with 80% ethanol for 20 min and staining the monolayer with crystal violet stain (2% crystal violet (w/v) and 0.16% ammonium oxalate in 20% ethanol) for 20 min. The monolayer was then washed with water to reveal plaques.

Periodic Acid-Schiff (PAS) Staining

Parasites were added to wells housing confluent HFF monolayers in medium containing both 5.55 mM glucose and 4 mM glutamine, or lacking either glucose or glutamine. The infected monolayers were incubated for 4 days at 37° C. and 10% $CO_2$ before processing for PAS staining as follows: The medium was removed and the infected monolayers were washed once with PBS, followed by fixation with PBS/4% formaldehyde (Sigma) for 20 min. The formaldehyde fixative was removed and the fixed monolayer was washed twice with PBS before placing the coverslips in 80% ethanol and performing PAS staining using standard protocols. PAS-stained coverslips were mounted onto slides and PAS fluorescence was measured with the A594 channel on a AP Deltavision Elite microscope (GE Healthcare) equipped with a Coolsnap2 CCD detector and captured with SoftwoRx software (GE Healthcare). PAS stained colour images were captured using a Nikon 90i Upright/Widefield microscope (Nikon).

Immunofluorescence Assays

HFFs grown on coverslips were infected with parasites and fixed with 4% paraformaldehyde (PFA) in PBS (Sigma-Aldrich) for 25 min. Fixed samples were permeabilized with 0.1% Triton X-100 in PBS for 10 min (BioRad), blocked for 1 hour with 3% (w/v) BSA (Sigma-Aldrich) in PBS and probed with primary antibodies overnight at 4° C., followed by Alexa Fluor-conjugated fluorescent secondary antibodies (Invitrogen) for 1 hour at room temperature. When DAPI staining of nuclei was required, 0.2 µg/ml (final concentration) DAPI was used. Images were taken with an AP DeltaVision Elite microscope (GE Healthcare) equipped with a CoolSnap2 CCD detector and captured with Soft-WoRx software (GE Healthcare). Images were viewed using Image J software and assembled using Image J, Adobe Photoshop and Illustrator software.

Antibodies for the immunofluoresence assays were rat-anti-HA (clone 3F10; Roche), rabbit anti-GAP45 (a kind gift from Con Beckers, Univ. North Carolina) and mouse anti-SAG1 (DG52) (a kind gift from John Boothroyd, Stanford University).

In Vivo Infection of Mice with Pru:tdTomato:ΔTps/Tpp Parasites

Pru:tdTomato (WT) and Pru:tdTomato:Δtps/tpp parasites were scraped and passed through a 27-gauge needle to release intracellular parasites. A low speed centrifugation (450 rpm for 3 min) was used to pellet debris and intact cells. This was followed by centrifugation at 2000 rpm for 5 min to pellet parasites. The parasites were resuspended in 10 ml PBS and washed by centrifugation as above. The parasite pellets were the resuspended in PBS at a concentration of 10 000 parasites/100 µL. C57BL/6 mice were inoculated with 10 000 parasites and their weights and survival were monitored over several weeks.

Hexokinase Activity Assays

Freshly egressed RH:WT and RH:Hxk-HA parasites from T25 cultures were spun at low speed (350 rpm for 5 min in a Beckman GS-6KR centrifuge) to pellet cellular debris. The supernatants were centrifuged at 2000 rpm for 5 min to pellet the parasites. Parasite pellets were either used immediately for Hexokinase activity assays or stored at −80° C. for use at a later stage. Hexokinase assays were performed according to the manufacturer's instructions (Abcam), with slight modifications, as follows: The parasites were washed twice with ice-cold PBS before resuspending in 200-400 µl of ice-cold assay buffer and pipetting up-and-down 5-10 times to lyse the cells. The lysates were centrifuged for 5 min at 4° C., at 13 0000 rpm to pellet insoluble material. The supernatants were collected and used for hexokinase assays. For each reaction, 50 µl of lysate was combined with an equal volume of reaction mix prepared according to the kit instructions. The absorbance at 450 nm was then measured over time and hexokinase activity was determined by comparison to a standard curve of NADH absorbance and normalised to the protein concentration in the lysates determined by the BCA method (Pierce).

Complementation Assays

For complementation of Δtps/tpp parasites with either wild type TPS/TPP or modified heterologous proteins, the WT TgTPS/TPP and mutant cDNAs were ligated to the vector pHTU-3xHA (created in-house). This vector places the complementing wild type TgTPS/TPP and mutant variants under control of 2760 bp of the tubulin upstream region and introduces a triple-HA tag at the C-terminal end of the protein. The plasmid allows for selection with mycophenolic acid and contains a genomic DNA region from the UPRT locus to allow for stable integration of the constructs into this locus following selection with 5'-fluo-2'-deoxyuridine. To create a construct for complementation of Δtps/tpp parasites with full-length TgTPS/TPP, gBlock 1 (Table 2) was amplified with oligonucleotides 9 and 10, and gBlock 2 was amplified with oligonucleotides 11 and 12 (see Table 3).

TABLE 2 gBlock sequences

| gBlock No. | DNA sequence |
| --- | --- |
| 1<br>TgTPS/TPP | catatagatctATGCTGTACACCAGGGTTTTCTTCCGTGCAGTGGTTCGGACAG<br>ACTTCGGTGAACGAGTCGCCGTCGTCGGGTCTTCCCCGTCTCTGGGGAAT<br>TGGCAGGCTGAACACGGCCATGAGCTGACCACAAACGAGGATGTCTTCCC<br>TTCGTGGTTCTCCAAGGAGCCTGTCTACTTGCCGCTAAAGAAACCCATATC<br>TTACAAATATGTTGTTCTCGACGAACGCGGCGACATCGTGAGGTGGGAAG<br>AATGCGAGGGAAATCGCGAGTTGGTGCCCACGGGCTTGGAGATGACGGT<br>GGAGGATGACGATGGCCTTTTTAGGGAGCAGATGACGAATCGCGGCGAC<br>CACGGAGTCGAAGGCGATGACGACGTGTCTGTGGCGGCTCTGGACAAGG<br>AGGAGGTGGACGCGCGCAACCGGATGCTGGCGATTCAAGAAGAAGAGCC<br>TGAGTTCGACGAGAACGACAGCGTAATTGTGTGTGCTCTTGACTTGCCTCT<br>GCGCGTGGTGCGTGTCTCGCCGTCTCGTGAGGCTTCTCCGCTGCCCTCC<br>TCgCTGCCtGCGTCGTCGACCGACTCTTCCGGCCAAACAGAAAAGCGAGC<br>GGTTTCATTCCCGGAAGACGCGGGaGCGAGTGCaCGGCGCTCGAGTTCG |

TABLE 2-continued gBlock sequences

| gBlock No. | DNA sequence |
|---|---|
| | ACCGTCGCGGCaACTCGGGAGGAGGAAACGACTCGCACTGCGAGTTCCT<br>TTCCtAAAGTCGAGGAGACGGCGGAaAGAGGACGaGACAGCTCgCTCGCT<br>CTTTGGCCTGGCGCAGCaCGCGACGCTGCCGGCGACTTCGGGGAGGCG<br>CTTCAGCCGagaGCGACcCGCAGCCGACGAGGCACCTTTGAAGTGAGGCC<br>GAGCAAGAGCGCGTTGcttCCTTCGCTGTTTCACCTGcgcAAGAAGACGCGG<br>CTGCCTGTGCGTTTCGTCGGGTGGCCGGGaATCCACGTCGAGAACGAAG<br>AGGAGCAGGCGGAGATTGCGGAGCTGCTGCGAGCCTACGACTGTTCGCC<br>GATCTTCCCAGACAAAGACGAGTTCGACTGCCATCTCACCTTCTGCCATCA<br>GGTCCTGTGGCCGCTGTTTCACAACGTCGTCGTCCTTGACTCCAATACCC<br>AGGTCCCGTTCGACTCCGACCTCTGGGCCAAGTACCAGGCTGTGAACAAA<br>CTGTGGGCGGACGCGGTGCTCCGCCAGGCGCACGAAACCGACATGGTCT<br>GGGTCCACGACTACCACCTGCTCCTCGCGCCCATGCACATTACGCGGAAA<br>GTCCGACGCGCCAACGTCGGCTTCTTTCTTCACATCCCCTTCCCCTCTTCC<br>GAAATCTTCAGGTGTCTCCCTTGCCGAGAAGACATTTTGCGAGGGATGCT<br>GTGCGCGGACTTGATTGGGTTTCACCTCTTCGAGTACGCGCGCCACTTTC<br>TGGTCGCATGCAAGCGGCTGCTCGGCCTCGAGCACCATTTTTGTCGAGG<br>GGGCATTCTGAACATCGAGTACGGCGGCCGCAACGTCTCGGTCCGCATC<br>GGCCATGTCCACATTCAGTACGCCGACATTCGCTCGAAAATCGAGGCAAA<br>CCCGGTGGTTCTGCAGATGGCGCGAGACATCAGACAAAAACACGTCGGA<br>AAATTCATCTTCGTCTCCGTGGACCGCTGCGAGAAATTGGCCGGTCTCCT<br>CCTCAAAGTTCGCGCCTTCCAGGCGTTTCTCGTGACCTACTCTTATGCCAG<br>GGGAAATGTCGTCCTCATTCAGTACGCGTATCCTACCATCAAATACGCAGA<br>AGACACAGAAACCATGGCGACGGAACTCAAAGAGCTCGTGGA<br>(SEQ ID NO:24) |
| 2<br>TgTPS/TPP | CTCAAAGAGCTCGTGGAGAAAGTCAATGCCCAGTTCGCCTTGCCAGATCG<br>CCCAGATTTCCAACATATCGAACTCCACATCCAGCCGGTCGGCTGGGAGG<br>AGAAGTGGGCGTTGTTTACCGCGGGCGACTGCTTCCTTGACACATCGATC<br>CGAGATGGCCTGAATCTCAATCCGTTCGAATTTATCTGTTGCCACAAAGAC<br>AACGTCACCGGTGTGATTTTATCAGAGTTCACGGGGTGCAGCAGAGCCCT<br>CGCCTCGGCCATTCGCGTCAATCCTTGGAAGGTGGAGGCGGTGGCAGAT<br>GCGATGGACAGAATCATCAACATGCCTGTGGAGGAGCAGCGCGACCGGT<br>TCACCCGCGACCGCGACTACTTGAGTCACAACAGTACGCAGAAGTGGGCA<br>GACGAAAACATTCTGGATCTGCGACGAGCCCGGAAACCAGACGACTTCGT<br>CTACGTCTCTTGGGGTCTCGGCAACACCTTCCGCGTCCTAGGCATGGACT<br>CCAACTTCCGGTTTCTGGACACAAATCAAGTGGTGCGAGGCTACCGAACT<br>TCTCGACATCGCGTCTTCTTCTTCGACTGCGAAGGCACACTCGCGCCGGA<br>CAGACGCCGAATCACTTTTTGTACCTGGCGGCGAAAATCTTTTTGCGCAAG<br>GTCGCCCGCCTTCGCCGCAAGTCAAGGACTGTCTCCAGGCGCTTGTCGA<br>CGACCAAAGAAACACTGTTGTCATTCTCGGGACGCGACAGACACCTCC<br>TAGAGGAATGGTTCTCTTCCATCAGAGGCATTGGACTTTGTGCCGAACAC<br>GGTTTTTACTACCGGGTTCCGGGCATCACGGGGGACCAGTGGCACTGCAT<br>GTCTCGTCAAACAGACTTCACATGGAAGCAAGTGGCGATCGAGCTGATGC<br>TGCAGTATGTGAAGCGAACTCAGGGCTCATTCATCGAAAACAAAGGAAGT<br>GCTCTCGTCTTCCAGTACCGCGACGCAGATCCGGATTTCGGCAGCATGCA<br>AGCCAAGGATCTCTCGAACTACCTCGGGGAACTGCTCTTCGGCTATCCTG<br>TCTCGGTCATGAGCGGGAAAGGCTACGTGGAAGTGAAACTGCGAGGTGT<br>CAACAAAGGGCATGCAGTCGAGAAAGTTCTGCGGAAACTCAGCAACCTCC<br>ACGGAGACGTCGACTTCGTTCTCTGCGTCGGAGATGACAGAAGCGACGAA<br>GACATGTTCGCGGTCATCAACGCaATGACGGAAGACGGaGACCAGCTGTG<br>CCTGCCAGAGGGCAGCGGaGCCGGCaGCAGCGGCCTCTATCGCCACACg<br>CAGTCGAAGGATCGAATTCCTAGACGCAACTCTGTCagtTCGGATGAGAAtC<br>GAGCAGAAGCTGTCGTTGGAAACGTCGAaGGACTCATGAAGCGTGACGGc<br>TCGATGCAaCAcGCaGGaGCaCTgGGatctGGaTTGACgagtGCaTCgTCtAGCA<br>CcAGTCTtAGTGGaCACACcAAgAAgACcAGTCCgCACTTcTTCACcTGtACcG<br>TCGGgAAGAAaCCtTCgAACGCaCGGTATTACCTgAACGACACgGAaGATGT<br>CTCCGATCTgCTCGACTCgCTgCAGCAaTGCACTGAGAAaGACGGcAAGGA<br>GCAGTGGAGTTCGagcAAGGACGCGAGTTGCCTCTCGGCaCCAGTCGTGG<br>CaGCtGCaGCGGCtGCGGGaTCGCTCGCaGGcAACGCaGCGGTcCAGCTGc<br>gcAAAGGCGACtctGCAGCaTCGAACTTTGCGAGTCTGTGGAGATCGCCgCT<br>cGGATCtGGAGCtGGaCGCACcAGAGAGcGAACGCTCGCGCAGTGGGCtGG<br>aCAGGCACCGAGCGCCATCTTCAGTCGaCCtGTCGGaCaGTTGAgGTTCG<br>aGCCAACGCAGCTGGCAGCACAGATCGCCCAACAGACGAGgctagcatat<br>(SEQ ID NO:25) |
| 3<br>PfHAD1 | catatagatctATGCACGAGATCGTcGACAAgAACGGAAAGAAGGTCCAgAAAAA<br>CAACctcAATGACGAGATCAAgATCATTTTCACAGACCTTGATGGCACGCTTc<br>tGAATtcGGAGAATAAAGTTTCCGAACAGAACCTGGAGTCTCTTATCCGaGC<br>GCAAGAAAGGGGATCAAAGTGGTCATCGCgACGGGGCGATCTATCTTCA<br>GCGTcGAAAACGTGATTGGCGAACACGTGAAGAAAAACcgcATTtctCTGCTT<br>CCCGGCATCTAcATGAACGGcTGCGTgACGTTTGATGAAAAGGGATCTCGG<br>GTcATCGACAGAATTATGAATAACGATctcAAgATGGAGATTCACGAATTCtct<br>AAACAgATTAACATTTCgAAGTACGCgATCTGGTTCTGcctcGAGAAGACGTA<br>CTGcTTCGAAATCAATGACTGCATTCGcGAGTATATGGAGGTCGAGGCgctG<br>AACCCGGATGTGATTGAAGACAATATGCTcGAGGGGCTGACAGTCTATAAg<br>GTTCTCTTTTCGCTCCCGGAGAACATTCTGGAAAACACActtAAACTCTGTA |

TABLE 2-continued gBlock sequences

| gBlock No. | DNA sequence |
|---|---|
| | GGGAGAAGTTTTCGCACAGGATCAACGTcGCgAATACCTTCCAgTCCTAcG<br>TGGAGCTCTTCCACCAACATACCAATAAATTCGAAGGGGTgAAGGAAATCT<br>GTAAATACTACAACATTTCCCTTAACAACGCCTTGGCCATGGGCGATGGC<br>GAGAATGATATTGAAATGTTGTCGGGATTGACACATTCTGTTGGAGTTCAC<br>AATGCgAGCGAGAAgGTTAAGAACTCGGCggCCTATGTcGGGCCTTCTAAT<br>AATGAACATGCgATCtctCATGTTCTCAAAACCTTCTGCGACATTgctagcatat<br>(SEQ ID NO:26) |
| 4<br>SpTPP1 | catatagatctATGTCCGTTTATGGcAAGATCCCTAGCACTTCTTTTGAGCATGA<br>GAATACATTCGAGCTCTCTGGCGACCTCTTGGACCCGGAGGAACTGAAGT<br>CTCTTGGAGTCTCCGGaAGaATTATCTATGTCCTGCGCCACCTTCCgTTTAA<br>AAGctcgATTAATGAAGAGACGCGAGAATGGGATCTTTCCGGACGACGGGG<br>CGCTACTACTATGTACtcgTCCATGAACTGGTTGGCCAATAGCACGTATTGG<br>CAGACCACACTGGTCGGCTGGACCGGGGTTATTCCGACCGTTTCTGAGAA<br>GGAGGAGAATAAGGATGCGGTTACCAGATTGGACtcgCAAGACGTGAAGC<br>GCTTCGAAGAAACATATTCCCAATGGAACtctGGGGAAcgcAGcACAGAGTAT<br>GTGCCtGTGTGGCTGCCTGGGCCGGAAAAAGGcAGCGAAACCATCATTAA<br>CGAAACCAGATCCCAGCAGTCTCGCTGGCTCGCGTACGCAGAAAATGTTA<br>TCcgaCCCCTTATTCACTATAAGTATTGGCCGTCTAGCGAGGTGGACGAGA<br>ATGAGGAGCAATGGTGGCGGGATTACGTTAAGATGAATCACGCTTTCGCT<br>GATAAAATTTGTGAAATCTATAAGCCGGGAGACTTTATTATCGTTCAAGACT<br>ACAGCCTGTTCCTGGTTCCGCAGCTGATCAGAAATAAAATTGACGACGCA<br>GTTATTGGGTTCTATCATCATCACCCgTTTCCGTCCTCCGAAATCGCTCGA<br>TGCTTCCCCCGGCGCagaGCAATTCTGCGATCGGTTCTCGGAGCGGATTTT<br>ATCGGGTTTGAAGACTATTctTATGCAcgcCATTTTATTTCCTGCTGTTCCCGT<br>GTTCTGGACTTGGAGATCGGGCACGATTGGGTGAATCTGAATGGcAATAA<br>GGTGACTGTGAGaGCAATTACAGTGGGCATTGACGTTCCCCGCATTATCC<br>GTAGCAGCGGGAATGTTtcgGTCTCCGAGAAATTGGAAGAGCTTAATAAAC<br>GGTATGAGAACATGAAGGTGATCCTTGGCAGAGATCGGCTCGACGAGCTG<br>TATGGgGTCCCtCAGAAAACTTAGATCGTTTCAGCGCTTTTTGCGaACGTACC<br>CgGAGTGGCGAAAAAAGGTTGTGCTCATTCAGATCACGATCTCCTCTGCCT<br>TTAAGCATCCtAAGCTTCTCAGcAGCATCAAGAAGCTCGTGCAAGCAATCAA<br>CCAAGAGTTCGGGACGGACGACTACACTCCCGTTCACCATGTGGAAGAGC<br>AACTGGAACCGGCAGACTATTTCGCCCTTTTGACCAGaGCCGATGCTTTGT<br>TTATCAATTCGATCCGAGAGGGcGTCTCTAATCTTGCCCTTGAATACGTGG<br>TTTGCCAGCGAGATCGCTATGGTATGGTCTTGCTCTCGGAATTTACGGCC<br>ACAAGCGCCATGTTGCACGACGTTCCTCTGATCAATCCgTGGGATTATAAC<br>GAATGT<br>(SEQ ID NO:27) |
| 5<br>SpTPP1 | CCgTGGGATTATAACGAATGTGCTGAAATCATTTCTAATGCACTTTCCACCC<br>CtCTGGAACGcCGCAAGATGATTGAACGCGAGtcgTATAAGCAAGTCACTAC<br>ACACACGATGCAATCTTGGACCagcTCTCTGATCCGATCTCTCGCCAACAA<br>GCTTGCCGCTACTAAAACTGACCAAAGAATCCCtACTCTGACGCCgGAACA<br>CGCTCTGTCGGTCTACTCCAAGGCGTCTAAGCGAcTGTTTATGATGGACTA<br>TGATGGaACGTTGACCCCGATCGTCCGcGATCTAATGCTGCGGTCCCTtc<br>gAAGAAACTTCTGGATAATCTGGCAACACTTGCCGCCGACCCCAAAAATCA<br>GGTGTGGATTATCTCGGGCCGAGATCAACAGTTCCTGCGAAATTGGATGG<br>ACGATATCAAGGGACTCGGGTTGTCTGCTGAGCATGGCTCGTTCGTTCGA<br>AAGCCgCATTCCACAACGTGGATTAATCTTGCAGAGCTGCTGGATATGTCG<br>TGGAAGAAGGAGGTTCGACGAATCTTCCAGTATTATACAGACCGCACCCA<br>GGGGTCTAGCATCGAAGAGAAACGcTGTGCGATGACGTGGCATTACAGaA<br>AAGCTGACCCCGAAAACGGAGCATTCCAGGCACTTGAGTGTGAAGCCCTT<br>CTCGAGGAACTGGTCTGTAGCAAGTACGATGTCGAAATCATGCGaGGAAA<br>AGCGAATCTCGAAGTCAGACCCtctAGcATCAATAAAGGaGGCATTGTCAAG<br>CAAATCTTGTCCAGCTATCCTGAGGACAGCCTGCCCTCGTTCATTTTCTGC<br>GCAGGCGACGACcgcACGGACGAGGACATGTTTCGGTCCCTTCATAAAAAT<br>ACGCGGATTAATAAGGAAACATCCTTTGCTGTCACGATCGGCtcgGACAAG<br>AAGCTGTCCATCGCAGACTGGTGCATCGCCGATCCCGCAAATGTTATTGA<br>TATCCTGGCAGACCTGGCCAATTTCACCAACgctagcatat<br>(SEQ ID NO:28) |
| 6<br>SCTPS1 | tataagatctATGACTACGGAcAACGCTAAaGCGCAgCTGACCTCGTCTTCtGGa<br>GGcAACATTATaGTGGTGTCgAaCcgcCTTCCCGTGACAATCACTAAAAACA<br>GCAGcACGGGACAGTACGAGTAtGCgATGTCGTCCGGAGGcCTGGTCACG<br>GCGctcGAAGGGcTGAAGAAaACGTACACgTTCAAGTGGTTCGGATGGCCT<br>GGGCTTgAGATTCCgGACGATGAGAAGGAcCAGGTGcgcAAGGACCcTtCTGG<br>AgAAGTTTAATGCCGTcCCCATCTTtCTGAGCGATGAAATCGCAGACctcCAC<br>TACAACGGGTTCAGcAATTCTATTCTcTGGCCGctcTTCCATTACCATCCTGG<br>cGAGATCAATTTtGACGAGAATGCGTGGTTGGCATACAACGAGGCAAACCA<br>GACGTTCACCAACGAGATTGCTAAGACgATGAACCAcAACGAccttATCTGG<br>GTGCATGAcTACCAcctcATGctcGTTCCGGAgATGCTGcgcGTCAAGATTCAC<br>GAGAAGCAACTGCAgAACGTTAAGGTCGGcTGGTTCCTGCACACgCCgTTtC<br>CTTCGAGcGAgATTTACAGAATCcttCCgGTCcgcCAAGAGATTTTGAAGGGaG<br>TccctctcgTGTGATctcGTCGGGTTCCACACATAtGAcTATGCgAGACAcTTCTTG<br>TCTTCCGTcCAgcGAGTGCTTAACGTGAACACActcCCgAATGGGGTGGAAT |

TABLE 2-continued gBlock sequences

| gBlock No. | DNA sequence |
|---|---|
| | ACCAGGGCAGATTCGTTAACGTcGGGGCCTTtCCTATCGGcATCGACGTGG<br>ACAAGTTCACCGATGGGTTGAAAAAGGAATCCGTcCAAAAGAGAATCCAAC<br>AgcttAAGGAAACTTTCAAaGGCTGCAAGATCATAGTTGGaGTCGACcGGCT<br>GGAcTACATCAAAGGcGTGCCTCAGAAGTTGCACGCtATGGAgGTGTTTCT<br>GAAtGAGCATCCAGAATGGcgaGGCAAaGTTGTTCTGGTcCAGGTTGCAGTG<br>CCAtctCGcGGAGATGTGGAAGAGTACCAATATctccGATCTGTGGTCAATGA<br>GctcGTCGGacGAATCAACGGcCAGTTCGGcACTGTGGAATTtGTCCCCATCC<br>ATTTCATGCACAAGTCTATACCATTTGAAGAGCTGATTTCGCTcTATGCCGT<br>GAGCGAcGTCTGCcttGTCTCGTCCACTCGgGAcGGcATGAACTTGGTTTCCT<br>ACGAATATATTGCTTGCCAAGAAGAgAAGAAAGGcTCCctcATCCTGtctGAGT<br>TtACAGGTGCCGCACAgTCCTTGAATGGTGCgATTATTGTcAATCCTTGGAA<br>CACCCGAcGATCTTTCTGATGCgATCAACGAGGCCTTGACgTTGCCCGAcGTc<br>AAGAAAGAAGTTAACTGGGAAAAACTTTACAAATACATCTCTAAATACACTT<br>CTGCCTTCTGGGGTGAAAATTTCGTCCAcGAActcTACtctACATCgTCtAGCT<br>CgACAAGCTCCTCTGCgACCAAAAACgctagctata<br>(SEQ ID NO:29) |
| 7<br>TgTPS/TPP<br>rescue<br>mutant | catatagatctATGCTGTACACCAGGGTTTTCTTCCGTGCAGTGGTTCGGACAG<br>ACTTCGGTGAACGAGTCGCCGTCGTCGGGTCTTCCCCGTCTCTGGGGAAT<br>TGGCAGGCTGAACACGGCCATGAGCTGACCACAAACGAGGATGTCTTCCC<br>TTCGTGGTTCTCCAAGGAGCCTGTCTACTTGCCGCTAAAGAAACCCATATC<br>TTACAAATATGTTGTTCTCGACGAACGCGGCGACATCGTGAGGTGGGAAG<br>AATGCGAGGGAAATCGCGAGTTGGTGCCCACGGGCTTGGAGATGACGGT<br>GGAGGATGACGATGGCCTTTTTAGGGAGCAGATGACGAATCGCGGCGAC<br>CACGGAGTCGAAGGCGATGACGACGTGTCTGTGGCGGCTCTGGACAAGG<br>AGGAGGTGGACGCGCGCAACCGGATGCTGGCGATTCAAGAAGAAGAGCC<br>TGAGTTCGACGAGAACGACAGCGTAATTGTGgtcGCTaaccgcTTGCCTCTGC<br>GCGTGGTGCGTGTCTCGCCGTCTCGTGAGGCTTCTCCGCTGCCCTCCTCg<br>CTGCCtGCGTCGTCGACCGACTCTTCCGGCCAAACAGAAAAGCGaGCGGT<br>TTCATTCCCGGAAGACGCGGGaGCGAGTGCaCGGCGCTCGAGTTCGACC<br>GTCGCGGCaACTCGGGAGGAGGAAACGACTCGCACTGCGAGTTCCTTTC<br>CtAAAGTCGAGGAGACGGCGGAaAGAGGACGaGACAGCTCgTCGCTCTT<br>TGGCCTGGCGCAGCaCGCGACGCTGCCGGCGACTTCGGGGAGGCGCTT<br>CAGCCGagaGCGACcCGCAGCCGACGAGGCACCTTTGAAGTGAGGCCGA<br>GCAAGggcggaTTGcttCCTTCGCTGTTTCACCTGcgcAAGAAGACGCGGCTG<br>CCTGTGCGTtggGTCGGGTGGCCGGGaATCCACGTCGAGAACGAAGAGGA<br>GCAGGCGGAGATTGCGGAGCTGCTGCGAGCCTACGACTGTTCGCCGATC<br>TTCctcGACAAAGACGAGTTCGACTGCCATacaacggcTTCtcgaattctatcCTGTG<br>GCCGCTGTTTCACAACGTCGTCGTCCTTGACTCCAATACCCAGGTCCCGT<br>TCGACTCCGACCTCTGGGCCAAGTACCAGGCTGTGAACAAACTGTGGGC<br>GGACGCGGTGCTCCGCCAGGCGCACGAAACCGACATGGTCTGGGTCCAC<br>GACTACCACCTGCTCCTCGCGCCCATGCACctccgcCGGAAAGTCCGACGC<br>GCCAACGTCGGCTTCTTTCTTCACATCCCCTTCCCCTCTTCCGAAATCTTC<br>AGGTGTCTCCCTTGCCGAGAAGACATTTTGCGAGGGgtgCTGTGCGCGGA<br>CTTGATTGGGTTTCACCTCTTCGAGTACGCGCGCCACTTTCTGGTCGCAT<br>GCAAGCGGCTGCTCGGCCTCGAGCACCATTTTTGTCGAGGGGGCATTCT<br>GAACATCGAGTACGGCGGCCGCAACGTCTCGGTCCGCATCGGCcctatcggc<br>ATTgacTACGCCGACATTCGCTCGAAAATCGAGGCAAACCCGGTGGTTCTG<br>CAGATGGCGCGAGACATCAGACAAAAACACGTCGGAAAATTCATCTTCGT<br>CTCCGTGGACcgcctggacatgatcaagGGTCTCCTCCTCAAAGTTCGCGCCTTC<br>CAGGCGTTTCTCGTGACCTACTCTTATGCCAGGGGAAATGTCGTCCTCATT<br>CAGTACGCGTATCCT<br>(SEQ ID NO:30) |
| 8<br>TgTPS/TPP<br>rescue<br>mutant | CGTCCTCATTCAGTACGCGTATCCTACCcgcacggaCgtccctgagtaccagaagctca<br>aatctcaggtgcacGAGCTCGTGggcagaatcAATggaCAGTTCggcTTGgtcGATCGC<br>CCAGATTTCCAACATATCGAACTCCACATCCAGCCGGTCGGCTGGGAGGA<br>GctcTGGGCGTTGTTTACCGCGGGCGACgttatgCTTgtgACATCGATCCGAGA<br>TGGCatgAATCTCgtctcgtacGAATTTATCTGTTGCCACAAAGACAACGTCACC<br>GGTGTGATTTTATCAGAGTTCACGGGGTGCAGCAGAGCCCTCGCCTCGGC<br>CATTCGCGTCAATCCTTGGAAGGTGGAGGCGGTGGCAGATGCGATGGAC<br>AGAATCATCAACATGCCTGTGGAGGAGCAGCGCGACCGGTTCACCCGCG<br>ACCGCGACTACTTGAGTCACAACAGTACGCAGAAGTGGGCAGACGAAAAC<br>ATTCTGGATCTGCGACGAGCCCGGAAACCAGACGACTTCGTCTACGTCTC<br>TTGGGGTCTCGGCAACACCTTCCGCGTCCTAGGCATGGACTCCAACTTCC<br>GGTTTCTGGACACAAATCAAGTGGTGCGAGGCTACCGAACTTCTCGACAT<br>CGCGTCTTCTTCTTCGACTacgacGGCACACTCtctCCGatcGTAgaggacccggatA<br>ATCTTTTTGCGCAAGGTCGCCCGCCTTCGCCGCAAGTCAAGGACTGTCTC<br>CAGGCGCTTGTCGACGACCAAAGAAACACTGTTGTCATTCTCTCGGGACG<br>CGACAGACACCTCCTAGAGGAATGGTTCTCTTCCATCAGAGGCATTGGAC<br>TTTGTGCCGAACACGGTTTTTACTACCGGGTTCCGGGCATCACGGGGGAC<br>CAGTGGCACTGCATGTCTCGTCAAACAGACTTCACATGGAAGCAAGTGGC<br>GATCGAGCTGATGCTGCAGTATGTGAAGCGAACTCAGGGCTCATTCATCG<br>AAAACAAAGGAAGTGCTCTCGTCTTCCAGTACCGCGACGCAGATCCGGAT<br>TTCGGCAGCATGCAAGCCAAGGATCTCTCGAACTACCTCGGGGAACTGCT<br>CTTCGGCTATCCTGTCTCGGTCATGAGCGGGAAAGGCTACGTGGAAGTGA |

TABLE 2-continued gBlock sequences

| gBlock No. | DNA sequence |
|---|---|
| | AACTGCGAGGTGTCAACAAAGGGCATGCAGTCGAGAAAGTTCTGCGGAAA |
| | CTCAGCAACCTCCACGGAGACGTCGACTTCGTTCTCTGCGTCGGAGATGA |
| | CAGAacgGACGAAGACATGTTCGCGGTCATCAACGCCATGACGGAAGACG |
| | GGGACCAGCTGTGCCTGCCAGAGGGCAGCGGCGCCGGGAGCAGCGGCC |
| | TCTATCGCCACACACAGTCGAAGGATCGAATTCCTAGACGCAACTCTGTCT |
| | CTTCGGATGAGAACCGAGCAGAAGCTGTCGTTGGAAACGTGGAGGGACT |
| | CATGAAGCGTGACGGGTCGATGCAGCATGCGGGGCGCTCGGCAGCGG |
| | CTTGACCTCTGCGTCTTCCAGCACAAGTCTCAGTGGGCACACAAAGAAAA |
| | CGAGTCCTCACTTTTTCACATGCACAGTCGGCAAGAAGCCGTCCAACGCT |
| | CGGTATTACCTCAACGACACTGAGGATGTCTCCGATCTCCTCGACTCTCTG |
| | CAGCAGTGCACTGAGAAGGACGGGAAGGAGCAGTGGAGTTCGTCGAAGG |
| | ACGCGAGTTGCCTCTCGGCGCCAGTCGTGGCaGCtGCaGCtGCTGCGGGa |
| | TCGCTCGCGGGGAACGCGGCGGTGCAGCTGAGGAAAGGCGACAGCGCA |
| | GCTTCGAACTTTGCGAGTCTGTGGAGATCGCCTCTGGGATCAGGAGCAGG |
| | TCGCACGAGAGAACGAACGCTCGCGCAGTGGGCGGGGCAGGCACCGAG |
| | CGCCATCTTCAGTCGCCCCGTCGGTGCCGTTGAAGTTCGCGCCAACGCA |
| | GCTGGCAGCACAGATCGCCCAACAGACGAGgctagcatat |
| | (SEQ ID NO:31) |
| 9 TgCBM20 mutant | catatagatctATGCTGTACACCAGGGTTTTCTTCCGTGCAGTGGTTCGGACAG |
| | ACTTCGGTGAACGAGTCGCCGTCGTCGGGTCTTCCCCGTCTCTGGGGAAT |
| | ctcCAGGCTGAACACGGCCATGAGCTGACCACAAACGAGGATGTCGcgCCTT |
| | CGTGGTTCTCCAAGGAGCCTGTCTACTTGCCGCTAAAGAAACCCATATCTT |
| | ACAAATATGTTGTTCTCGACGAACGCGGCGACATCGTGAGGctGGAAGAAT |
| | GCGAGGGAAATCGCGAGTTGGTGCCCACGGGCTTGGAGATGACGGTGGA |
| | GGATGACGATGGCCTTTTTAGGGAGCAGATGACGAATCGCGGCGACCAC |
| | GGAGTCGAAGGCGATGACGACGTGTCTGTGGCGGCTCTGGACAAGGAGG |
| | AGGTGGACGCGCAACCGGATGCTGGCGATTCAAGAAGAAGAGCCTGA |
| | GTTCGACGAGAACGACAGCGTAATTGTGTGTGCTCTTGACTTGCCTCTGC |
| | GCGTGGTGCGTGTCTCGCCGTCTCGTGAGGCTTCTCCGCTGCCCTCCTCg |
| | CTGCCtGCGTCGTCGACCGACTCTTCCGGCCAAACAGAAAAGCGaGCGGT |
| | TTCATTCCCGGAAGACGCGGGaGCGAGTGCaCGGCGCTCGAGTTCGACC |
| | GTCGCGGCaACTCGGGAGGAGGAAACGACTCGCACTGCGAGTTCCTTTC |
| | CtAAAGTCGAGGAGACGGCGGAaAGAGGACGaGACAGCTCgCTCGCTCTT |
| | TGGCCTGGCGCAGCaCGCGACGCTGCCGGCGACTTCGGGGAGGCGCTT |
| | CAGCCGagaGCGACcCGCAGCCGACGAGGCACCTTTGAAGTGAGGCCGA |
| | GCAAGAGCGCGTTGcttCCTTCGCTGTTTCACCTGCgcAAGAAGACGCGGCT |
| | GCCTGTGCGTTTCGTCGGGTGGCCGGGaATCCACGTCGAGAACGAAGAG |
| | GAGCAGGCGGAGATTGCGGAGCTGCTGCGAGCCTACGACTGTTCGCCGA |
| | TCTTCCCAGACAAAGACGAGTTCGACTGCCATCTCACCTTCTGCCATCAG |
| | GTCCTGTGGCCGCTGTTTCACAACGTCGTCGTCCTTGACTCCAATACCCA |
| | GGTCCCGTTCGACTCCGACCTCTGGGCCAAGTACCAGGCTGTGAACAAAC |
| | TGTGGGCGGACGCGGTGCTCCGCCAGGCGCACGAAACCGACATGGTCTG |
| | GGTCCACGACTACCACCTGCTCCTCGCGCCCATGCACATTACGCGGAAAG |
| | TCCGACGCGCCAACGTCGGCTTCTTTCTTCACATCCCCTTCCCCTCTTCCG |
| | AAATCTTCAGGTGTCTCCCTTGCCGAGAAGACATTTTGCGAGGGATGCTG |
| | TGCGCGGACTTGATTGGGTTTCACCTCTTCGAGTACGCGCGCCACTTTCT |
| | GGTCGCATGCAAGCGGCTGCTCGGCCTCGAGCACCATTTTTGTCGAGGG |
| | GGCATTCTGAACATCGAGTACGGCGGCCGCAACGTCTCGGTCCGCATCG |
| | GCCATGTCCACATTCAGTACGCCGACATTCGCTCGAAAATCGAGGCAAAC |
| | CCGGTGGTTCTGCAGATGGCGCGAGACATCAGACAAAAACACGTCGGAAA |
| | ATTCATCTTCGTCTCCGTGGACCGCTGCGAGAAATTGGCCGGTCTCCTCC |
| | TCAAAGTTCGCGCCTTCCAGGCGTTTCTCGTGACCTACTCTTATGCCAGG |
| | GGAAATGTCGTCCTCATTCAGTACGCGTATCCTACCATCAAATACGCAGAA |
| | GACACAGAAACCATGGCGACGGAACTCAAAGAGCTCGTGGA |
| | (SEQ ID NO:32) |
| 10 TgWDK 3xMyc tagging | CTCTCAGGTGGGCAGTGGCGTCGGTTTCTTCTCTCTTCATTCTCTTGTCGC |
| | CTGCGAAGTCGCGCTGCGTGTCTGCAGCTCGCGTTTCTTGTCGAGGATAA |
| | ATACGCGGTGCCCCAAGACATCGAAGGAGTCGTCGTCGGtGCgGAgACtGT |
| | TGCCCTgGTcCAgACGCGtACGCAgGTCCCTAGGGAACAAAAGTTGATTTCT |
| | GAAGAAGATTTGAACGGTGAACAAAAGCTAATCTCCGAGGAAGACTTGAA |
| | CGGTGCTAGGGCCGAGGAGCAGAAGCTGATCTCCGAGGAGGACCTGTGA |
| | gcacacagcatcgtcttgacgcgtctcgacctcgctctcgcgactcacttct |
| | ccggagagacggaaaaacggtgcgagtcaagaactcaggagaccccgaatcc |
| | gcagcttctacacatcacggttcaggccggtca |
| | (SEQ ID NO:33) |

The amplified gBlocks were digested with Bgl II/Sac I (gBlock 1) or Sac I/Nhe I (gBlock2) and ligated to pHTU-3HA via these sites. To create a complementation construct containing the PtHAD1 protein, codon-optimized gBlock 3 was amplified using oligonucleotides 13 and 14, digested with Bgl II and Nhe I, and ligated to pHTU-3HA. Similarly, to create a construct for complementation with SpTPP1, codon optimized gBlocks 4 and 5 were amplified with oligonucleotides 15 and 16, and 17 and 18, respectively, digested with Bgl II/Psi I (gBlock 4) and Psi I/Nhe I (gBlock 5) and ligated to pHTU-3HA. To create a complementation construct containing only the TgTPS domain, but lacking the TgTPP domain, oligonucleotides 9 and 19 were used to amplify the TPS domain using the pHTU-TgTPS/TPP-3HA complementation construct as DNA template. The TgTPS domain was inserted into pHTU-3HA via Bgl II and Nhe I sites. Constructs that contained the TgTPS domain fused to either the PtHAD1 or SpTPP1 domains were also created. For the TgTPS-PfHAD1 construct, the PtHAD1 domain was amplified from gBlock 3 using oligonucleotides 14 and 20 and digested with Nhe I, while the TgTPS domain was amplified using oligonucleotide 21 and either oligonucleotide 22 or 23 (to create different linker sequences) and digested with Bgl II. SpTPP1 was amplified from pHTU-SpTPP1-3HA template DNA with oligonucleotides 18 and 24 and digested with Nhe I for fusion to the TgTPS domain, as above. To create a construct for complementation with ScTPS1, codon-optimized gBlock 6 was amplified with oligonucleotides 25 and 26, digested with Bgl II and Nhe I and ligated to pHTU-3HA via these sites. To create a construct for complementation with the TgCBM20 domain fused to the ScTPS1 domain, the TgCBM20 domain was amplified with oligonucleotide 27 and either oligonucleotide 28 or 29 (to create either a rigid or flexible linker between the domains) and digested with Bgl II. The ScTPS1 gBlock 6 was amplified using oligonucleotides 26 and 30, and digested with Nhe I. The two products were ligated to pHTU-3HA via these sites. To create a complementation construct of TgTPS/TPP that has missing substrate binding residues reintroduced (and therefore hypothetically capable of producing the reaction product T6P), gBlock 7 was amplified using the oligonucleotides 9 and 31 and gBlock 8 was amplified using the oligonucleotides 12 and 32. The gBlocks were digested with Bgl II/Mlu I (gBlock 7) and Mlu I/Nhe I (gBlock 8) and ligated to pHTU-3HA via Bgl II and Nhe I sites. To create a complementation construct that has lost the ability to bind to amylopectin, gBlock 9 (containing mutations in 3 important starch binding residues) was amplified using oligonucleotides 9 and 10, digested with Bgl II/Sac I and ligated to Sac I/Nhe I-digested gBlock 2 and Bgl II/Nhe I digested pHTU-3HA. To create a construct for complementation of RH:Δku80:Δhxgprt:Hxk-HA:Δtps/tpp parasites, Bgl II/Sac I-digested gBlock 1 and SacI/Nhe I-digested gBlock 2 were ligated to Bgl II/Avr II-digested pHTU-3MYC (created in-house).

To tag the C-terminus of TgTPS/TPP with a triple-Myc epitope tag, the 3' regions of the gene were amplified using oligonucleotides 33 and 34, and inserted into pgCM3 via Bgl II and Avr II restriction sites. The construct was linearized with Sfo I for transfection into RH:Δku80:DHFR, RH:Δku80:Δhxgprt:Hxk-HA and RH:Δku80:DHFR:Δcdpk2 parasites, and drug selected with chloramphenicol. To make a Myc-tagged construct that can be selected by mycophenolic acid/xanthine, the TPS/TPP fragment was cut from the pgCM3-TPS/TPP-3MYC construct above with Spe I and ligated to pHTU-3HA vector backbone digested with Spe I and Nhe I. The resulting pHTU-TgTPS/TPP-3xMyc construct was digested with Aar II and 10 μg was transfected into RH:Δku80:Δhxgprt:Hxk-HA parasites to produce a RH:Δku80:Δhxgprt:Hxk-HA:TPS/TPP-3Myc line.

TABLE 3

Oligonucleotides

| Oligo # | Oligo sequence (5' → 3') | Description |
|---|---|---|
| 9 | CATATAGATCTATGCTGTACACCAGGGTTTTCTTC (SEQ ID NO:34) | TgTPS/TPP gBlock1-Forward |
| 10 | TCCACGAGCTCTTTGAGTTCCGTC (SEQ ID NO:35) | TgTPS/TPP gBlock1-Reverse |
| 11 | CTCAAAGAGCTCGTGGAGAAAGTCAATGC (SEQ ID NO:36) | TgTPS/TPP gBlock2-Forward |
| 12 | ATATGCTAGCCTCGTCTGTTGGGCGATC (SEQ ID NO:37) | TgTPS/TPP gBlock2-Reverse |
| 13 | CATATAGATCTATGCACGAGATCGTCGACAAG (SEQ ID NO:38) | PfHAD1 gBlock-Forward |
| 14 | ATATGCTAGCAATGTCGCAGAAGGTTTTGAG (SEQ ID NO:39) | PfHAD1 gBlock-Reverse |
| 15 | CATATAGATCTATGTCCGTTTATGGCAAGATC (SEQ ID NO:40) | SpTPP1 gBlock1-Forward |
| 16 | ACATTCGTTATAATCCCACGGATTGATC (SEQ ID NO:41) | SpTPP1 gBlock1-Reverse |
| 17 | CCGTGGGATTATAACGAATGTGCTGAAATC (SEQ ID NO:42) | SpTPP1 gBlock2-Forward |
| 18 | ATATGCTAGCGTTGGTGAAATTGGCCAG (SEQ ID NO:43) | SpTPP1 gBlock2-Reverse |
| 19 | ATATGCTAGCGAGACAGTCCTTGACTTGC (SEQ ID NO:44) | TgTPS only-Reverse |
| 20 | CACGAGATCGTCGACAAGAACGGAAAG (SEQ ID NO:45) | PfHAD1 fusion-Forward |
| 21 | GCATATAGATCTATGCTGTACACCAGG (SEQ ID NO:46) | TgTPS linker-Forward |

TABLE 3-continued

Oligonucleotides

| Oligo # | Oligo sequence (5' → 3') | Description |
|---|---|---|
| 22 | AGGCGGGCGACCTTGC (SEQ ID NO:47) | TgTPS linker-R-short |
| 23 | CTTGACTTGCGGCGAAGG (SEQ ID NO:48) | TgTPS linker-R-long |
| 24 | TCCGTTTATGGCAAGATCCCTAGCACTTC (SEQ ID NO:49) | SpTPP1 fusion-Forward |
| 25 | TATAAGATCTATGACTACGGACAACGCTAAAGC (SEQ ID NO:50) | ScTPS1-gBlock-Forward |
| 26 | TATAGCTAGCGTTTTTGGTCGCAGAGG (SEQ ID NO:51) | ScTPS1-gBlock-Reverse |
| 27 | TATAAGATCTATGCTGTACACCAGGGTTTTCTTCCGTGC (SEQ ID NO:52) | TgCBM20-BgIII-Forward |
| 28 | CGGAGGCCTGCCCTGCTCCCTAAAAAG (SEQ ID NO:53) | TgCBM20-QGRPP-Reverse |
| 29 | TCCCGAGCCTCCGCGATTCGTCATC (SEQ ID NO:54) | TgCBM20-GGSG-Reverse |
| 30 | ACTACGGACAACGCTAAAGCGCAGCTGACC (SEQ ID NO:55) | ScTPS1 fusion-Forward |
| 31 | AGGATACGCGTACTGAATGAGGACGAC (SEQ ID NO:56) | TgTPS/TPP gBlock1-R-Mlul |
| 32 | CGTCCTCATTCAGTACGCGTATCCTACC (SEQ ID NO:57) | TgTPS/TPP gBlock2-F-Mlul |
| 33 | TGATAGATCTTGTGCAGAAGGTGCTCCAC (SEQ ID NO:58) | TgTPS/TPP 3xMyc Ct- tagging-F |
| 34 | TATACCTAGGCTCGTCTGTTGGGCGATC (SEQ ID NO:59) | TgTPS/TPP 3xMyc Ct- tagging-F |
| 35 | CTCTCAGGTGGGCAGTGGCGTC (SEQ ID NO:60) | TgWDK3x Myc-F |
| 36 | TGACCGGCCTGAACCGTGATG (SEQ ID NO:61) | TgWDK3x Myc-R |
| 37 | GAGTCGTCGTGTTTTAGAGCTAGAAATAGCAAG (SEQ ID NO:62) | TgWDK 3Myc protospacer-F |
| 38 | CTTCGATGTCAACTTGACATCCCCATTTAC (SEQ ID NO:63) | TgWDK 3Myc protospacer-F |

Cyst Assays

Pru:tdTomato:Wt and Pru:TdTomato: Δtps/tpp parasites that had been maintained in glucose-free D1 medium were added to monolayers of humanforeskin fibroblasts (HFF) on coverslips in 6-well plates (Corning) at an M.O.I. of 1 parasite per 5 host cells. The parasites were spun onto the HFFs by centrifugation at 1400 rpm for 3 min and incubated in a humidified atmosphere of 10% $CO_2$ for 4 hours at 37° C. to allow attachment and invasion to occur. The glucose-free D1 medium was removed and replaced with bradyzoite-inducing medium (RPMI-Hepes, pH 8.1; 5% FBS), which was changed every second day of differentiation. Modified IFAs combining antibody staining and PAS staining were performed as described in Sugi T et al., (2017) mBio 8, e01289-17.

ATPS/TPP Immunization

ΔTPS/TPP tachyzoites were prepared from tissue culture and resuspended at $1\times10^4$/200 ul of PBS. 6×Wildtype C57BL/6 were infected intraperiotoneally (i.p) with $1\times10^4$ tachyzoites and actively monitored over 3 weeks.

Challenge with Wildtype Parasites

Pru:tdTomato:Δhx strain (type II) Toxoplasma strain was harvested from tissue culture resuspended in PBS at $1\times10^4$/ 200 ul of PBS. Six naive and 6×Δtps/tpp immunized animals were then injected i.p with $1\times10^4$Pru:tdTomato:Δhx strain and monitored daily for body weight and signs of infection.

Example 1 Disruption of the Toxoplasma Aondii (Ta) TPS/TPP-Like Ciene Results in Massive Accumulation of Amylopectin within *Toxoplasma* Tachyzoites To investigate the function of the TPS/TPP-like protein, the inventors created a gene disruption in hypervirulent type I (RH) tachyzoites and less virulent cyst forming Prugniaud (type II) strain. Genetic ablation of TgTPS/TPP in RH and tdTomato expressing P-strain was confirmed by PCR and sequencing.

Following gene disruption, massive amylopectin granules, as detected by Periodic-acid-Schiff (PAS) staining, were visible within the residual body and within the tachyzoites themselves (FIGS. 5A and C).

The inventors then assessed growth capacity through the lytic cycle by performing plaque assays on confluent human foreskin fibroblasts. Strikingly, the growth of RH:Δtgtps/tpp tachyzoites in fibroblasts was severely attenuated when host cells were cultivated in standard high glucose medium (FIG. 5B). In contrast, growth of the mutant was partially restored when host cells were cultivated in glucose-free medium containing glutamine as alternative carbon source (FIG. 5B). Interestingly, addition of glutamine to glucose-containing medium did not rescue growth indicating that glucose per se, rather than excessive carbon sources are toxic in the absence of TPS/TPP-like gene.

Example 2 Disruption of TPS/TPP Leads to a Decrease in Virulence In Vivo

To investigate whether the TPS/TPP-like gene is required for acute infection in animal models, C57BL/6 mice were infected with the parental Pru:tdTomato and Pru:Δtps/tpp parasites (see mutant FIG. 3E) and followed their survival and changes in body weight over time. Mice infected with parental parasites lost ten percent of their weight after 10 days and had to be culled (FIG. 5D). In contrast, mice infected with Pru:Δtps/tpp parasites exhibited little body weight loss and subsequently regained weight to pre-infection levels (FIG. 5D). The mice infected with wild-type Pru parasites lost significant body weight over time, with loss peaking at 10 days-post infections (FIG. 5D). At around this time, the mice rapidly succumbed to the infection (FIG. 5E).

Microscopic examination of brain tissues indicated the absence of cysts in these mice. TgTPS/TPP is thus essential for growth of both acute phase tachyzoites and chronic bradyzoites in infected tissues. The results also suggest that both stages are normally exposed to high glucose concentrations in vivo.

Example 3 Loss of TgTPS/TPP is Associated with Defects in Central Carbon Metabolism

*T. gondii* tachyzoites catabolize glucose via a number of pathways, including glycolysis and the pentose phosphate pathway, and also channel excess glucose into synthesis of the major storage carbohydrate, amylopectin (Uboldi A. D et al., (2015) Cell Host Microbe 18,670-681). Wild type RH tachyzoites normally have very low levels of amylopectin, as shown by Schiffs Periodate staining of intracellular parasite stages, indicating that most of the glucose taken up these parasites is used for glycolysis. In contrast, RH:Δtgtps/tpp tachyzoites accumulate a large number of Periodate-Schiffs-positive granules (FIG. 6A) in both the cytoplasm and the residual body, a membranous network that is continuous with the anterior ends of developing tachyzoites and often contains extraneous metabolites. The hyperaccumulation of amylopectin granules occurred when infected fibrablasts were cultivated in medium containing glucose, but not in glucose minus medium containing glutamine as major carbon source (FIG. 6B). Biochemical analysis confirmed that RHΔtgtps/tpp tachyzoites accumulated 100-fold higher levels of amylopectin compared to wild type parasites (FIG. 7A). When intracellular RH tachyzoites were labeled with $^{13}$C-glucose, the glucose associated with amylopectin was efficiently labeled, indicating constitutive synthesis and turnover of this polysaccharide under glucose replete conditions (FIG. 7B). Measurement of $^{13}$C-glucose incorporation into amylopectin in RH:Δtgtps/tpp parasites indicated a 5-fold increase in glucose flux into amylopectin synthesis in the mutant line (FIG. 7B). TgTPS/TPP thus appears to regulate glucose uptake and/or down-stream fluxes into different pathways of carbohydrate metabolism.

Figure 8:
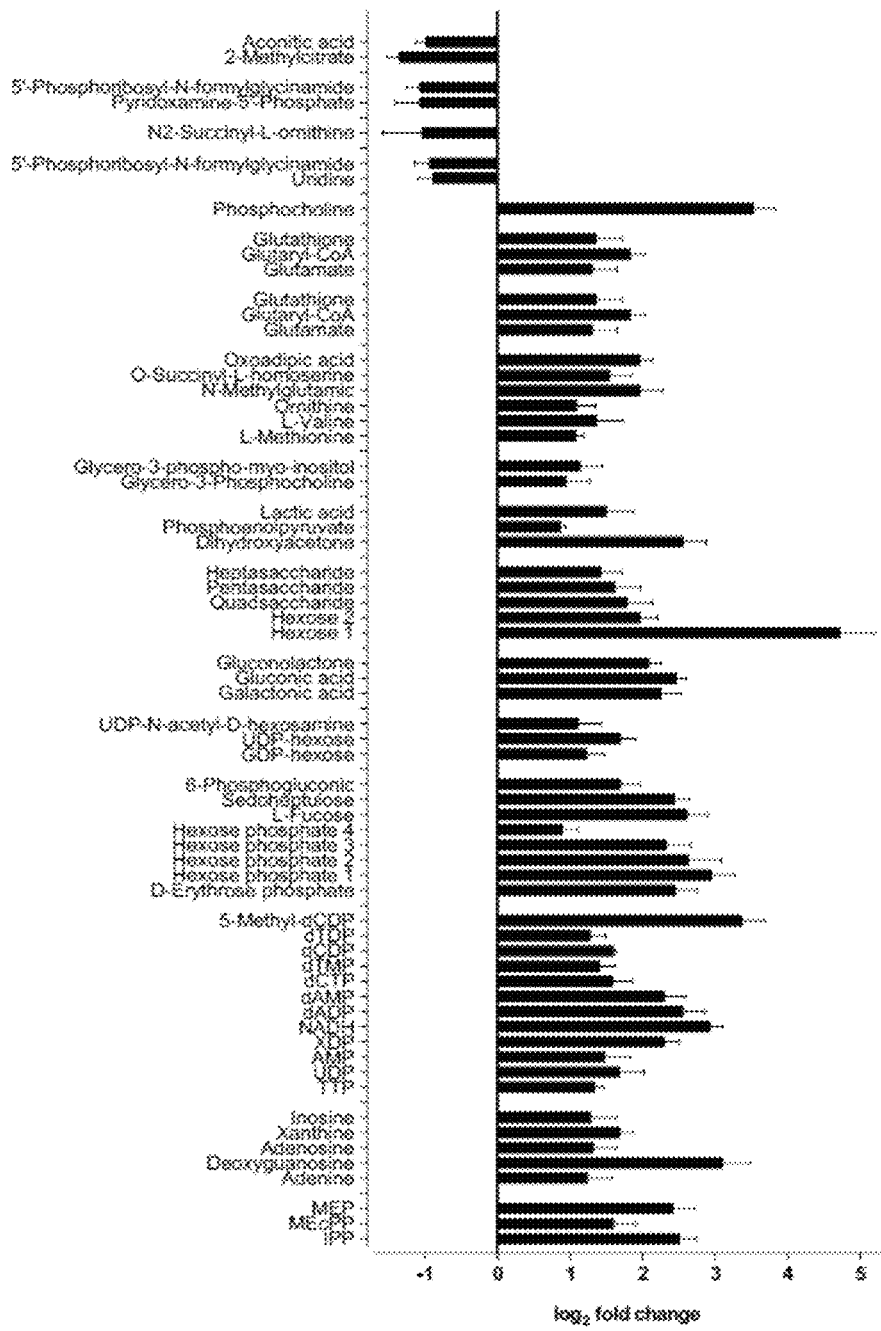
FIG. 8 shows polar metabolite levels in parental RH and RH:Δtgtps/tpp tachyzoites determined by LC/MS.

Metabolite profiling of RH parental and RH:Δtgtps/tpp tachyzoites indicated that loss of TgTPS/TPP was associated with global changes in parasite central carbon metabolism. In particular LC/MS analysis of polar metabolites (resulting in detection of 2,657 m/z features) revealed that the mutant had elevated levels of intermediates in upper glycolysis and the pentose phosphate pathway (FIG. 8). Intermediates in pathways that are fed by glycolysis including the deoxy-xylulosephosphate pathway (DOXP) were also elevated in the knock-out parasites (FIG. 8). In contrast, levels of most amino acids and intermediates in the TCA cycle were largely unaffected by loss of TgTPS/TPP (FIG. 8). Loss of TgTPS/TPP thus appears to result in global increase in utilization of glucose and flux into pathways connected with upper glycolysis.

The inventors next measured rates of glucose uptake in extracellular RH parental and RH:Δtgtps/tpp mutant tachyzoites to investigate whether TgTPS/TPP could be modulating the activity of the plasma membrane glucose transporter. Strikingly, TgTPS/TPP deficient tachyzoites parasites exhibited similar or slightly lower rates of $^{14}$C-glucose uptake compared to the parental line (FIG. 9A).

To determine whether down-stream steps in glucose catabolism were enhanced in the absence of TgTPS/TPP, parental RH and RH:Δtgtps/tpp tachyzoites were metabolically labeled with $^{13}$C-glucose and the kinetics of incorporation of $^{13}$C into hexose phosphates and other glycolytic intermediates determined by GC/MS. Strikingly, rates of synthesis of glucose-6-phosphate (FIG. 9B) and metabolically connected hexose-phosphates were highly elevated in the RH:Δtgtps/tpp mutant, suggesting that TgTPS/TPP may negatively regulate the phosphorylation of glucose.

LC-MS/MS proteomic analysis of parasite extracts indicated that expression of hexose kinase is not altered in TPS/TPP knockout parasites compared to WT parasites, nor are detectable post-translational modifications. Furthermore, complementary metabolic labeling of extracellular parasites with $^{13}$C-glutamine in glucose-rich medium revealed minimal labeling of hexose phosphates in both parental RH and RH:Δtgtps/tpp tachyzoites, indicating that the elevated levels of sugar phosphates in the mutant tachyzoites is not due to increased gluconeogenic flux.

Figure 10:
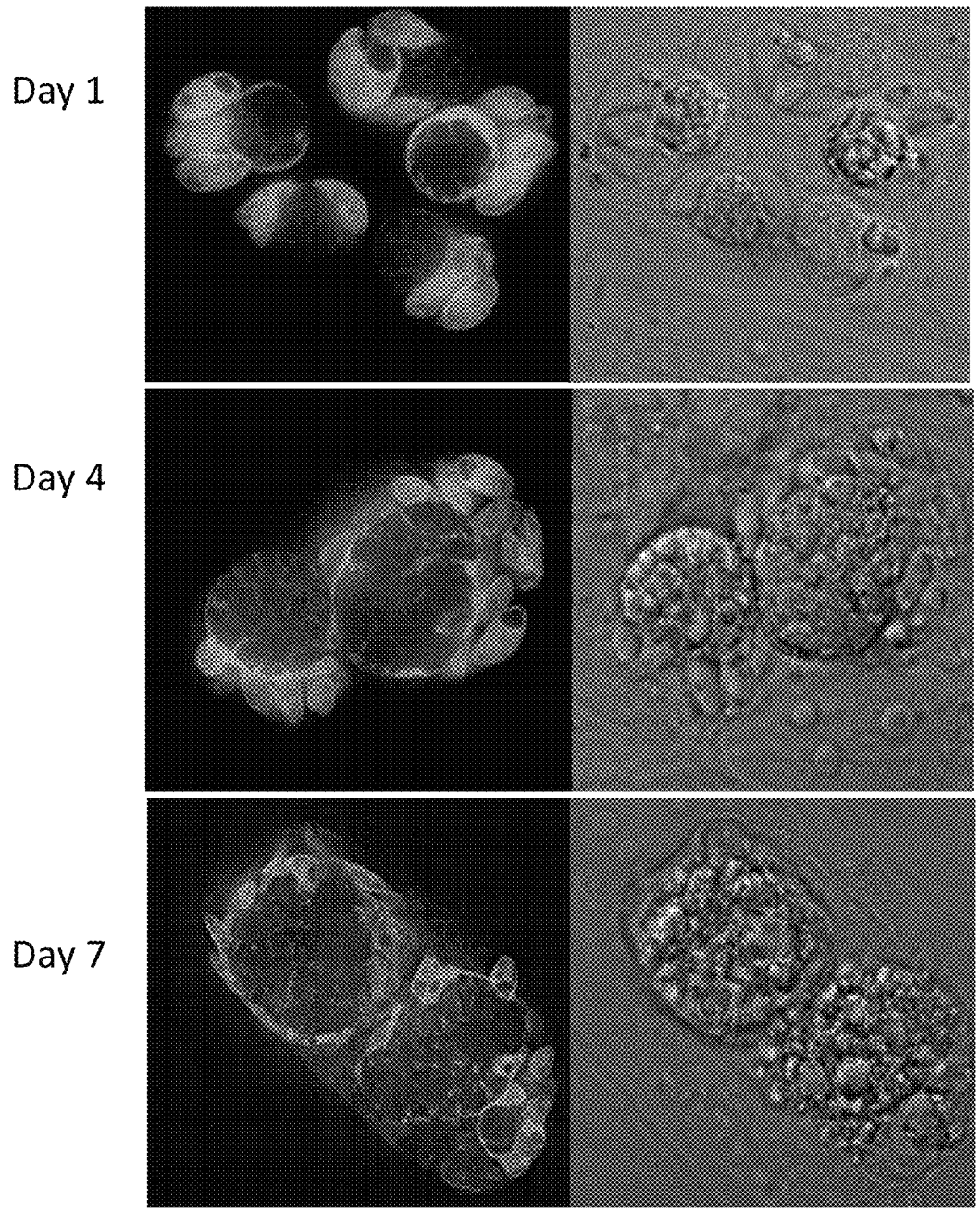
FIG. 10 shows massive accumulation of amylopectin granules in Δtps/tpp:HxK-HA parasites leading to lack of viable parasites. An HA-epitope tagged version of TgHxK was expressed in RD::Δtgtps/tpp parasites and infected fibroblasts cultivated in standard glucose-containing medium for 1 day, 4 days and 7 days. Immunofluorescence images were taken of infected host cells at different time points and stained with anti-HA (TgHxK) and Gap45 (inner membrane complex).

Example 4 Disruption of TgTPS/TPP in Combination with Disruption of Hexokinase Results in Greater Attenuation of Mutant Parasites To further assess whether increased expression of hexose kinase activity was directly responsible for the severe amylopectin phenotype and loss of viability of the RH:Δtgtps/tpp mutant, an HA-epitope tagged version of *T. gondii* hexose kinase (TgHexK) was overexpressed in the mutant. Overexpression of hexose kinase in the mutant was associated with a dramatic decrease in parasite proliferation, the formation of very large residual bodies which were full of amylopectin granules within a day of infection and further expansion of this residual body and general loss of parasite integrity by day 7 (FIG. 10).

Figure 11:
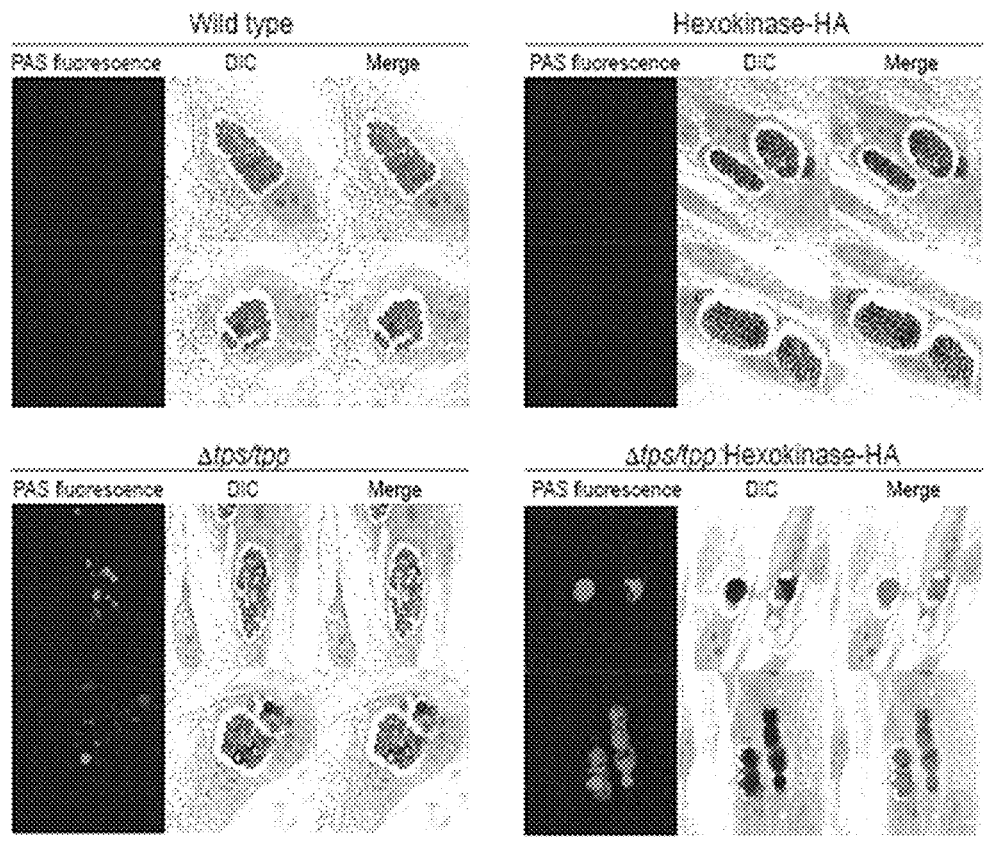
FIG. 11 PAS fluorescence showing that Δtps/tpp:HxK-HA parasites accumulate massive amounts of amylopectin over time when switched from glucose-free medium to glucose-containing medium and eventually die.

Accumulation of massive amylopectin granules continued unabated, creating morphological aberrations until the parasites died (FIG. 11). This defect was much more severe than that seen in Δtps/tpp parasites with untagged wild-type hexokinase (FIG. 11), suggesting that the new modified C-terminus (containing two HA-tags) was responsible for the increased severity of the Δtps/tpp phenotype.

Figure 12:
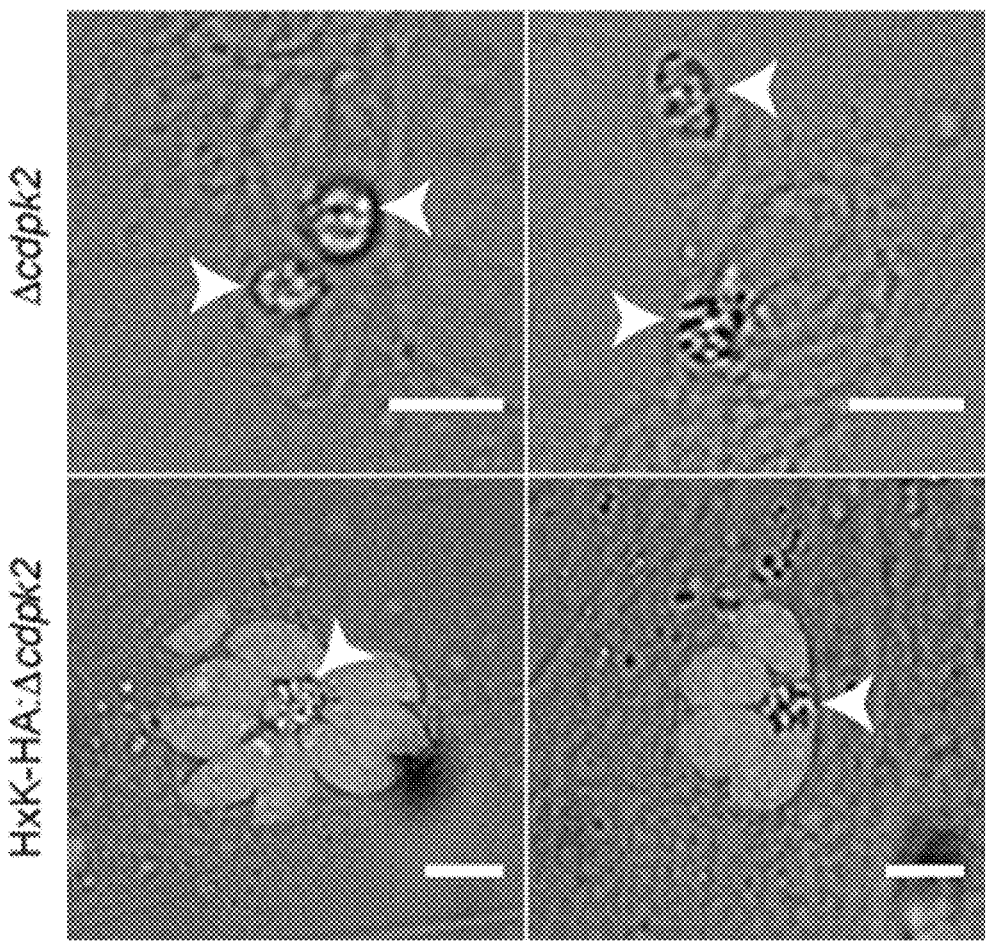
FIG. 12 shows Δcdpk2:Hxk-HA parasites have amylopectin levels equivalent to Δcdpk2 parasites and may be maintained in glucose-containing medium without loss of viability. White arrowheads indicate amylopectin granules and green staining indicates HxK-HA protein expression as detected by IFA probed with an anti-HA antibody and AlexaFluor-488 secondary antibody. Scale bar represents 5 μm.

Moreover, this severe phenotype was specific for Δtps/tpp:HxK-HA parasites, as by contrast, Δcdpk2:HxK-HA parasites showed only the level of starch accumulation typical for Δcdpk2 parasites (FIG. 12).

Figure 13:
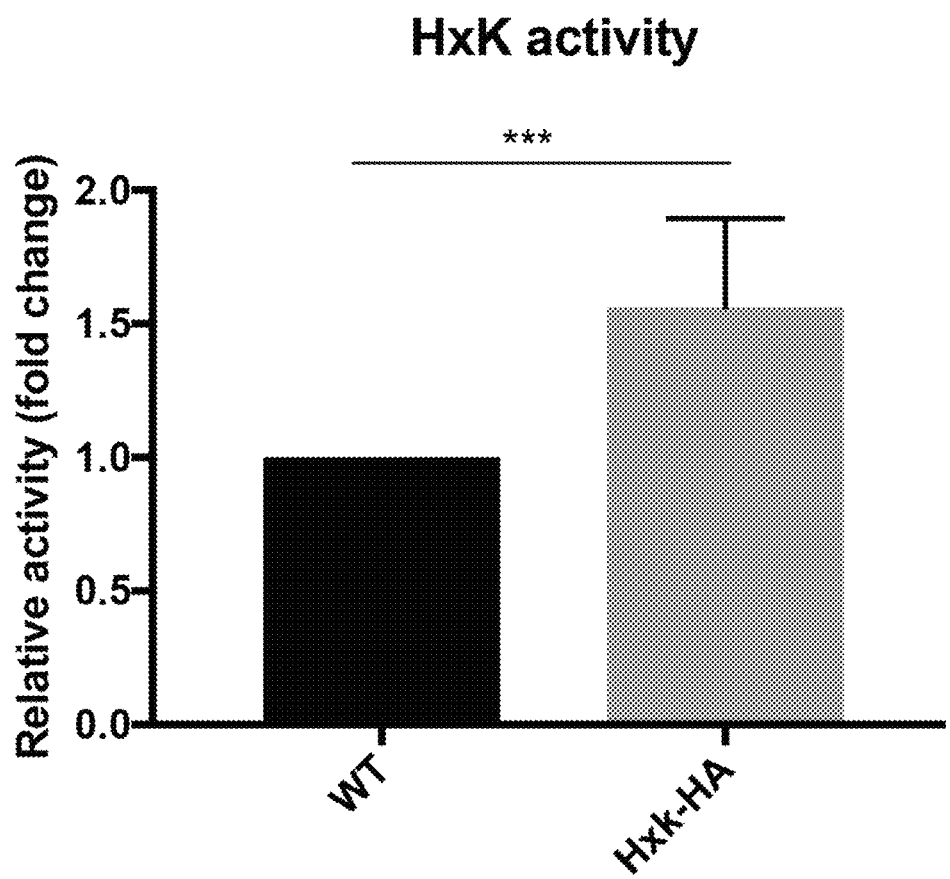
FIG. 13 C-terminal modification by dual HA-tagging of hexokinase (Δtps/tpp:HxK-HA) parasites leads to an increase in catalytic activity. Activity of HxK was determined using coupled G6PDH spectroscopic assay.

The catalytic activity of hexokinase was elevated by HA-tagging the C-terminus (FIG. 13), suggesting that the potentiation of the Δtps/tpp phenotype by HA-tagged hexokinase is due to its increased catalytic activity.

These findings indicate that TgTPS/TPP normally negatively regulates hexokinase activity and that in the absence of TgTPS/TPP, excess glucose-6-phosphate synthesized by hyperactive hexose kinase is diverted into amylopectin synthesis resulting in pathologic accumulation of amylopectin granules.

Example 5 the CBM20 and TPP Domains of TgTPS/TPP are Important for Activity

Figure 14:
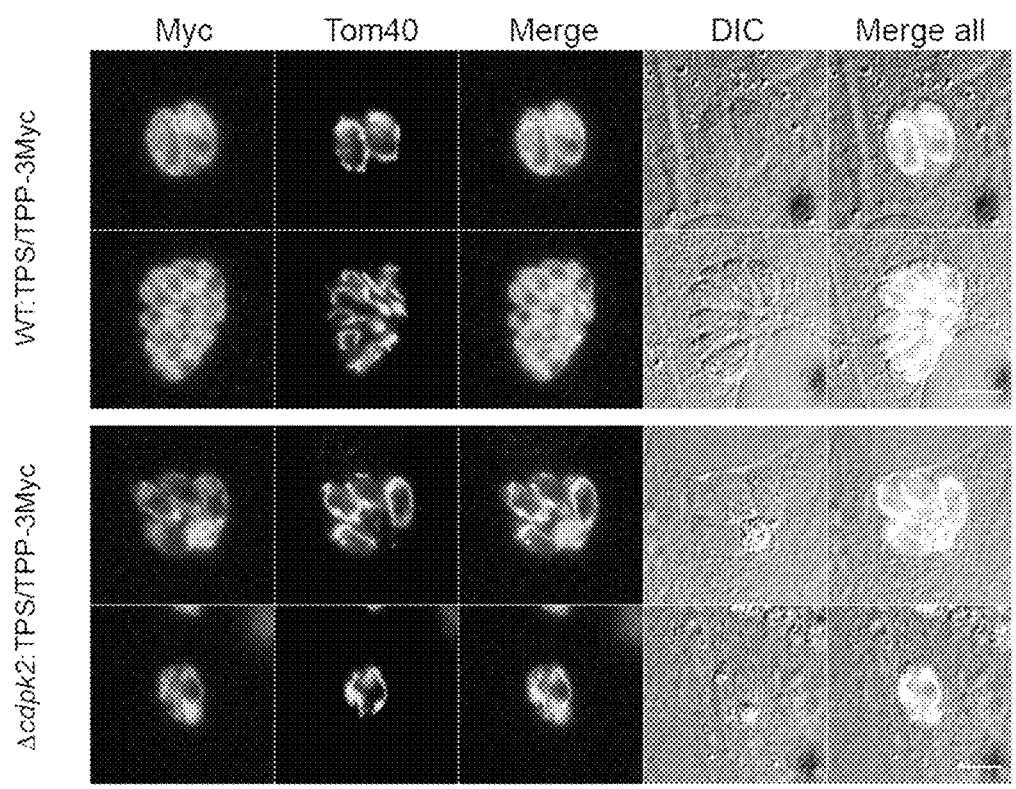
FIG. 14 shows localisation of myc-tagged TgTPS/TPP in wild-type RH parasites (upper panel) and in the *T. gondii* Δcdpk2 mutant (lower panel). The top panel shows TPS/TPP expression in wild-type parasites, while the lower panel shows that it localises to amylopectin granules when they are present, as in the case of CDPK2 KO parasites and therefore that the CBM20 domain is functional). Infected host cells were labeled with anti-myc (TgTPS/TPP) and anti-TOM (mitochondrial) antibodies and residual bodies viralized by DIC.
Figure 15:
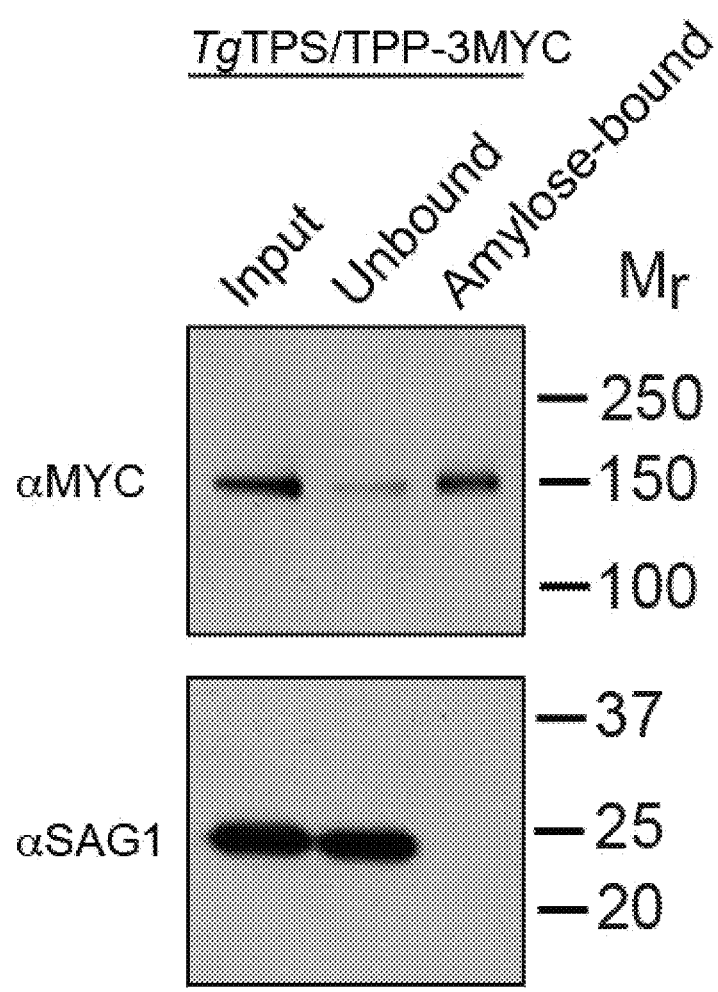
FIG. 15 RH parasites expressing TgTPS/TPP-3Myc were lyzed and cytosolic extracts fractionated on a amylose column. Myc-tagged protein was largely associated with the bound fraction.
Figure 16:
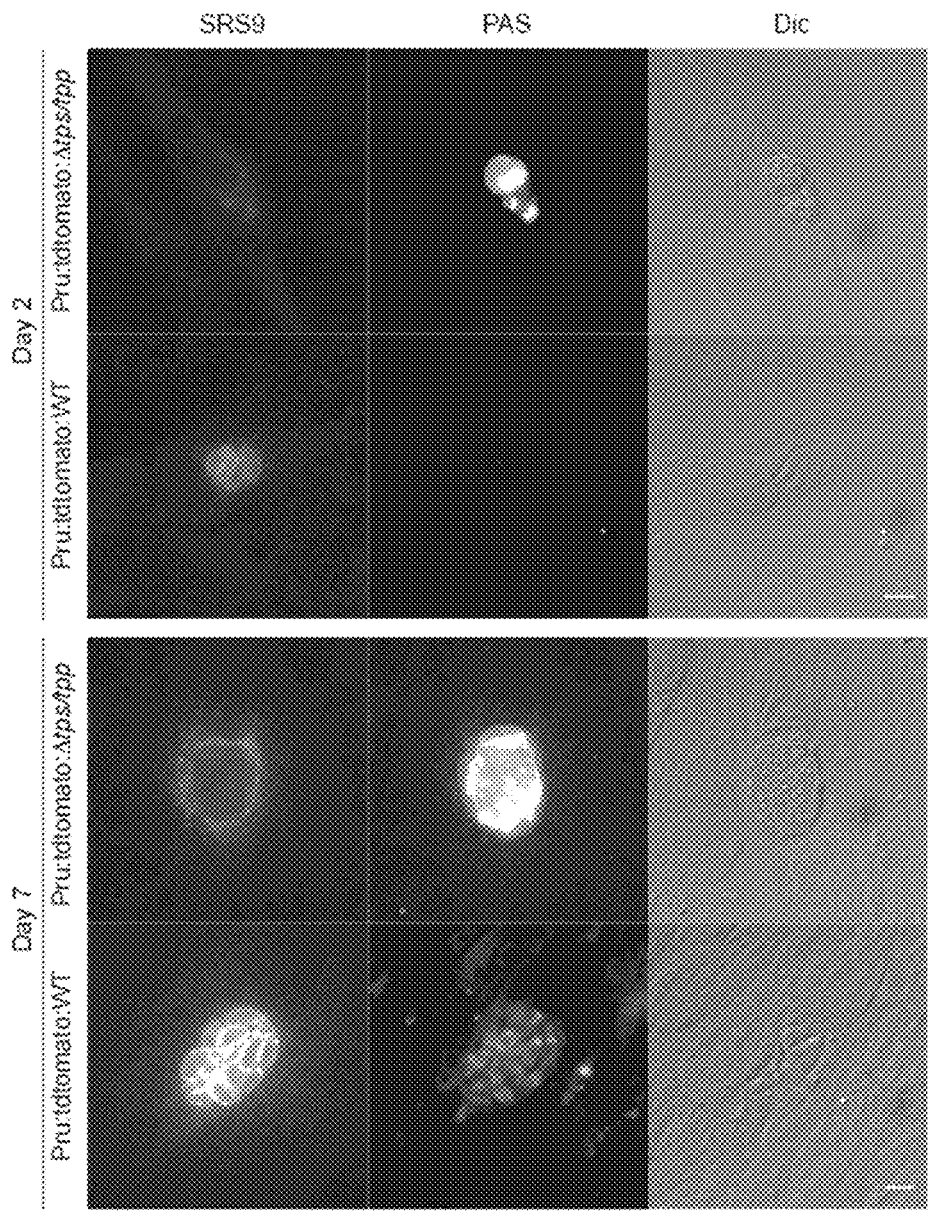
FIG. 16 Bradyzoite cyst development is defective in Δtps/tpp parasites. Host cells were infected with tachyzoites and allowed to differentiate in the presence of bradyzoite inducing medium for 2 and 7 days, before performing IFAs.

TgTPS/TPP contains an N-terminal carbohydrate-binding module (CBM20) that is predicted to bind amylopectin and was retained on an amylose column following cell lysis and passage of cytosolic extracts on this column (FIG. 15), suggesting that it might be recruited to amylopectin granules in vivo. Indeed, when a myc-tagged version of TgTPS/TPP was expressed in wild type RH parasites, the epitope was associated with small puncta that were distributed throughout the cytoplasm (FIG. 14). Strikingly, the TgTPS/TPP-myc protein was largely relocated to the residual body when expressed in RH:Δcdpk2 parasites which hyperaccumulate amylopectin granules in the residual body (FIG. 14) supporting colocalization of TgTPS/TPP with granules. Interestingly, expression of TgTPS/TPP-myc in the Δcdpk2 knockout lines revealed a second population of tagged protein that was associated with a peripheral reticulum consistent with mitochondrial localization (FIG. 14). This localization was confirmed by colabeling parasites with an antibody to the mitochondrial marker, TOM40 (FIG. 14). These data indicate that TgTPS/TPP is targeted to both amylopectin granules in the cytosol and the mitochondrial outer membrane.

Finally, to define which domains of TgTPS/TPP are involved in regulating hexose kinase activity and amylopectin accumulation, the RH:Δtgtps/tpp mutant was complemented with mutated or truncated TgTPS/TPP proteins fused to HA epitopes (Figure not shown). Genes encoding each construct were randomly integrated into chromosomal loci and populations examined by immunofluorescence microscopy (for localization of the protein and presence of amylopectin deposits in an enlarged residual body), Western blotting and GC/MS analysis for trehalose metabolites. Complementation of the knock-out lines with a construct expressing full length TgTPS/TPP fully restored normal morphology of the residual body (not shown). Complementation with a full length TgTPS/TPP protein in which key residues in the CBM20 domain required for amylopectin binding were mutated (TgTPS/TPP-CBMmut) also restored residual body phenotype, but only in cells in which high levels of expression were observed. Loss of CBM function in this construct was confirmed by amylose chromatography. Targeting of TgTPS/TPP to amylopectin granules may therefore facilitate, but not be essential for function. Significantly, expression of a truncated TgTPS/TPP protein lacking the C-terminal phosphatase domain failed to complement the mutant and prevent amylopectin accumulation and swelling of the residual body indicating that this domain is essential for function. To investigate whether other closely related phosphatase domains could substitute for the TPP domain of TgTPS/TPP, the knock-out lines was further complemented with fusion proteins in which the TPP domain of TgTPS/ TPP was replaced with the *S. pombe* trehalose-specific phosphatase TPP1 or the promiscuous *Plasmodium falciparum* sugar phosphatase NAD1. Neither of these chimeric protein complemented the amylopectin phenotype of the Δtps/tpp parasites. Similarly, complementation of the RHΔtgtps/tpp mutant with *Saccharomyces cerevisiae* TPS1 (ScTPS1) on its own and as a CBM20 fusion also failed to complement the mutant phenotype. Interesting, the RH:Δtgtps/tpp mutant line expressing ScTPS1 synthesized trehalose-6-phosphate, as determined by GC/MS analysis of whole cell lysates, confirming that these heterologous proteins are active and that trehalose-6-phosphate synthesis alone is not sufficient for the regulatory activity of TgTPS/ TPP. Finally, expression of a mutated version of TgTPS/TPP with restored putative substrate-binding residues showed a TgTPS/TPP-like localization pattern but failed to complement the Δtps/tpp phenotype.

Example 6 Bradyzoite Cyst Development is Defective in ΔTps/tpp Parasites

Two days post induction of bradyzoite differentiation, large amylopectin granules were visible in Δtps/tpp parasites, but absent in wild-type (WT) parasites. In addition, the intensity of the bradyzoite surface marker SRS9 was lower for Δtps/tpp parasites compared to WT parasites. Following 7 days of bradyzoite induction, Δtps/tpp cyst morphology was markedly disrupted by excessive amylopectin accumulation. Individual parasites are not discernible by staining with SRS9, which is found in a ring-like pattern around the periphery of the cyst-like structure. In contrast, WT parasites express high levels of SRS9 around the periphery of individual bradyzoites within cysts. The presence of small amylopectin granules characteristic of bradyzoite differentiation were also visible in WT cysts after 7 days. *Toxoplasma* cyst burden was monitored in the mouse brain using quantitative PCR. The TPS/TPP knockout (Δtps/tpp) was either completely absent or below detectable levels, demonstrating that this mutant is unable to survive as bradyzoites.

Example 7 Immunization Challenge with TPS

The inventors wanted to ascertain whether infection with Δtps/tpp strain (Patent deposit ATCC PTA-125166 corresponding to Pru:tdTomato:Dtps/tpp cl-2 (SEQ ID NO:8) could protect against a subsequent challenge with wildtype parasites thus showing the strains utility as a live attenuated vaccine. To do this the inventors first infected naïve C57BL/6 mice with $1 \times 10^4$ Δtps/tpp and waited 5 weeks. They then infected both immunized and naïve animals with $1 \times 10^4$ wildtype (Pru:tdTomato:Δhx) tachyzoites i.p, monitoring body weight daily and for signs of disease. It was seen that, as expected, naïve animals underwent a typical course of infection dropping weight from approximately day 5, and succumbing to infection between day 9 and 12 (FIG. 17A).

However, animals immunized with Δtps/tpp did not drop any weight and 100% of the animals survived the challenge (FIG. 17B). This demonstrates that Δtps/tpp immunization completely protects from challenge with a wildtype strain of *Toxoplasma*.

Remarks

The inventors show here that the multi-domain protein, TgTPS/TPP, has evolved novel regulatory functions in regulating *Toxoplasma gondii* central carbon metabolism that are essential for the intracellular growth and survival of both acute and chronic stages of these parasites. While both the TPS and TPP domains of this protein appear to lack detectable catalytic activity, they retain many of the residues needed for hexose-phosphate/sugar nucleotide bindings and may function as intracellular sugar-phosphate sensors. In the presence of high glucose concentrations, as are likely to occur in cultured host cells and in infected tissues, TgTPS/TPP may sense high intracellular glucose-6-phosphate levels and negatively regulate the activity of hexose kinase and glucose-6-phosphate flux into key pathways of central carbon metabolism. While we have been unable to detect direct interactions between TgTPS/TPP and hexose kinase using pull-down or in vivo cross-linked assays, it is possible that these proteins may associate with each other on either amylopectin granules or on the outer membrane of mitochondia. Whether TgTPS protein domains sense other metabolites, as has been proposed in some fungi and plants remains to be investigated. These findings add to a growing body of evidence suggesting that *T. gondii* is highly dependent on post-transcriptional/translational mechanims for regulating central carbon metabolism. This strategy may allow these parasites to rapidly respond to changes in carbon source availability within different cell types or tissue niches and/or to adjust their growth rate to prevailing immune responses.

Deposit Statement

*Toxoplasma gondii* mutant Pru:tdTomato:TPS/TPP (25 vials) was received by the American Type Culture Collection (ATCC) 10801 University Boulevard, Manassas, Va. on 14 Sep. 2018 and assigned patent deposit designation PTA-125166.

*Toxoplasma gondii* mutant RH:HXGPRT:Ku80:TPS/TPP:HK2HA (25 vials) was received by the American Type Culture Collection 10801 University Boulevard, Manassas, Va. on 14 Sep. 2018 and assigned patent deposit designation PTA-125164.

*Toxoplasma gondii* mutant RH:HXGPRT:TPS/TPP (25 vials) was received by the American Type Culture Collection 10801 University Boulevard, Manassas, Va. on 14 Sep. 2018 and assigned patent deposit designation PTA-125165.

The deposits will be made available in accordance with the requirements under the Budapest Treaty. However, it should be understood that the availability of a deposit does not constitute a license to practice the subject invention in derogation of patent rights granted by governmental action. Further, the subject culture deposits will be stored and made available to the public in accordance with the provisions of the Budapest Treaty for the Deposit of Microorgansim i.e. they will be stored with all the care necessary to keep them viable and uncontaminated for a period of at least five years after the most recent request for furnishing of a sample of the desposits, and in any case, for a period of at least 30 (thirty) years after the date of deposit or for the enforceable life of any patent which may issue disclosing the cultures pus five years after the last request for a sample from the deposit. The depositor acknowledges the duty to replace the deposit should the depository be unable to furnish a sample when requested, due to the condition of the deposits.

The invention claimed is:

1. An isolated mutant protozoan *Toxoplasma gondii* parasite wherein the mutant parasite is attenuated when grown or cultured in glucose-containing medium but not attenuated when grown or cultured in glucose-free medium and wherein said attenuation results from the uncontrolled accumulation of starch-like amylopectin stores when grown in glucose-containing medium, wherein the mutant parasite comprises an inactivating mutation of the trehalose-6-phosphate synthase/trehalose-6-phosphate phosphatase (TPS/TPP)-like gene of *Toxoplasma* (ΔTPS/TPP) comprising a sequence SEQ ID NO:1 or SEQ ID NO:3.

2. The mutant parasite according to claim 1, wherein the inactivating mutation is caused by a targeted or non-targeted disruption of SEQ ID NO:1 or SEQ ID NO:3.

3. The mutant parasite according to claim 1, wherein the inactivating mutation is caused by a targeted or non-targeted disruption in a coding sequence and/or a non-coding sequence and/or a regulatory sequence controlling gene transcription of SEQ ID NO:1 or SEQ ID NO:3.

4. The mutant parasite according to claim 1, wherein the inactivating mutation is a frame shift mutation in the coding sequence of SEQ ID NO:1 or SEQ ID NO:3.

5. The mutant parasite according to claim 2, wherein targeted disruption of the TPS/TPP-like gene comprises an insertion of one or more contiguous heterologous nucleotides or a deletion of one or more contiguous nucleotides in SEQ ID NO:1 or SEQ ID NO:3.

6. The mutant parasite according to claim 1, wherein the native TPS/TPP-like gene consists of the sequence set forth in SEQ ID NO:1.

7. The mutant parasite according to claim 1, wherein the native TPS/TPP-like gene consists of the sequence set forth in SEQ ID NO:3.

8. The mutant parasite according to claim 1, wherein the parasite comprises an inactivation of the CDPK2 gene of *Toxoplasma* or a C-terminal modified hexokinase (HxK) gene in combination with the inactivated or disrupted TPS/TPP-like gene, wherein starch accumulation is increased relative to wild-type non-mutated parasites.

9. The mutant parasite according to claim 8, further comprising an inactivation of the CDPK2 gene of *Toxoplasma.*

10. The mutant parasite according to claim 8, further comprising a C-terminal modified hexokinase (HxK) gene.

11. The mutant parasite according to claim 1, wherein the mutant is selected from one of the following:

(i) a *Toxoplasma gondii* mutant deposited with the ATCC and designated PTA-125166;

(ii) a *Toxoplasma gondii* mutant deposited with the ATCC and designated PTA-125164; and (iii) *Toxoplasma gondii* mutant deposited with the ATCC and designated PTA-125165.

12. A vaccine comprising an isolated mutant protozoan *Toxoplasma gondii* parasite of claim 1.

13. The vaccine according to claim 12, wherein the parasite comprises an inactivating mutation of SEQ ID NO:1.

14. The vaccine according to claim 12, further comprising a pharmaceutically acceptable carrier or excipient.

15. The vaccine according to claim 12, wherein oocyst shedding is substantially reduced or prevented in a human or non-human animal vaccinated with the vaccine.

16. A method of vaccinating an animal against a *Toxoplasma* parasite or against a *Toxoplasma* parasitic infection or condition without concomitant oocyst shedding, comprising administering to the animal a mutant *Toxoplasma gondii* parasite according to claim 1.

17. A method for vaccinating an animal against a *Toxoplasma* parasite or against a *Toxoplasma* parasitic infection or condition without concomitant oocyst shedding, comprising administering to the animal the vaccine according to claim 12.

18. A method for vaccinating an animal against toxoplasmosis without concomitant oocyst shedding or of preventing toxoplasmosis in an animal, comprising administering to the animal a mutant *Toxoplasma gondii* parasite according to claim 1.

19. The vaccine according to claim 12, wherein the vaccine comprises mutant *Toxoplasma* tachyzoites, bradyzoites or oocysts.

20. A method for vaccinating an animal against toxoplasmosis without concomitant oocyst shedding or of preventing toxoplasmosis in an animal, the method comprising administering to the animal the vaccine according to claim 13.

21. The vaccine according to claim 12, wherein the parasite comprises an inactivating mutation of SEQ ID NO:3.

22. A method for vaccinating an animal against toxoplasmosis without concomitant oocyst shedding or of preventing toxoplasmosis in an animal, the method comprising administering to the animal the vaccine according to claim 21.

* * * * *